United States Patent
Francis et al.

(10) Patent No.: US 8,198,229 B2
(45) Date of Patent: Jun. 12, 2012

(54) METHODS OF TREATING UROGENITAL-NEUROLOGICAL DISORDERS USING GALANIN RETARGETED ENDOPEPIDASES

(75) Inventors: Joseph Francis, Aliso Viejo, CA (US); Dean G. Stathakis, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 275 days.

(21) Appl. No.: 12/781,078

(22) Filed: May 17, 2010

(65) Prior Publication Data
US 2010/0303787 A1     Dec. 2, 2010

Related U.S. Application Data

(60) Provisional application No. 61/182,188, filed on May 29, 2009.

(51) Int. Cl.
*C07K 14/00* (2006.01)
*C12N 9/00* (2006.01)

(52) U.S. Cl. ............................................ 514/1; 435/183
(58) Field of Classification Search ....... 514/1; 435/183
See application file for complete search history.

(56) References Cited

U.S. PATENT DOCUMENTS

| | | | |
|---|---|---|---|
| 7,151,084 B2 | 12/2006 | Miller | |
| 8,012,491 B2 * | 9/2011 | Shone et al. | 424/247.1 |
| 8,067,200 B2 * | 11/2011 | Foster et al. | 435/69.1 |
| 2009/0104234 A1 | 4/2009 | Francis | |

FOREIGN PATENT DOCUMENTS

| WO | WO 99/03483 A1 | 1/1999 |
|---|---|---|
| WO | WO 2008-008805 A2 | 1/2008 |
| WO | WO 2009/055351 A1 | 4/2009 |

* cited by examiner

*Primary Examiner* — Karen Cochrane Carlson
(74) *Attorney, Agent, or Firm* — Kenton Abel; Debra Condino

(57) ABSTRACT

The present specification discloses TVEMPs, compositions comprising such toxins and methods of treating urogenital-neurological disorders in a mammal using such TVEMPs and compositions.

11 Claims, 7 Drawing Sheets

FIG. 1B.

METHODS OF TREATING UROGENITAL-NEUROLOGICAL DISORDERS USING GALANIN RETARGETED ENDOPEPIDASES

CROSS REFERENCE

This patent application claims priority pursuant to 35 U.S.C. §119(e) to U.S. Provisional Patent Application Ser. No. 61/182,188 filed May 29, 2009, which is hereby incorporated by reference in its entirety.

The ability of Clostridial toxins, such as, e.g., Botulinum neurotoxins (BoNTs), Botulinum neurotoxin serotype A (BoNT/A), Botulinum neurotoxin serotype B (BoNT/B), Botulinum neurotoxin serotype C1 (BoNT/C1), Botulinum neurotoxin serotype D (BoNT/D), Botulinum neurotoxin serotype E (BoNT/E), Botulinum neurotoxin serotype F (BoNT/F), and Botulinum neurotoxin serotype G (BoNT/G), and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Beaufour Ipsen, Porton Down, England), NEURONOX® (Medy-Tox, Inc., Ochang-myeon, South Korea) BTX-A (Lanzhou Institute Biological Products, China) and XEOMIN® (Merz Pharmaceuticals, GmbH., Frankfurt, Germany); and BoNT/B preparations, such as, e.g., MYOBLOC™/NEUROBLOC™ (Elan Pharmaceuticals, San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

Clostridial toxin therapies are successfully used for many indications. Generally, administration of a Clostridial toxin treatment is well tolerated. However, toxin administration in some applications can be challenging because of the larger doses required to achieve a beneficial effect. Larger doses can increase the likelihood that the toxin may move through the interstitial fluids and the circulatory systems, such as, e.g., the cardiovascular system and the lymphatic system, of the body, resulting in the undesirable dispersal of the toxin to areas not targeted for toxin treatment. Such dispersal can lead to undesirable side effects, such as, e.g., inhibition of neurotransmitter release in neurons not targeted for treatment or paralysis of a muscle not targeted for treatment. For example, a patient administered a therapeutically effective amount of a BoNT/A treatment into the neck muscles for torticollis may develop dysphagia because of dispersal of the toxin into the oropharynx. As another example, a patient administered a therapeutically effective amount of a BoNT/A treatment into the bladder for overactive bladder may develop dry mouth and/or dry eyes. Thus, there remains a need for improved Clostridial toxins that are effective at the site of treatment, but have negligible to minimal effects in areas not targeted for a toxin treatment.

A Clostridial toxin treatment inhibits neurotransmitter release by disrupting the exocytotic process used to secret the neurotransmitter into the synaptic cleft. There is a great desire by the pharmaceutical industry to expand the use of Clostridial toxin therapies beyond its current myo-relaxant applications to treat other nerve-based ailments, such as, e.g., various kinds of chronic pain, neurogenic inflammation and urogenital disorders, as well as other disorders, such as, e.g., pancreatitis. One approach that is currently being exploited to expand Clostridial toxin-based therapies involves modifying a Clostridial toxin so that the modified toxin has an altered cell targeting capability for a non-Clostridial toxin target cell. This re-targeted capability is achieved by replacing a naturally-occurring targeting domain of a Clostridial toxin with a targeting domain showing a preferential binding activity for a non-Clostridial toxin receptor present in a non-Clostridial toxin target cell. Such modifications to a targeting domain result in a Clostridial toxin chimeric called a Targeted Vesicular Exocytosis Modulating Protein (TVEMP) that is able to selectively bind to a non-Clostridial toxin receptor (target receptor) present on a non-Clostridial toxin target cell (retargeted). A Clostridial toxin chimeric with a targeting activity for a non-Clostridial toxin target cell can bind to a receptor present on the non-Clostridial toxin target cell, translocate into the cytoplasm, and exert its proteolytic effect on the SNARE complex of the non-Clostridial toxin target cell.

The present specification discloses TVEMP compositions and methods for treating an individual suffering from a neuron-mediated urogenital disorder. This is accomplished by administering a therapeutically effective amount of a composition comprising a TVEMP to an individual in need thereof. The disclosed methods provide a safe, inexpensive, out patient-based treatment for the treatment of urogenital-neurological disorders.

Thus, aspects of the present invention provide a composition comprising a TVEMP comprising a retargeted peptide binding domain, a Clostridial toxin translocation domain and a Clostridial toxin enzymatic domain. A composition comprising a TVEMP can be a pharmaceutical composition. Such a pharmaceutical composition can comprise, in addition to a TVEMP, a pharmaceutical carrier, a pharmaceutical component, or both.

Other aspects of the present invention provide a method of treating urogenital-neurological disorder in a mammal, the method comprising the step of administering to the mammal a therapeutically effective amount of a composition including a TVEMP comprising a retargeted peptide binding domain, a Clostridial toxin translocation domain and a Clostridial toxin enzymatic domain.

Other aspects of the present invention provide a manufacturing of a medicament for treating urogenital-neurological disorder in a mammal in need thereof, the medicament comprising a TVEMP including a retargeted peptide binding domain, a Clostridial toxin translocation domain and a Clostridial toxin enzymatic domain.

Other aspects of the present invention provide a use of a composition for treating urogenital-neurological disorder in a mammal in need thereof, the use comprising the step of administering to the mammal in need thereof a therapeutically effective amount of a composition, wherein the composition comprises a TVEMP including a retargeted peptide binding domain, a Clostridial toxin translocation domain and a Clostridial toxin enzymatic domain and wherein administration of the composition reduces a symptom of the urogenital-neurological disorder, thereby treating the mammal.

BRIEF DESCRIPTION OF THE DRAWINGS

FIG. 1 shows a schematic of the current paradigm of neurotransmitter release and Clostridial toxin intoxication in a central and peripheral neuron. FIG. 1B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the $H_N$ domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

FIG. 3 shows TVEMPs with an enhanced targeting domain located at the amino terminus of the modified toxin.

FIG. 4 shows TVEMPs with an enhanced targeting domain located between the other two domains.

FIG. 5 shows TVEMPs with an enhanced targeting domain located at the carboxyl terminus of the modified toxin.

DETAILED DESCRIPTION

Figure 1A:
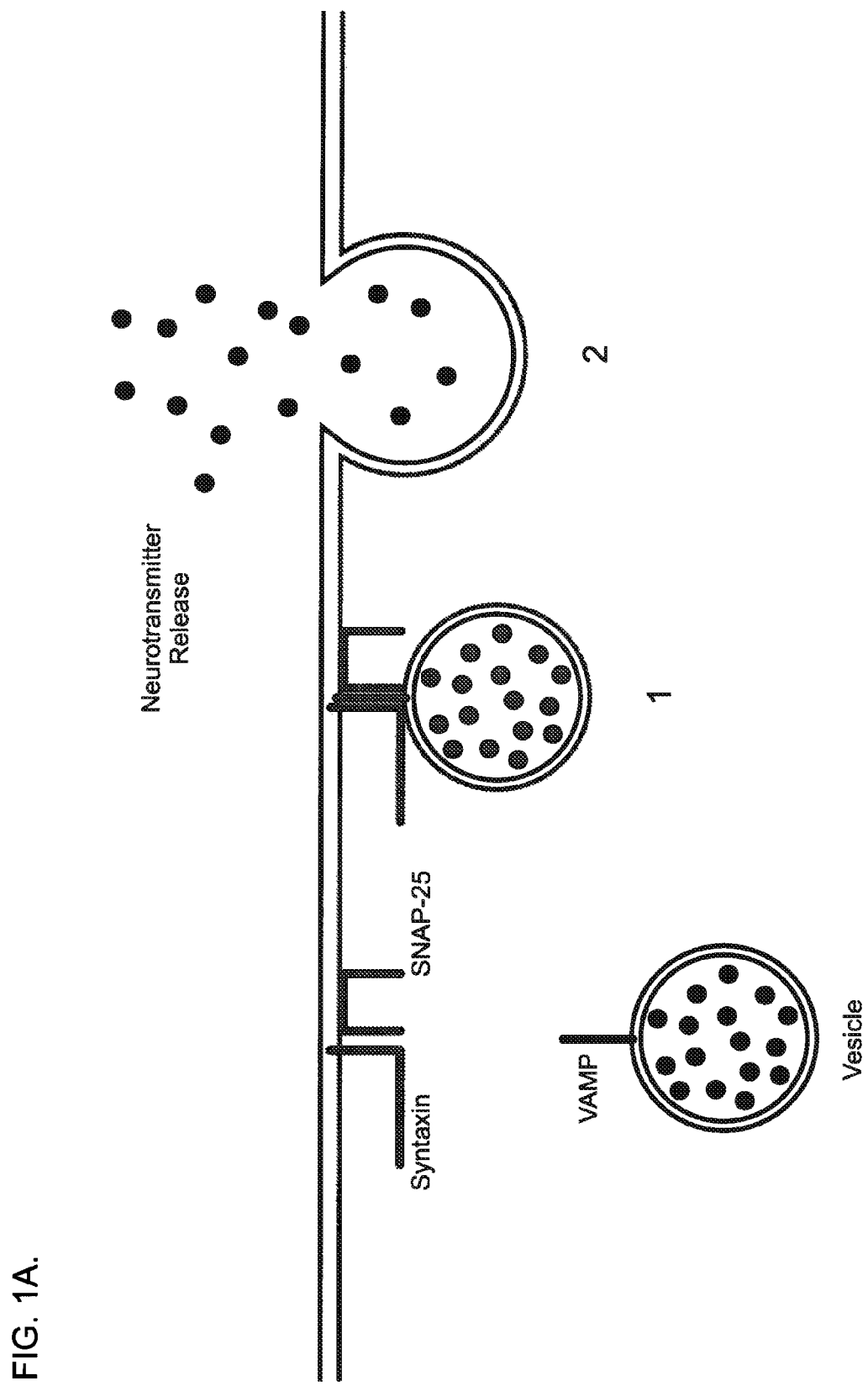
FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed.

Aspects of the present invention provide, in part, a TVEMP. As used herein, a "Targeted Vesicular Exocytosis Modulating Protein" is synonomous with "TVEMP" and refers to any molecule comprising a retargeted peptide binding domain, a Clostridial toxin translocation domain and a Clostridial toxin enzymatic domain. Exemplary TVEMPs useful to practice aspects of the present invention are disclosed in, e.g., Steward, L. E. et al., *Modified Clostridial Toxins with Enhanced Translocation Capabilities and Altered Targeting Activity For Non-Clostridial Toxin Target Cells*, U.S. patent application Ser. No. 11/776,075 (Jul. 11, 2007); Dolly, J. O. et al., *Activatable Clostridial Toxins*, U.S. patent application Ser. No. 11/829,475 (Jul. 27, 2007); Foster, K. A. et al., *Fusion Proteins*, International Patent Publication WO 2006/059093 (Jun. 8, 2006); and Foster, K. A. et al., *Non-Cytotoxic Protein Conjugates*, International Patent Publication WO 2006/059105 (Jun. 8, 2006), each of which is incorporated by reference in its entirety.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of C. tetani. Two other species of Clostridia, C. baratii and C. butyricum, also produce toxins, BaNT and BuNT respectively, which are similar to BoNT/F and BoNT/E, respectively.

Each mature di-chain molecule comprises three functionally distinct domains: 1) an enzymatic domain located in the light chain (LC) that includes a metalloprotease region containing a zinc-dependent endopeptidase activity which specifically targets core components of the neurotransmitter release apparatus; 2) a translocation domain ($H_N$) contained within the amino-terminal half of the heavy chain (HC) that facilitates release of the LC from intracellular vesicles into the cytoplasm of the target cell; and 3) a binding domain ($H_C$) found within the carboxyl-terminal half of the HC that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains. Table 1 gives approximate boundary regions for each domain found in exemplary Clostridial toxins.

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-K445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |
| BaNT | 9 | M1-K431 | N432-I857 | I858-E1268 |
| BuNT | 10 | M1-R422 | K423-I847 | Y1086-K1251 |

Figure 1B:
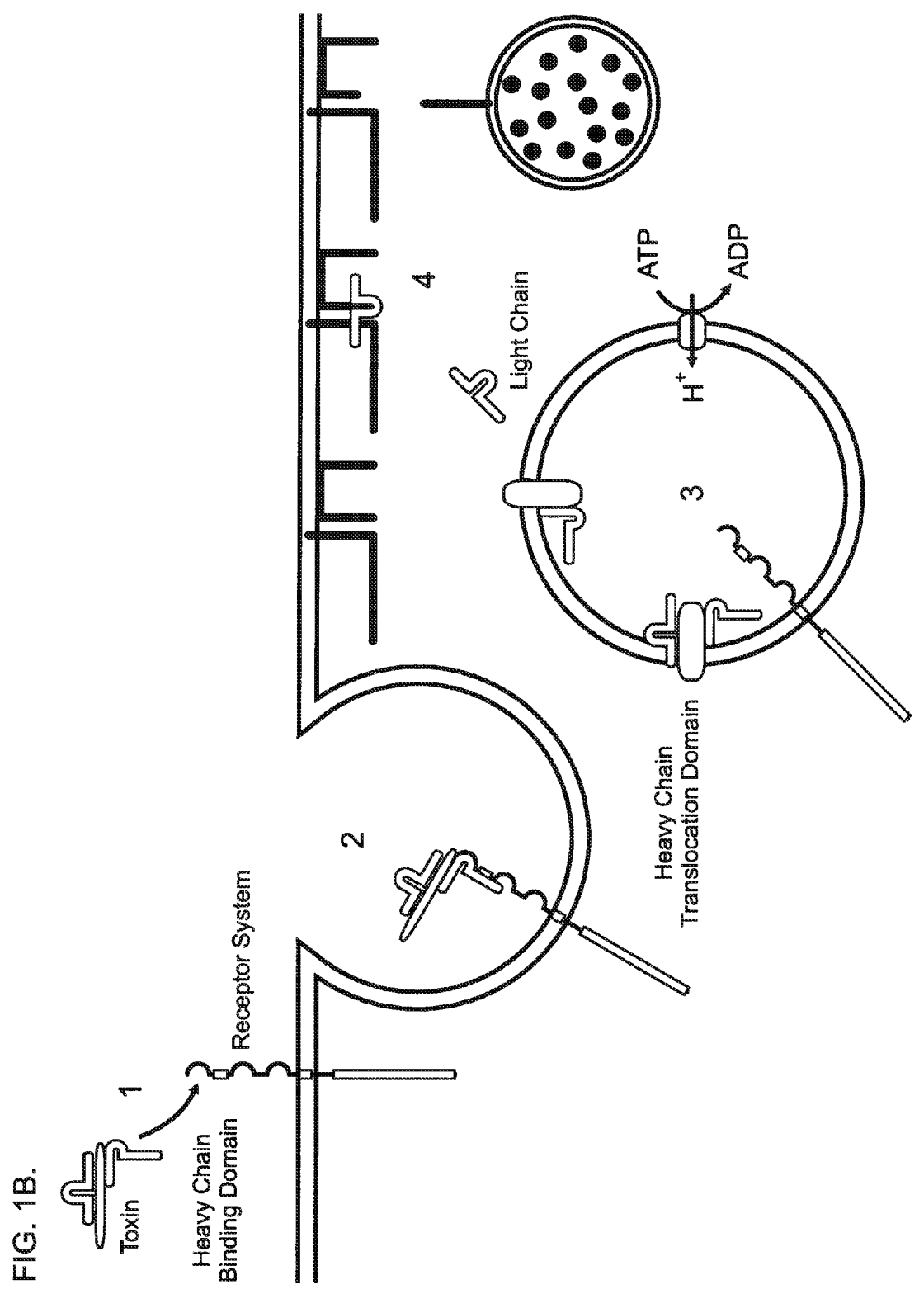

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (see FIG. 1). The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically target one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11(9) Trends Microbiol. 431-437, (2003).

In an aspect of the invention, a TVEMP comprises, in part, a Clostridial toxin enzymatic domain. As used herein, the term "Clostridial toxin enzymatic domain" refers to any Clostridial toxin polypeptide that can execute the enzymatic target modification step of the intoxication process. Thus, a Clostridial toxin enzymatic domain specifically targets a Clostridial toxin substrate and encompasses the proteolytic cleavage of a Clostridial toxin substrate, such as, e.g., SNARE proteins like a SNAP-25 substrate, a VAMP substrate and a Syntaxin substrate. Non-limiting examples of a Clostridial toxin enzymatic domain include, e.g., a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, and a BuNT enzymatic domain. Other non-limiting examples of a Clostridial toxin enzymatic domain include, e.g., amino acids 1-448 of SEQ ID NO: 1, amino acids 1-441 of SEQ ID NO: 2, amino acids 1-449 of SEQ ID NO: 3, amino acids 1-445 of SEQ ID NO: 4, amino acids 1-422 of SEQ ID NO: 5, amino acids 1-439 of SEQ ID NO: 6, amino acids 1-446 of SEQ ID NO: 7, amino acids 1-457 of SEQ ID NO: 8, amino acids 1-431 of SEQ ID NO: 9, and amino acids 1-422 of SEQ ID NO: 10.

A Clostridial toxin enzymatic domain includes, without limitation, naturally occurring Clostridial toxin enzymatic domain variants, such as, e.g., Clostridial toxin enzymatic domain isoforms and Clostridial toxin enzymatic domain subtypes; and non-naturally occurring Clostridial toxin enzymatic domain variants, such as, e.g., conservative Clostridial toxin enzymatic domain variants, non-conservative Clostridial toxin enzymatic domain variants, Clostridial toxin enzymatic domain chimerics, active Clostridial toxin enzymatic domain fragments thereof, or any combination thereof.

As used herein, the term "Clostridial toxin enzymatic domain variant," whether naturally-occurring or non-naturally-occurring, refers to a Clostridial toxin enzymatic domain that has at least one amino acid change from the corresponding region of the disclosed reference sequences (Table 1) and can be described in percent identity to the corresponding region of that reference sequence. Unless expressly indicated, Clostridial toxin enzymatic domain variants useful to practice disclosed embodiments are variants that execute the enzymatic target modification step of the intoxication process. As non-limiting examples, a BoNT/A enzymatic domain variant comprising amino acids 1-448 of SEQ ID NO: 1 will have at least one amino acid difference, such as, e.g., an amino acid substitution, deletion or addition, as compared to the amino acid region 1-448 of SEQ ID NO: 1; a BoNT/B enzymatic domain variant comprising amino acids 1-441 of SEQ ID NO: 2 will have at least one amino acid difference, such as, e.g., an amino acid substitution, deletion or addition, as compared to the amino acid region 1-441 of SEQ ID NO: 2; a BoNT/C1 enzymatic domain variant comprising amino acids 1-449 of SEQ ID NO: 3 will have at least one amino acid difference, such as, e.g., an amino acid substitution, deletion or addition, as compared to the amino acid region 1-449 of SEQ ID NO: 3; a BoNT/D enzymatic domain variant comprising amino acids 1-445 of SEQ ID NO: 4 will have at least one amino acid difference, such as, e.g., an amino acid substitution, deletion or addition, as compared to the amino acid region 1-445 of SEQ ID NO: 4; a BoNT/E enzymatic domain variant comprising amino acids 1-422 of SEQ ID NO: 5 will have at least one amino acid difference, such as, e.g., an amino acid substitution, deletion or addition, as compared to the amino acid region 1-422 of SEQ ID NO: 5; a BoNT/F enzymatic domain variant comprising amino acids 1-439 of SEQ ID NO: 6 will have at least one amino acid difference, such as, e.g., an amino acid substitution, deletion or addition, as compared to the amino acid region 1-439 of SEQ ID NO: 6; a BoNT/G enzymatic domain variant comprising amino acids 1-446 of SEQ ID NO: 7 will have at least one amino acid difference, such as, e.g., an amino acid substitution, deletion or addition, as compared to the amino acid region 1-446 of SEQ ID NO: 7; and a TeNT enzymatic domain variant comprising amino acids 1-457 of SEQ ID NO: 8 will have at least one amino acid difference, such as, e.g., an amino acid substitution, deletion or addition, as compared to the amino acid region 1-457 of SEQ ID NO: 8.

It is recognized by those of skill in the art that within each serotype of Clostridial toxin there can be naturally occurring Clostridial toxin enzymatic domain variants that differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific enzymatic domain subtypes showing approximately 95% amino acid identity when compared to another BoNT/A enzymatic domain subtype. As used herein, the term "naturally occurring Clostridial toxin enzymatic domain variant" refers to any Clostridial toxin enzymatic domain produced by a naturally-occurring process, including, without limitation, Clostridial toxin enzymatic domain isoforms produced from alternatively-spliced transcripts, Clostridial toxin enzymatic domain isoforms produced by spontaneous mutation and Clostridial toxin enzymatic domain subtypes. A naturally occurring Clostridial toxin enzymatic domain variant can function in substantially the same manner as the reference Clostridial toxin enzymatic domain on which the naturally occurring Clostridial toxin enzymatic domain variant is based, and can be substituted for the reference Clostridial toxin enzymatic domain in any aspect of the present invention.

A non-limiting example of a naturally occurring Clostridial toxin enzymatic domain variant is a Clostridial toxin enzymatic domain isoform such as, e.g., a BoNT/A enzymatic domain isoform, a BoNT/B enzymatic domain isoform, a BoNT/C1 enzymatic domain isoform, a BoNT/D enzymatic domain isoform, a BoNT/E enzymatic domain isoform, a BoNT/F enzymatic domain isoform, a BoNT/G enzymatic domain isoform, and a TeNT enzymatic domain isoform. Another non-limiting example of a naturally occurring Clostridial toxin enzymatic domain variant is a Clostridial toxin enzymatic domain subtype such as, e.g., an enzymatic domain from subtype BoNT/A1, BoNT/A2, BoNT/A3, BoNT/A4 and BoNT/A5; an enzymatic domain from subtype BoNT/B1, BoNT/B2, BoNT/B bivalent and BoNT/B nonproteolytic; an enzymatic domain from subtype BoNT/C1-1 and BoNT/C1-2; an enzymatic domain from subtype BoNT/E1, BoNT/E2 and BoNT/E3; and an enzymatic domain from subtype BoNT/F1, BoNT/F2, BoNT/F3 and BoNT/F4.

As used herein, the term "non-naturally occurring Clostridial toxin enzymatic domain variant" refers to any Clostridial toxin enzymatic domain produced with the aid of human manipulation, including, without limitation, Clostridial toxin enzymatic domains produced by genetic engineering using random mutagenesis or rational design and Clostridial toxin enzymatic domains produced by chemical synthesis. Non-limiting examples of non-naturally occurring Clostridial toxin enzymatic domain variants include, e.g., conservative Clostridial toxin enzymatic domain variants, non-conservative Clostridial toxin enzymatic domain variants, Clostridial toxin enzymatic domain chimeric variants and active Clostridial toxin enzymatic domain fragments.

As used herein, the term "conservative Clostridial toxin enzymatic domain variant" refers to a Clostridial toxin enzymatic domain that has at least one amino acid substituted by another amino acid or an amino acid analog that has at least one property similar to that of the original amino acid from the reference Clostridial toxin enzymatic domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin enzymatic domain variant can function in substantially the same manner as the reference Clostridial toxin enzymatic domain on which the conservative Clostridial toxin enzymatic domain variant is based, and can be substituted for the reference Clostridial toxin enzymatic domain in any aspect of the present invention. Non-limiting examples of a conservative Clostridial toxin enzymatic domain variant include, e.g., conservative BoNT/A enzymatic domain variants, conservative BoNT/B enzymatic domain variants, conservative BoNT/C1 enzymatic domain variants, conservative BoNT/D enzymatic domain variants, conservative BoNT/E enzymatic domain variants, conservative BoNT/F enzymatic domain variants, conservative BoNT/G enzymatic domain variants, and conservative TeNT enzymatic domain variants.

As used herein, the term "non-conservative Clostridial toxin enzymatic domain variant" refers to a Clostridial toxin enzymatic domain in which 1) at least one amino acid is deleted from the reference Clostridial toxin enzymatic domain on which the non-conservative Clostridial toxin enzymatic domain variant is based; 2) at least one amino acid added to the reference Clostridial toxin enzymatic domain on which the non-conservative Clostridial toxin enzymatic domain is based; or 3) at least one amino acid is substituted by another amino acid or an amino acid analog that does not share any property similar to that of the original amino acid from the reference Clostridial toxin enzymatic domain sequence (Table 1). A non-conservative Clostridial toxin enzymatic domain variant can function in substantially the same manner as the reference Clostridial toxin enzymatic domain on which the non-conservative Clostridial toxin enzymatic domain variant is based, and can be substituted for the reference Clostridial toxin enzymatic domain in any aspect of the present invention. Non-limiting examples of a non-conservative Clostridial toxin enzymatic domain variant include, e.g., non-conservative BoNT/A enzymatic domain variants, non-conservative BoNT/B enzymatic domain variants, non-conservative BoNT/C1 enzymatic domain variants, non-conservative BoNT/D enzymatic domain variants, non-conservative BoNT/E enzymatic domain variants, non-conservative BoNT/F enzymatic domain variants, non-conservative BoNT/G enzymatic domain variants, and non-conservative TeNT enzymatic domain variants.

As used herein, the term "Clostridial toxin enzymatic domain chimeric" refers to a polypeptide comprising at least a portion of a Clostridial toxin enzymatic domain and at least a portion of at least one other polypeptide to form a toxin enzymatic domain with at least one property different from the reference Clostridial toxin enzymatic domains of Table 1, with the proviso that this Clostridial toxin enzymatic domain chimeric is still capable of specifically targeting the core components of the neurotransmitter release apparatus and thus participate in executing the overall cellular mechanism whereby a Clostridial toxin proteolytically cleaves a substrate. Such Clostridial toxin enzymatic domain chimerics are described in, e.g., Lance E. Steward et al., *Leucine-based Motif and Clostridial Toxins*, U.S. Patent Publication 2003/0027752 (Feb. 6, 2003); Lance E. Steward et al., *Clostridial Neurotoxin Compositions and Modified Clostridial Neurotoxins*, U.S. Patent Publication 2003/0219462 (Nov. 27, 2003); and Lance E. Steward et al., *Clostridial Neurotoxin Compositions and Modified Clostridial Neurotoxins*, U.S. Patent Publication 2004/0220386 (Nov. 4, 2004), each of which is incorporated by reference in its entirety.

As used herein, the term "active Clostridial toxin enzymatic domain fragment" refers to any of a variety of Clostridial toxin fragments comprising the enzymatic domain can be useful in aspects of the present invention with the proviso that these enzymatic domain fragments can specifically target the core components of the neurotransmitter release apparatus and thus participate in executing the overall cellular mechanism whereby a Clostridial toxin proteolytically cleaves a substrate. The enzymatic domains of Clostridial toxins are approximately 420-460 amino acids in length and comprise an enzymatic domain (Table 1). Research has shown that the entire length of a Clostridial toxin enzymatic domain is not necessary for the enzymatic activity of the enzymatic domain. As a non-limiting example, the first eight amino acids of the BoNT/A enzymatic domain (residues 1-8 of SEQ ID NO: 1) are not required for enzymatic activity. As another non-limiting example, the first eight amino acids of the TeNT enzymatic domain (residues 1-8 of SEQ ID NO: 8) are not required for enzymatic activity. Likewise, the carboxyl-terminus of the enzymatic domain is not necessary for activity. As a non-limiting example, the last 32 amino acids of the BoNT/A enzymatic domain (residues 417-448 of SEQ ID NO: 1) are not required for enzymatic activity. As another non-limiting example, the last 31 amino acids of the TeNT enzymatic domain (residues 427-457 of SEQ ID NO: 8) are not required for enzymatic activity. Thus, aspects of this embodiment can include Clostridial toxin enzymatic domains comprising an enzymatic domain having a length of, e.g., at least 350 amino acids, at least 375 amino acids, at least 400 amino acids, at least 425 amino acids or at least 450 amino acids. Other aspects of this embodiment can include Clostridial toxin enzymatic domains comprising an enzymatic domain having a length of, e.g., at most 350 amino acids, at most 375 amino acids, at most 400 amino acids, at most 425 amino acids or at most 450 amino acids.

Any of a variety of sequence alignment methods can be used to determine percent identity of naturally-occurring Clostridial toxin enzymatic domain variants and non-naturally-occurring Clostridial toxin enzymatic domain variants, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice*, 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments*, 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences*, 8(5) CABIOS 501-509 (1992); Gibbs sampling, see, e.g., C. E. Lawrence et al., *Detecting Subtle Sequence Signals: A Gibbs Sampling Strategy for Multiple Alignment*, 262(5131) Science 208-214 (1993); Align-M, see, e.g., Ivo Van Walle et al., *Align-M—A New Algorithm for Multiple Alignment of Highly Divergent Sequences*, 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison*, 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment*, 302(1) J. Mol. Biol. 205-217 (2000); MUSCLE, see, e.g., Robert C. Edgar, *MUSCLE: Multiple Sequence Alignment With High Score Accuracy and High Throughput*, 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment*, 6(1) BMC Bioinformatics 66 (2005).

The present specification describes various polypeptide variants where one amino acid is substituted for another, such as, e.g., Clostridial toxin variants, Clostridial toxin enzymatic domain variants, Clostridial toxin translocation domain variants, Clostridial toxin binding domain variants, non-Clostridial toxin binding domain variants, retargeted peptide binding domain variants, and protease cleavage site variants. A substitution can be assessed by a variety of factors, such as, e.g., the physic properties of the amino acid being substituted (Table 2) or how the original amino acid would tolerate a substitution (Table 3). The selections of which amino acid can be substituted for another amino acid in a polypeptide are known to a person of ordinary skill in the art.

TABLE 2

Amino Acid Properties

| Property | Amino Acids |
| --- | --- |
| Aliphatic | G, A, I, L, M, P, V |
| Aromatic | F, H, W, Y |
| C-beta branched | I, V, T |
| Hydrophobic | C, F, I, L, M, V, W |
| Small polar | D, N, P |
| Small non-polar | A, C, G, S, T |
| Large polar | E, H, K, Q, R, W, Y |
| Large non-polar | F, I, L, M, V |
| Charged | D, E, H, K, R |
| Uncharged | C, S, T |
| Negative | D, E |
| Positive | H, K, R |
| Acidic | D, E |
| Basic | K, R |
| Amide | N, Q |

TABLE 3

Amino Acid Substitutions

| Amino Acid | Favored Substitution | Neutral Substitutions | Disfavored substitution |
| --- | --- | --- | --- |
| A | G, S, T | C, E, I, K, M, L, P, Q, R, V | D, F, H, N, Y, W |
| C | F, S, Y, W | A, H, I, M, L, T, V | D, E, G, K, N, P, Q, R |
| D | E, N | G, H, K, P, Q, R, S, T | A, C, I, L |
| E | D, K, Q | A, H, N, P, R, S, T | C, F, G, I, L, M, V, W, Y |
| F | M, L, W, Y | C, I, V | A, D, E, G, H, K, N, P, Q, R, S, T |
| G | A, S | D, K, N, P, Q, R | C, E, F, H, I, L, M, T, V, W, Y |
| H | N, Y | C, D, E, K, Q, R, S, T, W | A, F, G, I, L, M, P, V |
| I | V, L, M | A, C, T, F, Y | D, E, G, H, K, N, P, Q, R, S, W |
| K | Q, E, R | A, D, G, H, M, N, P, S, T | C, F, I, L, V, W, Y |
| L | F, I, M, V | A, C, W, Y | D, E, G, H, K, N, P, Q, R, S, T |
| M | F, I, L, V | A, C, R, Q, K, T, W, Y | D, E, G, H, N, P, S |
| N | D, H, S | E, G, K, Q, R, T | A, C, F, I, L, M, P, V, W, Y |
| P | — | A, D, E, G, K, Q, R, S, T | C, F, H, I, L, M, N, V, W, Y |
| Q | E, K, R | A, D, G, H, M, N, P, S, T | C, F, I, L, V, W, Y |
| R | K, Q | A, D, E, G, H, M, N, P, S, T | C, F, I, L, V, W, Y |
| S | A, N, T | C, D, E, G, H, K, P, Q, R, T | F, I, L, M, V, W, Y |
| T | S | A, C, D, E, H, I, K, M, N, P, Q, R, V | F, G, L, W, Y |
| V | I, L, M | A, C, F, T, Y | D, E, G, H, K, N, P, Q, R, S, W |
| W | F, Y | H, L, M | A, C, D, E, G, I, K, N, P, Q, R, S, T, V |
| Y | F, H, W | C, I, L, M, V | A, D, E, G, K, N, P, Q, R, S, T |

Matthew J. Betts and Robert, B. Russell, Amino Acid Properties and Consequences of Substitutions, pp. 289-316, In Bioinformatics for Geneticists, (eds Michael R. Barnes, Ian C. Gray, Wiley, 2003).

Thus, in an embodiment, a TVEMP disclosed in the present specification comprises a Clostridial toxin enzymatic domain. In an aspect of this embodiment, a Clostridial toxin enzymatic domain comprises a naturally occurring Clostridial toxin enzymatic domain variant, such as, e.g., a Clostridial toxin enzymatic domain isoform or a Clostridial toxin enzymatic domain subtype. In another aspect of this embodiment, a Clostridial toxin enzymatic domain comprises a non-naturally occurring Clostridial toxin enzymatic domain variant, such as, e.g., a conservative Clostridial toxin enzymatic domain variant, a non-conservative Clostridial toxin enzymatic domain variant, a Clostridial toxin chimeric enzymatic domain, an active Clostridial toxin enzymatic domain fragment, or any combination thereof.

In another embodiment, a Clostridial toxin enzymatic domain comprises a BoNT/A enzymatic domain. In an aspect of this embodiment, a BoNT/A enzymatic domain comprises amino acids 1-448 of SEQ ID NO: 1. In another aspect of this embodiment, a BoNT/A enzymatic domain comprises a naturally occurring BoNT/A enzymatic domain variant, such as, e.g., an enzymatic domain from a BoNT/A isoform or an enzymatic domain from a BoNT/A subtype. In another aspect of this embodiment, a BoNT/A enzymatic domain comprises amino acids 1-448 of a naturally occurring BoNT/A enzymatic domain variant of SEQ ID NO: 1, such as, e.g., amino acids 1-448 of a BoNT/A isoform of SEQ ID NO: 1 or amino acids 1-448 of a BoNT/A subtype of SEQ ID NO: 1. In still another aspect of this embodiment, a BoNT/A enzymatic domain comprises a non-naturally occurring BoNT/A enzymatic domain variant, such as, e.g., a conservative BoNT/A enzymatic domain variant, a non-conservative BoNT/A enzymatic domain variant, a BoNT/A chimeric enzymatic domain, an active BoNT/A enzymatic domain fragment, or any combination thereof. In still another aspect of this embodiment, a BoNT/A enzymatic domain comprises amino acids 1-448 of a non-naturally occurring BoNT/A enzymatic domain variant of SEQ ID NO: 1, such as, e.g., amino acids 1-448 of a conservative BoNT/A enzymatic domain variant of SEQ ID NO: 1, amino acids 1-448 of a non-conservative BoNT/A enzymatic domain variant of SEQ ID NO: 1, amino acids 1-448 of an active BoNT/A enzymatic domain fragment of SEQ ID NO: 1, or any combination thereof.

In other aspects of this embodiment, a BoNT/A enzymatic domain comprises a polypeptide having an amino acid identity of, e.g., at least 70%, at least 75%, at least 80%, at least 85%, at least 90%, at least 95%, or at least 97% to amino acids 1-448 of SEQ ID NO: 1; or at most 70%, at most 75%, at most 80%, at most 85%, at most 90%, at most 95%, or at most 97% to amino acids 1-448 of SEQ ID NO: 1. In yet other aspects of this embodiment, a BoNT/A enzymatic domain comprises a polypeptide having, e.g., at most 1, 2, 3, 4, 5, 6, 7, 8, 9, 10, 20, 30, 40, 50, or 100 non-contiguous amino acid deletions, additions, and/or substitutions relative to amino acids 1-448 of SEQ ID NO: 1; or at most 1, 2, 3, 4, 5, 6, 7, 8, 9, 10, 20, 30, 40, 50, or 100 non-contiguous amino acid deletions, additions, and/or substitutions relative to amino acids 1-448 of SEQ ID NO: 1. In still other aspects of this embodiment, a BoNT/A enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1-448 of SEQ ID NO: 1; or at most 1, 2, 3, 4, 5, 6, 7, 8, 9, 10, 20, 30, 40, 50, or 100 contiguous amino acid deletions, additions, and/or substitutions relative to amino acids 1-448 of SEQ ID NO: 1.

In another embodiment, a Clostridial toxin enzymatic domain comprises a BoNT/B enzymatic domain. In an aspect of this embodiment, a BoNT/B enzymatic domain comprises amino acids 1-441 of SEQ ID NO: 2. In another aspect of this embodiment, a BoNT/B enzymatic domain comprises a naturally occurring BoNT/B enzymatic domain variant, such as, e.g., an enzymatic domain from a BoNT/B isoform or an enzymatic domain from a BoNT/B subtype. In another aspect of this embodiment, a BoNT/B enzymatic domain comprises amino acids 1-441 of a naturally occurring BoNT/B enzymatic domain variant of SEQ ID NO: 2, such as, e.g., amino acids 1-441 of a BoNT/B isoform of SEQ ID NO: 2 or amino acids 1-441 of a BoNT/B subtype of SEQ ID NO: 2. In still another aspect of this embodiment, a BoNT/B enzymatic domain comprises a non-naturally occurring BoNT/B enzymatic domain variant, such as, e.g., a conservative BoNT/B enzymatic domain variant, a non-conservative BoNT/B enzymatic domain variant, a BoNT/B chimeric enzymatic domain, an active BoNT/B enzymatic domain fragment, or any combination thereof. In still another aspect of this embodiment, a BoNT/B enzymatic domain comprises amino acids 1-441 of a non-naturally occurring BoNT/B enzymatic domain variant of SEQ ID NO: 2, such as, e.g., amino acids 1-441 of a conservative BoNT/B enzymatic domain variant of SEQ ID NO: 2, amino acids 1-441 of a non-conservative BoNT/B enzymatic domain variant of SEQ ID NO: 2, amino acids 1-441 of an active BoNT/B enzymatic domain fragment of SEQ ID NO: 2, or any combination thereof.

In other aspects of this embodiment, a BoNT/B enzymatic domain comprises a polypeptide having an amino acid identity of, e.g., at least 70%, at least 75%, at least 80%, at least 85%, at least 90%, at least 95%, or at least 97% to amino acids 1-441 of SEQ ID NO: 2; or at most 70%, at most 75%, at most 80%, at most 85%, at most 90%, at most 95%, or at most 97% to amino acids 1-441 of SEQ ID NO: 2. In yet other aspects of this embodiment, a BoNT/B enzymatic domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 1-441 of SEQ ID NO: 2; or at most 1, 2, 3, 4, 5, 6, 7, 8, 9, 10, 20, 30, 40, 50, or 100 non-contiguous amino acid deletions, additions, and/or substitutions relative to amino acids 1-441 of SEQ ID NO: 2. In still other aspects of this embodiment, a BoNT/B enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1-441 of SEQ ID NO: 2; or at most 1, 2, 3, 4, 5, 6, 7, 8, 9, 10, 20, 30, 40, 50, or 100 contiguous amino acid deletions, additions, and/or substitutions relative to amino acids 1-441 of SEQ ID NO: 2.

In another embodiment, a Clostridial toxin enzymatic domain comprises a BoNT/C1 enzymatic domain. In an aspect of this embodiment, a BoNT/C1 enzymatic domain comprises amino acids 1-449 of SEQ ID NO: 3. In another aspect of this embodiment, a BoNT/C1 enzymatic domain comprises a naturally occurring BoNT/C1 enzymatic domain variant, such as, e.g., an enzymatic domain from a BoNT/C1 isoform or an enzymatic domain from a BoNT/C1 subtype. In another aspect of this embodiment, a BoNT/C1 enzymatic domain comprises amino acids 1-449 of a naturally occurring BoNT/C1 enzymatic domain variant of SEQ ID NO: 3, such as, e.g., amino acids 1-449 of a BoNT/C1 isoform of SEQ ID NO: 3 or amino acids 1-449 of a BoNT/C1 subtype of SEQ ID NO: 3. In still another aspect of this embodiment, a BoNT/C1 enzymatic domain comprises a non-naturally occurring BoNT/C1 enzymatic domain variant, such as, e.g., a conservative BoNT/C1 enzymatic domain variant, a non-conservative BoNT/C1 enzymatic domain variant, a BoNT/C1 chimeric enzymatic domain, an active BoNT/C1 enzymatic domain fragment, or any combination thereof. In still another aspect of this embodiment, a BoNT/C1 enzymatic domain comprises amino acids 1-449 of a non-naturally occurring BoNT/C1 enzymatic domain variant of SEQ ID NO: 3, such as, e.g., amino acids 1-449 of a conservative BoNT/C1 enzymatic domain variant of SEQ ID NO: 3, amino acids 1-449 of a non-conservative BoNT/C1 enzymatic domain variant of SEQ ID NO: 3, amino acids 1-449 of an active BoNT/C1 enzymatic domain fragment of SEQ ID NO: 3, or any combination thereof.

In other aspects of this embodiment, a BoNT/C1 enzymatic domain comprises a polypeptide having an amino acid identity of, e.g., at least 70%, at least 75%, at least 80%, at least 85%, at least 90%, at least 95%, or at least 97% to amino acids 1-449 of SEQ ID NO: 3; or at most 70%, at most 75%, at most 80%, at most 85%, at most 90%, at most 95%, or at most 97% to amino acids 1-449 of SEQ ID NO: 3. In yet other aspects of this embodiment, a BoNT/C1 enzymatic domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 1-449 of SEQ ID NO: 3; or at most 1, 2, 3, 4, 5, 6, 7, 8, 9, 10, 20, 30, 40, 50, or 100 non-contiguous amino acid deletions, additions, and/or substitutions relative to amino acids 1-449 of SEQ ID NO: 3. In other aspects of this embodiment, a BoNT/C1 enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1-449 of SEQ ID NO: 3; or at most 1, 2, 3, 4, 5, 6, 7, 8, 9, 10, 20, 30, 40, 50, or 100 contiguous amino acid deletions, additions, and/or substitutions relative to amino acids 1-449 of SEQ ID NO: 3.

In another embodiment, a Clostridial toxin enzymatic domain comprises a BoNT/D enzymatic domain. In an aspect of this embodiment, a BoNT/D enzymatic domain comprises amino acids 1-445 of SEQ ID NO: 4. In another aspect of this embodiment, a BoNT/D enzymatic domain comprises a naturally occurring BoNT/D enzymatic domain variant, such as, e.g., an enzymatic domain from a BoNT/D isoform or an enzymatic domain from a BoNT/D subtype. In another aspect of this embodiment, a BoNT/D enzymatic domain comprises amino acids 1-445 of a naturally occurring BoNT/D enzymatic domain variant of SEQ ID NO: 4, such as, e.g., amino acids 1-445 of a BoNT/D isoform of SEQ ID NO: 4 or amino acids 1-445 of a BoNT/D subtype of SEQ ID NO: 4. In still another aspect of this embodiment, a BoNT/D enzymatic domain comprises a non-naturally occurring BoNT/D enzymatic domain variant, such as, e.g., a conservative BoNT/D enzymatic domain variant, a non-conservative BoNT/D enzymatic domain variant, a BoNT/D chimeric enzymatic domain, an active BoNT/D enzymatic domain fragment, or any combination thereof. In still another aspect of this embodiment, a BoNT/D enzymatic domain comprises amino acids 1-445 of a non-naturally occurring BoNT/D enzymatic domain variant of SEQ ID NO: 4, such as, e.g., amino acids 1-445 of a conservative BoNT/D enzymatic domain variant of SEQ ID NO: 4, amino acids 1-445 of a non-conservative BoNT/D enzymatic domain variant of SEQ ID NO: 4, amino acids 1-445 of an active BoNT/D enzymatic domain fragment of SEQ ID NO: 4, or any combination thereof.

In other aspects of this embodiment, a BoNT/D enzymatic domain comprises a polypeptide having an amino acid identity of, e.g., at least 70%, at least 75%, at least 80%, at least 85%, at least 90%, at least 95%, or at least 97% to amino acids 1-445 of SEQ ID NO: 4; or at most 70%, at most 75%, at most 80%, at most 85%, at most 90%, at most 95%, or at most 97% to amino acids 1-445 of SEQ ID NO: 4. In yet other aspects of this embodiment, a BoNT/D enzymatic domain comprises a polypeptide having, e.g., at least 1, 2, 3, 4, 5, 6, 7, 8, 9, 10, 20, 30, 40, 50, or 100 non-contiguous amino acid deletions, additions and/or substitutions relative to amino acids 1-445 of SEQ ID NO: 4; or at most 1, 2, 3, 4, 5, 6, 7, 8, 9, 10, 20, 30, 40, 50, or 100 non-contiguous amino acid substitutions relative to amino acids 1-445 of SEQ ID NO: 4. In still other aspects of this embodiment, a BoNT/D enzymatic domain comprises a polypeptide having, e.g., at least 1, 2, 3, 4, 5, 6, 7, 8, 9, 10, 20, 30, 40, 50, or 100 contiguous amino acid deletions, additions and/or substitutions relative to amino acids 1-445 of SEQ ID NO: 4; or at most 1, 2, 3, 4, 5, 6, 7, 8, 9, 10, 20, 30, 40, 50, or 100 contiguous amino acid substitutions relative to amino acids 1-445 of SEQ ID NO: 4.

In another embodiment, a Clostridial toxin enzymatic domain comprises a BoNT/E enzymatic domain. In an aspect of this embodiment, a BoNT/E enzymatic domain comprises amino acids 1-422 of SEQ ID NO: 5. In another aspect of this embodiment, a BoNT/E enzymatic domain comprises a naturally occurring BoNT/E enzymatic domain variant, such as, e.g., an enzymatic domain from a BoNT/E isoform or an enzymatic domain from a BoNT/E subtype. In another aspect of this embodiment, a BoNT/E enzymatic domain comprises amino acids 1-422 of a naturally occurring BoNT/E enzymatic domain variant of SEQ ID NO: 5, such as, e.g., amino acids 1-422 of a BoNT/E isoform of SEQ ID NO: 5 or amino acids 1-422 of a BoNT/E subtype of SEQ ID NO: 5. In still another aspect of this embodiment, a BoNT/E enzymatic domain comprises a non-naturally occurring BoNT/E enzymatic domain variant, such as, e.g., a conservative BoNT/E enzymatic domain variant, a non-conservative BoNT/E enzymatic domain variant, a BoNT/E chimeric enzymatic domain, an active BoNT/E enzymatic domain fragment, or any combination thereof. In still another aspect of this embodiment, a BoNT/E enzymatic domain comprises amino acids 1-422 of a non-naturally occurring BoNT/E enzymatic domain variant of SEQ ID NO: 5, such as, e.g., amino acids 1-422 of a conservative BoNT/E enzymatic domain variant of SEQ ID NO: 5, amino acids 1-422 of a non-conservative BoNT/E enzymatic domain variant of SEQ ID NO: 5, amino acids 1-422 of an active BoNT/E enzymatic domain fragment of SEQ ID NO: 5, or any combination thereof.

In other aspects of this embodiment, a BoNT/E enzymatic domain comprises a polypeptide having an amino acid identity of, e.g., at least 70%, at least 75%, at least 80%, at least 85%, at least 90%, at least 95%, or at least 97% to amino acids 1-422 of SEQ ID NO: 5; or at most 70%, at most 75%, at most 80%, at most 85%, at most 90%, at most 95%, or at most 97% to amino acids 1-422 of SEQ ID NO: 5. In yet other aspects of this embodiment, a BoNT/E enzymatic domain comprises a polypeptide having, e.g., at least 1, 2, 3, 4, 5, 6, 7, 8, 9, 10, 20, 30, 40, 50, or 100 non-contiguous amino acid deletions, additions and/or substitutions relative to amino acids 1-422 of SEQ ID NO: 5; or at most 1, 2, 3, 4, 5, 6, 7, 8, 9, 10, 20, 30, 40, 50, or 100 non-contiguous amino acid deletions, additions and/or substitutions relative to amino acids 1-422 of SEQ ID NO: 5. In still other aspects of this embodiment, a BoNT/E enzymatic domain comprises a polypeptide having, e.g., at least 1, 2, 3, 4, 5, 6, 7, 8, 9, 10, 20, 30, 40, 50, or 100 contiguous amino acid deletions, additions and/or substitutions relative to amino acids 1-422 of SEQ ID NO: 5; or at most 1, 2, 3, 4, 5, 6, 7, 8, 9, 10, 20, 30, 40, 50, or 100 contiguous amino acid deletions, additions and/or substitutions relative to amino acids 1-422 of SEQ ID NO: 5.

In another embodiment, a Clostridial toxin enzymatic domain comprises a BoNT/F enzymatic domain. In an aspect of this embodiment, a BoNT/F enzymatic domain comprises amino acids 1-439 of SEQ ID NO: 6. In another embodiment of this embodiment, a BoNT/F enzymatic domain comprises a naturally occurring BoNT/F enzymatic domain variant, such as, e.g., an enzymatic domain from a BoNT/F isoform or an enzymatic domain from a BoNT/F subtype. In another aspect of this embodiment, a BoNT/F enzymatic domain comprises amino acids 1-439 of a naturally occurring BoNT/F enzymatic domain variant of SEQ ID NO: 6, such as, e.g., amino acids 1-439 of a BoNT/F isoform of SEQ ID NO: 6 or amino acids 1-439 of a BoNT/F subtype of SEQ ID NO: 6. In still another aspect of this embodiment, a BoNT/F enzymatic domain comprises a non-naturally occurring BoNT/F enzymatic domain variant, such as, e.g., a conservative BoNT/F enzymatic domain variant, a non-conservative BoNT/F enzymatic domain variant, a BoNT/F chimeric enzymatic domain, an active BoNT/F enzymatic domain fragment, or any combination thereof. In still another aspect of this embodiment, a BoNT/F enzymatic domain comprises amino acids 1-439 of a non-naturally occurring BoNT/F enzymatic domain variant of SEQ ID NO: 6, such as, e.g., amino acids 1-439 of a conservative BoNT/F enzymatic domain variant of SEQ ID NO: 6, amino acids 1-439 of a non-conservative BoNT/F enzymatic domain variant of SEQ ID NO: 6, amino acids 1-439 of an active BoNT/F enzymatic domain fragment of SEQ ID NO: 6, or any combination thereof.

In other aspects of this embodiment, a BoNT/F enzymatic domain comprises a polypeptide having an amino acid identity of, e.g., at least 70%, at least 75%, at least 80%, at least 85%, at least 90%, at least 95%, or at least 97% to amino acids 1-439 of SEQ ID NO: 6; or at most 70%, at most 75%, at most 80%, at most 85%, at most 90%, at most 95%, or at most 97% to amino acids 1-439 of SEQ ID NO: 6. In yet other aspects of this embodiment, a BoNT/F enzymatic domain comprises a polypeptide having, e.g., at least 1, 2, 3, 4, 5, 6, 7, 8, 9, 10, 20, 30, 40, 50, or 100 non-contiguous amino acid deletions, additions and/or substitutions relative to amino acids 1-439 of SEQ ID NO: 6; or at most 1, 2, 3, 4, 5, 6, 7, 8, 9, 10, 20, 30, 40, 50, or 100 non-contiguous amino acid deletions, additions and/or substitutions relative to amino acids 1-439 of SEQ ID NO: 6. In still other aspects of this embodiment, a BoNT/F enzymatic domain comprises a polypeptide having, e.g., at least 1, 2, 3, 4, 5, 6, 7, 8, 9, 10, 20, 30, 40, 50, or 100 contiguous amino acid deletions, additions and/or substitutions relative to amino acids 1-439 of SEQ ID NO: 6; or at most 1, 2, 3, 4, 5, 6, 7, 8, 9, 10, 20, 30, 40, 50, or 100 contiguous amino acid deletions, additions and/or substitutions relative to amino acids 1-439 of SEQ ID NO: 6.

In another embodiment, a Clostridial toxin enzymatic domain comprises a BoNT/G enzymatic domain. In an aspect of this embodiment, a BoNT/G enzymatic domain comprises amino acids 1-446 of SEQ ID NO: 7. In another aspect of this embodiment, a BoNT/G enzymatic domain comprises a naturally occurring BoNT/G enzymatic domain variant, such as, e.g., an enzymatic domain from a BoNT/G isoform or an enzymatic domain from a BoNT/G subtype. In another aspect of this embodiment, a BoNT/G enzymatic domain comprises amino acids 1-446 of a naturally occurring BoNT/G enzymatic domain variant of SEQ ID NO: 7, such as, e.g., amino acids 1-446 of a BoNT/G isoform of SEQ ID NO: 7 or amino acids 1-446 of a BoNT/G subtype of SEQ ID NO: 7. In still another aspect of this embodiment, a BoNT/G enzymatic domain comprises a non-naturally occurring BoNT/G enzymatic domain variant, such as, e.g., a conservative BoNT/G enzymatic domain variant, a non-conservative BoNT/G enzymatic domain variant, a BoNT/G chimeric enzymatic domain, an active BoNT/G enzymatic domain fragment, or any combination thereof. In still another aspect of this embodiment, a BoNT/G enzymatic domain comprises amino acids 1-446 of a non-naturally occurring BoNT/G enzymatic domain variant of SEQ ID NO: 7, such as, e.g., amino acids 1-446 of a conservative BoNT/G enzymatic domain variant of SEQ ID NO: 7, amino acids 1-446 of a non-conservative BoNT/G enzymatic domain variant of SEQ ID NO: 7, amino acids 1-446 of an active BoNT/G enzymatic domain fragment of SEQ ID NO: 7, or any combination thereof.

In other aspects of this embodiment, a BoNT/G enzymatic domain comprises a polypeptide having an amino acid identity of, e.g., at least 70%, at least 75%, at least 80%, at least 85%, at least 90%, at least 95%, or at least 97% to amino acids 1-446 of SEQ ID NO: 7; or at most 70%, at most 75%, at most 80%, at most 85%, at most 90%, at most 95%, or at most 97% to amino acids 1-446 of SEQ ID NO: 7. In yet other aspects of this embodiment, a BoNT/G enzymatic domain comprises a polypeptide having, e.g., at least 1, 2, 3, 4, 5, 6, 7, 8, 9, 10, 20, 30, 40, 50, or 100 non-contiguous amino acid deletions, additions and/or substitutions relative to amino acids 1-446 of SEQ ID NO: 7; or at most 1, 2, 3, 4, 5, 6, 7, 8, 9, 10, 20, 30, 40, 50, or 100 non-contiguous amino acid deletions, additions and/or substitutions relative to amino acids 1-446 of SEQ ID NO: 7. In still other aspects of this embodiment, a BoNT/G enzymatic domain comprises a polypeptide having, e.g., at least 1, 2, 3, 4, 5, 6, 7, 8, 9, 10, 20, 30, 40, 50, or 100 contiguous amino acid deletions, additions and/or substitutions relative to amino acids 1-446 of SEQ ID NO: 7; or at most 1, 2, 3, 4, 5, 6, 7, 8, 9, 10, 20, 30, 40, 50, or 100 contiguous amino acid deletions, additions and/or substitutions relative to amino acids 1-446 of SEQ ID NO: 7.

In another embodiment, a Clostridial toxin enzymatic domain comprises a TeNT enzymatic domain. In an aspect of this embodiment, a TeNT enzymatic domain comprises amino acids 1-457 of SEQ ID NO: 8. In another aspect of this embodiment, a TeNT enzymatic domain comprises a naturally occurring TeNT enzymatic domain variant, such as, e.g., an enzymatic domain from a TeNT isoform or an enzymatic domain from a TeNT subtype. In another aspect of this embodiment, a TeNT enzymatic domain comprises amino acids 1-457 of a naturally occurring TeNT enzymatic domain variant of SEQ ID NO: 8, such as, e.g., amino acids 1-457 of a TeNT isoform of SEQ ID NO: 8 or amino acids 1-457 of a TeNT subtype of SEQ ID NO: 8. In still another aspect of this embodiment, a TeNT enzymatic domain comprises a non-naturally occurring TeNT enzymatic domain variant, such as, e.g., a conservative TeNT enzymatic domain variant, a non-conservative TeNT enzymatic domain variant, a TeNT chimeric enzymatic domain, an active TeNT enzymatic domain fragment, or any combination thereof. In still another aspect of this embodiment, a TeNT enzymatic domain comprises amino acids 1-457 of a non-naturally occurring TeNT enzymatic domain variant of SEQ ID NO: 8, such as, e.g., amino acids 1-457 of a conservative TeNT enzymatic domain variant of SEQ ID NO: 8, amino acids 1-457 of a non-conservative TeNT enzymatic domain variant of SEQ ID NO: 8, amino acids 1-457 of an active TeNT enzymatic domain fragment of SEQ ID NO: 8, or any combination thereof.

In other aspects of this embodiment, a TeNT enzymatic domain comprises a polypeptide having an amino acid identity of, e.g., at least 70%, at least 75%, at least 80%, at least 85%, at least 90%, at least 95%, or at least 97% to amino acids 1-457 of SEQ ID NO: 8; or at most 70%, at most 75%, at most 80%, at most 85%, at most 90%, at most 95%, or at most 97% to amino acids 1-457 of SEQ ID NO: 8. In yet other aspects of this embodiment, a TeNT enzymatic domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 1-457 of SEQ ID NO: 8; or at most 1, 2, 3, 4, 5, 6, 7, 8, 9, 10, 20, 30, 40, 50, or 100 non-contiguous amino acid deletions, additions, and/or substitutions relative to amino acids 1-457 of SEQ ID NO: 8. In still other aspects of this embodiment, a TeNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1-457 of SEQ ID NO: 8; at most 1, 2, 3, 4, 5, 6, 7, 8, 9, 10, 20, 30, 40, 50, or 100 contiguous amino acid substitutions relative to amino acids 1-457 of SEQ ID NO: 8.

In another embodiment, a Clostridial toxin enzymatic domain comprises a BaNT enzymatic domain. In an aspect of this embodiment, a BaNT enzymatic domain comprises amino acids 1-431 of SEQ ID NO: 9. In another aspect of this embodiment, a BaNT enzymatic domain comprises a naturally occurring BaNT enzymatic domain variant, such as, e.g., an enzymatic domain from a BaNT isoform or an enzymatic domain from a BaNT subtype. In another aspect of this embodiment, a BaNT enzymatic domain comprises amino acids 1-431 of a naturally occurring BaNT enzymatic domain variant of SEQ ID NO: 9, such as, e.g., amino acids 1-431 of a BaNT isoform of SEQ ID NO: 9 or amino acids 1-431 of a BaNT subtype of SEQ ID NO: 9. In still another aspect of this embodiment, a BaNT enzymatic domain comprises a non-naturally occurring BaNT enzymatic domain variant, such as, e.g., a conservative BaNT enzymatic domain variant, a non-conservative BaNT enzymatic domain variant, a BaNT chimeric enzymatic domain, an active BaNT enzymatic domain fragment, or any combination thereof. In still another aspect of this embodiment, a BaNT enzymatic domain comprises amino acids 1-431 of a non-naturally occurring BaNT enzymatic domain variant of SEQ ID NO: 9, such as, e.g., amino acids 1-431 of a conservative BaNT enzymatic domain variant of SEQ ID NO: 9, amino acids 1-431 of a non-conservative BaNT enzymatic domain variant of SEQ ID NO: 9, amino acids 1-431 of an active BaNT enzymatic domain fragment of SEQ ID NO: 9, or any combination thereof.

In other aspects of this embodiment, a BaNT enzymatic domain comprises a polypeptide having an amino acid identity of, e.g., at least 70%, at least 75%, at least 80%, at least 85%, at least 90%, at least 95%, or at least 97% to amino acids 1-431 of SEQ ID NO: 9; or at most 70%, at most 75%, at most 80%, at most 85%, at most 90%, at most 95%, or at most 97% to amino acids 1-431 of SEQ ID NO: 9. In yet other aspects of this embodiment, a BaNT enzymatic domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 1-431 of SEQ ID NO: 9; or at most 1, 2, 3, 4, 5, 6, 7, 8, 9, 10, 20, 30, 40, 50, or 100 non-contiguous amino acid deletions, additions, and/or substitutions relative to amino acids 1-431 of SEQ ID NO: 9. In still other aspects of this embodiment, a BaNT enzymatic domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 1-431 of SEQ ID NO: 9; at most 1, 2, 3, 4, 5, 6, 7, 8, 9, 10, 20, 30, 40, 50, or 100 contiguous amino acid deletions, additions, and/or substitutions relative to amino acids 1-431 of SEQ ID NO: 9.

In another embodiment, a Clostridial toxin enzymatic domain comprises a BuNT enzymatic domain. In an aspect of this embodiment, a BuNT enzymatic domain comprises amino acids 1-422 of SEQ ID NO: 10. In another aspect of this embodiment, a BuNT enzymatic domain comprises a naturally occurring BuNT enzymatic domain variant, such as, e.g., an enzymatic domain from a BuNT isoform or an enzymatic domain from a BuNT subtype. In another aspect of this embodiment, a BuNT enzymatic domain comprises amino acids 1-422 of a naturally occurring BuNT enzymatic domain variant of SEQ ID NO: 10, such as, e.g., amino acids 1-422 of a BuNT isoform of SEQ ID NO: 10 or amino acids 1-422 of a BuNT subtype of SEQ ID NO: 10. In still another aspect of this embodiment, a BuNT enzymatic domain comprises a non-naturally occurring BuNT enzymatic domain variant, such as, e.g., a conservative BuNT enzymatic domain variant, a non-conservative BuNT enzymatic domain variant, a BuNT chimeric enzymatic domain, an active BuNT enzymatic domain fragment, or any combination thereof. In still another aspect of this embodiment, a BuNT enzymatic domain comprises amino acids 1-422 of a non-naturally occurring BuNT enzymatic domain variant of SEQ ID NO: 10, such as, e.g., amino acids 1-422 of a conservative BuNT enzymatic domain variant of SEQ ID NO: 10, amino acids 1-422 of a non-conservative BuNT enzymatic domain variant of SEQ ID NO: 10, amino acids 1-422 of an active BuNT enzymatic domain fragment of SEQ ID NO: 10, or any combination thereof.

In other aspects of this embodiment, a BuNT enzymatic domain comprises a polypeptide having an amino acid identity of, e.g., at least 70%, at least 75%, at least 80%, at least 85%, at least 90%, at least 95%, or at least 97% to amino acids 1-422 of SEQ ID NO: 10; or at most 70%, at most 75%, at most 80%, at most 85%, at most 90%, at most 95%, or at most 97% to amino acids 1-422 of SEQ ID NO: 10. In yet other aspects of this embodiment, a BuNT enzymatic domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 1-422 of SEQ ID NO: 1; or at most 1, 2, 3, 4, 5, 6, 7, 8, 9, 10, 20, 30, 40, 50, or 100 non-contiguous amino acid deletions, additions, and/or substitutions relative to amino acids 1-422 of SEQ ID NO: 10. In still other aspects of this embodiment, a BuNT enzymatic domain comprises a polypeptide having, e.g., at least 1, 2, 3, 4, 5, 6, 7, 8, 9, 10, 20, 30, 40, 50, 100 or 200 contiguous amino acid deletions, additions, and/or substitutions relative to amino acids 1-422 of SEQ ID NO: 10; or at most 1, 2, 3, 4, 5, 6, 7, 8, 9, 10, 20, 30, 40, 50, 100 or 200 contiguous amino acid deletions, additions, and/or substitutions relative to amino acids 1-422 of SEQ ID NO: 10.

The "translocation domain" comprises a portion of a Clostridial neurotoxin heavy chain having a translocation activity. By "translocation" is meant the ability to facilitate the transport of a polypeptide through a vesicular membrane, thereby exposing some or all of the polypeptide to the cytoplasm. In the various botulinum neurotoxins translocation is thought to involve an allosteric conformational change of the heavy chain caused by a decrease in pH within the endosome. This conformational change appears to involve and be mediated by the N terminal half of the heavy chain and to result in the formation of pores in the vesicular membrane; this change permits the movement of the proteolytic light chain from within the endosomal vesicle into the cytoplasm. See e.g., Lacy, et al., *Nature Struct. Biol.* 5:898-902 (October 1998).

The amino acid sequence of the translocation-mediating portion of the botulinum neurotoxin heavy chain is known to those of skill in the art; additionally, those amino acid residues within this portion that are known to be essential for conferring the translocation activity are also known. It would therefore be well within the ability of one of ordinary skill in the art, for example, to employ the naturally occurring N-terminal peptide half of the heavy chain of any of the various *Clostridium tetanus* or *Clostridium botulinum* neurotoxin subtypes as a translocation domain, or to design an analogous translocation domain by aligning the primary sequences of the N-terminal halves of the various heavy chains and selecting a consensus primary translocation sequence based on conserved amino acid, polarity, steric and hydrophobicity characteristics between the sequences.

In another aspect of the invention, a TVEMP comprises, in part, a Clostridial toxin translocation domain. As used herein, the term "Clostridial toxin translocation domain" refers to any Clostridial toxin polypeptide that can execute the translocation step of the intoxication process that mediates Clostridial toxin light chain translocation. Thus, a Clostridial toxin translocation domain facilitates the movement of a Clostridial toxin light chain across a membrane and encompasses the movement of a Clostridial toxin light chain through the membrane an intracellular vesicle into the cytoplasm of a cell. Non-limiting examples of a Clostridial toxin translocation domain include, e.g., a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and a BuNT translocation domain. Other non-limiting examples of a Clostridial toxin translocation domain include, e.g., amino acids 449-873 of SEQ ID NO: 1, amino acids 442-860 of SEQ ID NO: 2, amino acids 450-868 of SEQ ID NO: 3, amino acids 446-864 of SEQ ID NO: 4, amino acids 423-847 of SEQ ID NO: 5, amino acids 440-866 of SEQ ID NO: 6, amino acids 447-865 of SEQ ID NO: 7, amino acids 458-881 of SEQ ID NO: 8, amino acids 432-857 of SEQ ID NO: 9, and amino acids 423-847 of SEQ ID NO: 10.

A Clostridial toxin translocation domain includes, without limitation, naturally occurring Clostridial toxin translocation domain variants, such as, e.g., Clostridial toxin translocation domain isoforms and Clostridial toxin translocation domain subtypes; non-naturally occurring Clostridial toxin translocation domain variants, such as, e.g., conservative Clostridial toxin translocation domain variants, non-conservative Clostridial toxin translocation domain variants, Clostridial toxin translocation domain chimerics, active Clostridial toxin translocation domain fragments thereof, or any combination thereof.

As used herein, the term "Clostridial toxin translocation domain variant," whether naturally-occurring or non-naturally-occurring, refers to a Clostridial toxin translocation domain that has at least one amino acid change from the corresponding region of the disclosed reference sequences (Table 1) and can be described in percent identity to the corresponding region of that reference sequence. Unless expressly indicated, Clostridial toxin translocation domain variants useful to practice disclosed embodiments are variants that execute the translocation step of the intoxication process that mediates Clostridial toxin light chain translocation. As non-limiting examples, a BoNT/A translocation domain variant comprising amino acids 449-873 of SEQ ID NO: 1 will have at least one amino acid difference, such as, e.g., an amino acid substitution, deletion or addition, as compared to the amino acid region 449-873 of SEQ ID NO: 1; a BoNT/B translocation domain variant comprising amino acids 442-860 of SEQ ID NO: 2 will have at least one amino acid difference, such as, e.g., an amino acid substitution, deletion or addition, as compared to the amino acid region 442-860 of SEQ ID NO: 2; a BoNT/C1 translocation domain variant comprising amino acids 450-868 of SEQ ID NO: 3 will have at least one amino acid difference, such as, e.g., an amino acid substitution, deletion or addition, as compared to the amino acid region 450-868 of SEQ ID NO: 3; a BoNT/D translocation domain variant comprising amino acids 446-864 of SEQ ID NO: 4 will have at least one amino acid difference, such as, e.g., an amino acid substitution, deletion or addition, as compared to the amino acid region 446-864 of SEQ ID NO: 4; a BoNT/E translocation domain variant comprising amino acids 423-847 of SEQ ID NO: 5 will have at least one amino acid difference, such as, e.g., an amino acid substitution, deletion or addition, as compared to the amino acid region 423-847 of SEQ ID NO: 5; a BoNT/F translocation domain variant comprising amino acids 440-866 of SEQ ID NO: 6 will have at least one amino acid difference, such as, e.g., an amino acid substitution, deletion or addition, as compared to the amino acid region 440-866 of SEQ ID NO: 6; a BoNT/G translocation domain variant comprising amino acids 447-865 of SEQ ID NO: 7 will have at least one amino acid difference, such as, e.g., an amino acid substitution, deletion or addition, as compared to the amino acid region 447-865 of SEQ ID NO: 7; a TeNT translocation domain variant comprising amino acids 458-881 of SEQ ID NO: 8 will have at least one amino acid difference, such as, e.g., an amino acid substitution, deletion or addition, as compared to the amino acid region 458-881 of SEQ ID NO: 8; a BaNT translocation domain variant comprising amino acids 432-857 of SEQ ID NO: 9 will have at least one amino acid difference, such as, e.g., an amino acid substitution, deletion or addition, as compared to the amino acid region 432-857 of SEQ ID NO: 9; and a BuNT translocation domain variant comprising amino acids 423-847 of SEQ ID NO: 10 will have at least one amino acid difference, such as, e.g., an amino acid substitution, deletion or addition, as compared to the amino acid region 423-847 of SEQ ID NO: 10.

It is recognized by those of skill in the art that within each serotype of Clostridial toxin there can be naturally occurring Clostridial toxin translocation domain variants that differ somewhat in their amino acid sequence, and also in the nucleic acids encoding these proteins. For example, there are presently five BoNT/A subtypes, BoNT/A1, BoNT/A2, BoNT/A3, BoNT/A4, and BoNT/A5, with specific translocation domain subtypes showing approximately 87% amino acid identity when compared to another BoNT/A translocation domain subtype. As used herein, the term "naturally occurring Clostridial toxin translocation domain variant" refers to any Clostridial toxin translocation domain produced by a naturally-occurring process, including, without limitation, Clostridial toxin translocation domain isoforms produced from alternatively-spliced transcripts, Clostridial toxin translocation domain isoforms produced by spontaneous mutation and Clostridial toxin translocation domain subtypes. A naturally occurring Clostridial toxin translocation domain variant can function in substantially the same manner as the reference Clostridial toxin translocation domain on which the naturally occurring Clostridial toxin translocation domain variant is based, and can be substituted for the reference Clostridial toxin translocation domain in any aspect of the present invention.

A non-limiting example of a naturally occurring Clostridial toxin translocation domain variant is a Clostridial toxin translocation domain isoform such as, e.g., a BoNT/A translocation domain isoform, a BoNT/B translocation domain isoform, a BoNT/C1 translocation domain isoform, a BoNT/D translocation domain isoform, a BoNT/E translocation domain isoform, a BoNT/F translocation domain isoform, a BoNT/G translocation domain isoform, a TeNT translocation domain isoform, a BaNT translocation domain isoform, and a BuNT translocation domain isoform. Another non-limiting example of a naturally occurring Clostridial toxin translocation domain variant is a Clostridial toxin translocation domain subtype such as, e.g., a translocation domain from subtype BoNT/A1, BoNT/A2, BoNT/A3, BoNT/A4, and BoNT/A5; a translocation domain from subtype BoNT/B1, BoNT/B2, BoNT/B bivalent and BoNT/B nonproteolytic; a translocation domain from subtype BoNT/C1-1 and BoNT/C1-2; a translocation domain from subtype BoNT/E1, BoNT/E2 and BoNT/E3; and a translocation domain from subtype BoNT/F1, BoNT/F2, BoNT/F3 and BoNT/F4.

As used herein, the term "non-naturally occurring Clostridial toxin translocation domain variant" refers to any Clostridial toxin translocation domain produced with the aid of human manipulation, including, without limitation, Clostridial toxin translocation domains produced by genetic engineering using random mutagenesis or rational design and Clostridial toxin translocation domains produced by chemical synthesis. Non-limiting examples of non-naturally occurring Clostridial toxin translocation domain variants include, e.g., conservative Clostridial toxin translocation domain variants, non-conservative Clostridial toxin translocation domain variants, Clostridial toxin translocation domain chimeric variants and active Clostridial toxin translocation domain fragments.

As used herein, the term "conservative Clostridial toxin translocation domain variant" refers to a Clostridial toxin translocation domain that has at least one amino acid substituted by another amino acid or an amino acid analog that has at least one property similar to that of the original amino acid from the reference Clostridial toxin translocation domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin translocation domain variant can function in substantially the same manner as the reference Clostridial toxin translocation domain on which the conservative Clostridial toxin translocation domain variant is based, and can be substituted for the reference Clostridial toxin translocation domain in any aspect of the present invention. Non-limiting examples of a conservative Clostridial toxin translocation domain variant include, e.g., conservative BoNT/A translocation domain variants, conservative BoNT/B translocation domain variants, conservative BoNT/C1 translocation domain variants, conservative BoNT/D translocation domain variants, conservative BoNT/E translocation domain variants, conservative BoNT/F translocation domain variants, conservative BoNT/G translocation domain variants, conservative TeNT translocation domain variants, conservative BaNT translocation domain variants, and conservative BuNT translocation domain variants.

As used herein, the term "non-conservative Clostridial toxin translocation domain variant" refers to a Clostridial toxin translocation domain in which 1) at least one amino acid is deleted from the reference Clostridial toxin translocation domain on which the non-conservative Clostridial toxin translocation domain variant is based; 2) at least one amino acid added to the reference Clostridial toxin translocation domain on which the non-conservative Clostridial toxin translocation domain is based; or 3) at least one amino acid is substituted by another amino acid or an amino acid analog that does not share any property similar to that of the original amino acid from the reference Clostridial toxin translocation domain sequence (Table 1). A non-conservative Clostridial toxin translocation domain variant can function in substantially the same manner as the reference Clostridial toxin translocation domain on which the non-conservative Clostridial toxin translocation domain variant is based, and can be substituted for the reference Clostridial toxin translocation domain in any aspect of the present invention. Non-limiting examples of a non-conservative Clostridial toxin translocation domain variant include, e.g., non-conservative BoNT/A translocation domain variants, non-conservative BoNT/B translocation domain variants, non-conservative BoNT/C1 translocation domain variants, non-conservative BoNT/D translocation domain variants, non-conservative BoNT/E translocation domain variants, non-conservative BoNT/F translocation domain variants, non-conservative BoNT/G translocation domain variants, and non-conservative TeNT translocation domain variants, non-conservative BaNT translocation domain variants, and non-conservative BuNT translocation domain variants.

As used herein, the term "Clostridial toxin translocation domain chimeric" refers to a polypeptide comprising at least a portion of a Clostridial toxin translocation domain and at least a portion of at least one other polypeptide to form a toxin translocation domain with at least one property different from the reference Clostridial toxin translocation domains of Table 1, with the proviso that this Clostridial toxin translocation domain chimeric is still capable of specifically targeting the core components of the neurotransmitter release apparatus and thus participate in executing the overall cellular mechanism whereby a Clostridial toxin proteolytically cleaves a substrate.

As used herein, the term "active Clostridial toxin translocation domain fragment" refers to any of a variety of Clostridial toxin fragments comprising the translocation domain can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The translocation domains from the heavy chains of Clostridial toxins are approximately 410-430 amino acids in length and comprise a translocation domain (Table 1). Research has shown that the entire length of a translocation domain from a Clostridial toxin heavy chain is not necessary for the translocating activity of the translocation domain. Thus, aspects of this embodiment can include Clostridial toxin translocation domains comprising a translocation domain having a length of, e.g., at least 350 amino acids, at least 375 amino acids, at least 400 amino acids or at least 425 amino acids. Other aspects of this embodiment can include Clostridial toxin translocation domains comprising translocation domain having a length of, e.g., at most 350 amino acids, at most 375 amino acids, at most 400 amino acids or at most 425 amino acids.

Any of a variety of sequence alignment methods can be used to determine percent identity of naturally-occurring Clostridial toxin translocation domain variants and non-naturally-occurring Clostridial toxin translocation domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a TVEMP disclosed in the present specification comprises a Clostridial toxin translocation domain. In an aspect of this embodiment, a Clostridial toxin translocation domain comprises a naturally occurring Clostridial toxin translocation domain variant, such as, e.g., a Clostridial toxin translocation domain isoform or a Clostridial toxin translocation domain subtype. In another aspect of this embodiment, a Clostridial toxin translocation domain comprises a non-naturally occurring Clostridial toxin translocation domain variant, such as, e.g., a conservative Clostridial toxin translocation domain variant, a non-conservative Clostridial toxin translocation domain variant, a Clostridial toxin chimeric translocation domain, an active Clostridial toxin translocation domain fragment, or any combination thereof.

In another embodiment, a Clostridial toxin translocation domain comprises a BoNT/A translocation domain. In an aspect of this embodiment, a BoNT/A translocation domain comprises amino acids 449-873 of SEQ ID NO: 1. In another aspect of this embodiment, a BoNT/A translocation domain comprises a naturally occurring BoNT/A translocation domain variant, such as, e.g., a translocation domain from a BoNT/A isoform or a translocation domain from a BoNT/A subtype. In another aspect of this embodiment, a BoNT/A translocation domain comprises amino acids 449-873 of a naturally occurring BoNT/A translocation domain variant of SEQ ID NO: 1, such as, e.g., amino acids 449-873 of a BoNT/A isoform of SEQ ID NO: 1 or amino acids 449-873 of a BoNT/A subtype of SEQ ID NO: 1. In still another aspect of this embodiment, a BoNT/A translocation domain comprises a non-naturally occurring BoNT/A translocation domain variant, such as, e.g., a conservative BoNT/A translocation domain variant, a non-conservative BoNT/A translocation domain variant, a BoNT/A chimeric translocation domain, an active BoNT/A translocation domain fragment, or any combination thereof. In still another aspect of this embodiment, a BoNT/A translocation domain comprises amino acids 449-

873 of a non-naturally occurring BoNT/A translocation domain variant of SEQ ID NO: 1, such as, e.g., amino acids 449-873 of a conservative BoNT/A translocation domain variant of SEQ ID NO: 1, amino acids 449-873 of a non-conservative BoNT/A translocation domain variant of SEQ ID NO: 1, amino acids 449-873 of an active BoNT/A translocation domain fragment of SEQ ID NO: 1, or any combination thereof.

In other aspects of this embodiment, a BoNT/A translocation domain comprises a polypeptide having an amino acid identity of, e.g., at least 70%, at least 75%, at least 80%, at least 85%, at least 90%, at least 95%, or at least 97% to amino acids 449-873 of SEQ ID NO: 1; or at most 70%, at most 75%, at most 80%, at most 85%, at most 90%, at most 95%, or at most 97% to amino acids 449-873 of SEQ ID NO: 1. In yet other aspects of this embodiment, a BoNT/A translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 449-873 of SEQ ID NO: 1; at most 1, 2, 3, 4, 5, 6, 7, 8, 9, 10, 20, 30, 40, 50, or 100 non-contiguous amino acid deletions, additions, and/or substitutions relative to amino acids 449-873 of SEQ ID NO: 1. In still other aspects of this embodiment, a BoNT/A translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 449-873 of SEQ ID NO: 1; at most 1, 2, 3, 4, 5, 6, 7, 8, 9, 10, 20, 30, 40, 50, 100 or 200 contiguous amino acid deletions, additions, and/or substitutions relative to amino acids 449-873 of SEQ ID NO: 1.

In another embodiment, a Clostridial toxin translocation domain comprises a BoNT/B translocation domain. In an aspect of this embodiment, a BoNT/B translocation domain comprises amino acids 442-860 of SEQ ID NO: 2. In another aspect of this embodiment, a BoNT/B translocation domain comprises a naturally occurring BoNT/B translocation domain variant, such as, e.g., a translocation domain from a BoNT/B isoform or a translocation domain from a BoNT/B subtype. In another aspect of this embodiment, a BoNT/B translocation domain comprises amino acids 442-860 of a naturally occurring BoNT/B translocation domain variant of SEQ ID NO: 2, such as, e.g., amino acids 442-860 of a BoNT/B isoform of SEQ ID NO: 2 or amino acids 442-860 of a BoNT/B subtype of SEQ ID NO: 2. In still another aspect of this embodiment, a BoNT/B translocation domain comprises a non-naturally occurring BoNT/B translocation domain variant, such as, e.g., a conservative BoNT/B translocation domain variant, a non-conservative BoNT/B translocation domain variant, a BoNT/B chimeric translocation domain, an active BoNT/B translocation domain fragment, or any combination thereof. In still another aspect of this embodiment, a BoNT/B translocation domain comprises amino acids 442-860 of a non-naturally occurring BoNT/B translocation domain variant of SEQ ID NO: 2, such as, e.g., amino acids 442-860 of a conservative BoNT/B translocation domain variant of SEQ ID NO: 2, amino acids 442-860 of a non-conservative BoNT/B translocation domain variant of SEQ ID NO: 2, amino acids 442-860 of an active BoNT/B translocation domain fragment of SEQ ID NO: 2, or any combination thereof.

In other aspects of this embodiment, a BoNT/B translocation domain comprises a polypeptide having an amino acid identity of, e.g., at least 70%, at least 75%, at least 80%, at least 85%, at least 90%, at least 95%, or at least 97% to amino acids 442-860 of SEQ ID NO: 2; or at most 70%, at most 75%, at most 80%, at most 85%, at most 90%, at most 95%, or at most 97% to amino acids 442-860 of SEQ ID NO: 2. In yet other aspects of this embodiment, a BoNT/B translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 442-860 of SEQ ID NO: 2; or at most 1, 2, 3, 4, 5, 6, 7, 8, 9, 10, 20, 30, 40, 50, 100 or 200 non-contiguous amino acid deletions, additions, and/or substitutions relative to amino acids 442-860 of SEQ ID NO: 2. In still other aspects of this embodiment, a BoNT/B translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 442-860 of SEQ ID NO: 2; or at most 1, 2, 3, 4, 5, 6, 7, 8, 9, 10, 20, 30, 40, 50, or 100 contiguous amino acid deletions, additions, and/or substitutions relative to amino acids 442-860 of SEQ ID NO: 2.

In another embodiment, a Clostridial toxin translocation domain comprises a BoNT/C1 translocation domain. In an aspect of this embodiment, a BoNT/C1 translocation domain comprises amino acids 450-868 of SEQ ID NO: 3. In another aspect of this embodiment, a BoNT/C1 translocation domain comprises a naturally occurring BoNT/C1 translocation domain variant, such as, e.g., a translocation domain from a BoNT/C1 isoform or a translocation domain from a BoNT/C1 subtype. In another aspect of this embodiment, a BoNT/C1 translocation domain comprises amino acids 450-868 of a naturally occurring BoNT/C1 translocation domain variant of SEQ ID NO: 3, such as, e.g., amino acids 450-868 of a BoNT/C1 isoform of SEQ ID NO: 3 or amino acids 450-868 of a BoNT/C1 subtype of SEQ ID NO: 3. In still another aspect of this embodiment, a BoNT/C1 translocation domain comprises a non-naturally occurring BoNT/C1 translocation domain variant, such as, e.g., a conservative BoNT/C1 translocation domain variant, a non-conservative BoNT/C1 translocation domain variant, a BoNT/C1 chimeric translocation domain, an active BoNT/C1 translocation domain fragment, or any combination thereof. In still another aspect of this embodiment, a BoNT/C1 translocation domain comprises amino acids 450-868 of a non-naturally occurring BoNT/C1 translocation domain variant of SEQ ID NO: 3, such as, e.g., amino acids 450-868 of a conservative BoNT/C1 translocation domain variant of SEQ ID NO: 3, amino acids 450-868 of a non-conservative BoNT/C1 translocation domain variant of SEQ ID NO: 3, amino acids 450-868 of an active BoNT/C1 translocation domain fragment of SEQ ID NO: 3, or any combination thereof.

In other aspects of this embodiment, a BoNT/C1 translocation domain comprises a polypeptide having an amino acid identity of, e.g., at least 70%, at least 75%, at least 80%, at least 85%, at least 90%, at least 95%, or at least 97% to amino acids 450-868 of SEQ ID NO: 3; or at most 70%, at most 75%, at most 80%, at most 85%, at most 90%, at most 95%, or at most 97% to amino acids 450-868 of SEQ ID NO: 3. In yet other aspects of this embodiment, a BoNT/C1 translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 450-868 of SEQ ID NO: 3; or at most 1, 2, 3, 4, 5, 6, 7, 8, 9, 10, 20, 30, 40, 50, or 100 non-contiguous amino acid deletions, additions, and/or substitutions relative to amino acids 450-868 of SEQ ID NO: 3. In still other aspects of this embodiment, a BoNT/C1 translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 450-868 of SEQ ID NO: 3; or at most 1, 2, 3, 4, 5, 6, 7, 8, 9, 10, 20, 30, 40, 50, or 100 contiguous amino acid deletions, additions, and/or substitutions relative to amino acids 450-868 of SEQ ID NO: 3.

In another embodiment, a Clostridial toxin translocation domain comprises a BoNT/D translocation domain. In an aspect of this embodiment, a BoNT/D translocation domain comprises amino acids 446-864 of SEQ ID NO: 4. In another aspect of this embodiment, a BoNT/D translocation domain comprises a naturally occurring BoNT/D translocation domain variant, such as, e.g., a translocation domain from a BoNT/D isoform or a translocation domain from a BoNT/D subtype. In another aspect of this embodiment, a BoNT/D translocation domain comprises amino acids 446-864 of a naturally occurring BoNT/D translocation domain variant of SEQ ID NO: 4, such as, e.g., amino acids 446-864 of a BoNT/D isoform of SEQ ID NO: 4 or amino acids 446-864 of a BoNT/D subtype of SEQ ID NO: 4. In still another aspect of this embodiment, a BoNT/D translocation domain comprises a non-naturally occurring BoNT/D translocation domain variant, such as, e.g., a conservative BoNT/D translocation domain variant, a non-conservative BoNT/D translocation domain variant, a BoNT/D chimeric translocation domain, an active BoNT/D translocation domain fragment, or any combination thereof. In still another aspect of this embodiment, a BoNT/D translocation domain comprises amino acids 446-864 of a non-naturally occurring BoNT/D translocation domain variant of SEQ ID NO: 4, such as, e.g., amino acids 446-864 of a conservative BoNT/D translocation domain variant of SEQ ID NO: 4, amino acids 446-864 of a non-conservative BoNT/D translocation domain variant of SEQ ID NO: 4, amino acids 446-864 of an active BoNT/D translocation domain fragment of SEQ ID NO: 4, or any combination thereof.

In other aspects of this embodiment, a BoNT/D translocation domain comprises a polypeptide having an amino acid identity of, e.g., at least 70%, at least 75%, at least 80%, at least 85%, at least 90%, at least 95%, or at least 97% to amino acids 446-864 of SEQ ID NO: 4; or at most 70%, at most 75%, at most 80%, at most 85%, at most 90%, at most 95%, or at most 97% to amino acids 446-864 of SEQ ID NO: 4. In yet other aspects of this embodiment, a BoNT/D translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 446-864 of SEQ ID NO: 4; or at most 1, 2, 3, 4, 5, 6, 7, 8, 9, 10, 20, 30, 40, 50, or 100 non-contiguous amino acid deletions, additions, and/or substitutions relative to amino acids 446-864 of SEQ ID NO: 4. In still other aspects of this embodiment, a BoNT/D translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 446-864 of SEQ ID NO: 4; or at most 1, 2, 3, 4, 5, 6, 7, 8, 9, 10, 20, 30, 40, 50, or 100 contiguous amino acid substitutions relative to amino acids 446-864 of SEQ ID NO: 4.

In another embodiment, a Clostridial toxin translocation domain comprises a BoNT/E translocation domain. In an aspect of this embodiment, a BoNT/E translocation domain comprises amino acids 423-847 of SEQ ID NO: 5. In another aspect of this embodiment, a BoNT/E translocation domain comprises a naturally occurring BoNT/E translocation domain variant, such as, e.g., a translocation domain from a BoNT/E isoform or a translocation domain from a BoNT/E subtype. In another aspect of this embodiment, a BoNT/E translocation domain comprises amino acids 423-847 of a naturally occurring BoNT/E translocation domain variant of SEQ ID NO: 5, such as, e.g., amino acids 423-847 of a BoNT/E isoform of SEQ ID NO: 5 or amino acids 423-847 of a BoNT/E subtype of SEQ ID NO: 5. In still another aspect of this embodiment, a BoNT/E translocation domain comprises a non-naturally occurring BoNT/E translocation domain variant, such as, e.g., a conservative BoNT/E translocation domain variant, a non-conservative BoNT/E translocation domain variant, a BoNT/E chimeric translocation domain, an active BoNT/E translocation domain fragment, or any combination thereof. In still another aspect of this embodiment, a BoNT/E translocation domain comprises amino acids 423-847 of a non-naturally occurring BoNT/E translocation domain variant of SEQ ID NO: 5, such as, e.g., amino acids 423-847 of a conservative BoNT/E translocation domain variant of SEQ ID NO: 5, amino acids 423-847 of a non-conservative BoNT/E translocation domain variant of SEQ ID NO: 5, amino acids 423-847 of an active BoNT/E translocation domain fragment of SEQ ID NO: 5, or any combination thereof.

In other aspects of this embodiment, a BoNT/E translocation domain comprises a polypeptide having an amino acid identity of, e.g., at least 70%, at least 75%, at least 80%, at least 85%, at least 90%, at least 95%, or at least 97% to amino acids 423-847 of SEQ ID NO: 5; or at most 70%, at most 75%, at most 80%, at most 85%, at most 90%, at most 95%, or at most 97% to amino acids 423-847 of SEQ ID NO: 5. In yet other aspects of this embodiment, a BoNT/E translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 423-847 of SEQ ID NO: 5; or at most 1, 2, 3, 4, 5, 6, 7, 8, 9, 10, 20, 30, 40, 50, or 100 non-contiguous amino acid deletions, additions, and/or substitutions relative to amino acids 423-847 of SEQ ID NO: 5. In still other aspects of this embodiment, a BoNT/E translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 423-847 of SEQ ID NO: 5; or at most 1, 2, 3, 4, 5, 6, 7, 8, 9, 10, 20, 30, 40, 50, or 100 contiguous amino acid substitutions relative to amino acids 423-847 of SEQ ID NO: 5.

In another embodiment, a Clostridial toxin translocation domain comprises a BoNT/F translocation domain. In an aspect of this embodiment, a BoNT/F translocation domain comprises amino acids 440-866 of SEQ ID NO: 6. In another aspect of this embodiment, a BoNT/F translocation domain comprises a naturally occurring BoNT/F translocation domain variant, such as, e.g., a translocation domain from a BoNT/F isoform or a translocation domain from a BoNT/F subtype. In another aspect of this embodiment, a BoNT/F translocation domain comprises amino acids 440-866 of a naturally occurring BoNT/F translocation domain variant of SEQ ID NO: 6, such as, e.g., amino acids 440-866 of a BoNT/F isoform of SEQ ID NO: 6 or amino acids 440-866 of a BoNT/F subtype of SEQ ID NO: 6. In still another aspect of this embodiment, a BoNT/F translocation domain comprises a non-naturally occurring BoNT/F translocation domain variant, such as, e.g., a conservative BoNT/F translocation domain variant, a non-conservative BoNT/F translocation domain variant, a BoNT/F chimeric translocation domain, an active BoNT/F translocation domain fragment, or any combination thereof. In still another aspect of this embodiment, a BoNT/F translocation domain comprises amino acids 440-866 of a non-naturally occurring BoNT/F translocation domain variant of SEQ ID NO: 6, such as, e.g., amino acids 440-866 of a conservative BoNT/F translocation domain variant of SEQ ID NO: 6, amino acids 440-866 of a non-conservative BoNT/F translocation domain variant of SEQ ID NO: 6, amino acids 440-866 of an active BoNT/F translocation domain fragment of SEQ ID NO: 6, or any combination thereof.

In other aspects of this embodiment, a BoNT/F translocation domain comprises a polypeptide having an amino acid identity of, e.g., at least 70%, at least 75%, at least 80%, at least 85%, at least 90%, at least 95%, or at least 97% to amino acids 440-866 of SEQ ID NO: 6; or at most 70%, at most 75%, at most 80%, at most 85%, at most 90%, at most 95%, or at most 97% to amino acids 440-866 of SEQ ID NO: 6. In yet other aspects of this embodiment, a BoNT/F translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 440-866 of SEQ ID NO: 6; or at most 1, 2, 3, 4, 5, 6, 7, 8, 9, 10, 20, 30, 40, 50, or 100 non-contiguous amino acid deletions, additions, and/or substitutions relative to amino acids 440-866 of SEQ ID NO: 6. In still other aspects of this embodiment, a BoNT/F translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 440-866 of SEQ ID NO: 6; or at most 1, 2, 3, 4, 5, 6, 7, 8, 9, 10, 20, 30, 40, 50, or 100 contiguous amino acid substitutions relative to amino acids 440-866 of SEQ ID NO: 6.

In another embodiment, a Clostridial toxin translocation domain comprises a BoNT/G translocation domain. In an aspect of this embodiment, a BoNT/G translocation domain comprises amino acids 447-865 of SEQ ID NO: 7. In another aspect of this embodiment, a BoNT/G translocation domain comprises a naturally occurring BoNT/G translocation domain variant, such as, e.g., a translocation domain from a BoNT/G isoform or a translocation domain from a BoNT/G subtype. In another aspect of this embodiment, a BoNT/G translocation domain comprises amino acids 447-865 of a naturally occurring BoNT/G translocation domain variant of SEQ ID NO: 7, such as, e.g., amino acids 447-865 of a BoNT/G isoform of SEQ ID NO: 7 or amino acids 447-865 of a BoNT/G subtype of SEQ ID NO: 7. In still another aspect of this embodiment, a BoNT/G translocation domain comprises a non-naturally occurring BoNT/G translocation domain variant, such as, e.g., a conservative BoNT/G translocation domain variant, a non-conservative BoNT/G translocation domain variant, a BoNT/G chimeric translocation domain, an active BoNT/G translocation domain fragment, or any combination thereof. In still another aspect of this embodiment, a BoNT/G translocation domain comprises amino acids 447-865 of a non-naturally occurring BoNT/G translocation domain variant of SEQ ID NO: 7, such as, e.g., amino acids 447-865 of a conservative BoNT/G translocation domain variant of SEQ ID NO: 7, amino acids 447-865 of a non-conservative BoNT/G translocation domain variant of SEQ ID NO: 7, amino acids 447-865 of an active BoNT/G translocation domain fragment of SEQ ID NO: 7, or any combination thereof.

In other aspects of this embodiment, a BoNT/G translocation domain comprises a polypeptide having an amino acid identity of, e.g., at least 70%, at least 75%, at least 80%, at least 85%, at least 90%, at least 95%, or at least 97% to amino acids 447-865 of SEQ ID NO: 7; or at most 70%, at most 75%, at most 80%, at most 85%, at most 90%, at most 95%, or at most 97% to amino acids 447-865 of SEQ ID NO: 7. In yet other aspects of this embodiment, a BoNT/G translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 447-865 of SEQ ID NO: 7; or at most 1, 2, 3, 4, 5, 6, 7, 8, 9, 10, 20, 30, 40, 50, or 100 non-contiguous amino acid deletions, additions, and/or substitutions relative to amino acids 447-865 of SEQ ID NO: 7. In still other aspects of this embodiment, a BoNT/G translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 447-865 of SEQ ID NO: 7; or at most 1, 2, 3, 4, 5, 6, 7, 8, 9, 10, 20, 30, 40, 50, or 100 contiguous amino acid deletions, additions, and/or substitutions relative to amino acids 447-865 of SEQ ID NO: 7.

In another embodiment, a Clostridial toxin translocation domain comprises a TeNT translocation domain. In an aspect of this embodiment, a TeNT translocation domain comprises amino acids 458-881 of SEQ ID NO: 8. In another aspect of this embodiment, a TeNT translocation domain comprises a naturally occurring TeNT translocation domain variant, such as, e.g., a translocation domain from a TeNT isoform or a translocation domain from a TeNT subtype. In another aspect of this embodiment, a TeNT translocation domain comprises amino acids 458-881 of a naturally occurring TeNT translocation domain variant of SEQ ID NO: 8, such as, e.g., amino acids 458-881 of a TeNT isoform of SEQ ID NO: 8 or amino acids 458-881 of a TeNT subtype of SEQ ID NO: 8. In still another aspect of this embodiment, a TeNT translocation domain comprises a non-naturally occurring TeNT translocation domain variant, such as, e.g., a conservative TeNT translocation domain variant, a non-conservative TeNT translocation domain variant, a TeNT chimeric translocation domain, an active TeNT translocation domain fragment, or any combination thereof. In still another aspect of this embodiment, a TeNT translocation domain comprises amino acids 458-881 of a non-naturally occurring TeNT translocation domain variant of SEQ ID NO: 8, such as, e.g., amino acids 458-881 of a conservative TeNT translocation domain variant of SEQ ID NO: 8, amino acids 458-881 of a non-conservative TeNT translocation domain variant of SEQ ID NO: 8, amino acids 458-881 of an active TeNT translocation domain fragment of SEQ ID NO: 8, or any combination thereof.

In other aspects of this embodiment, a TeNT translocation domain comprises a polypeptide having an amino acid identity of, e.g., at least 70%, at least 75%, at least 80%, at least 85%, at least 90%, at least 95%, or at least 97% to amino acids 458-881 of SEQ ID NO: 8; or at most 70%, at most 75%, at most 80%, at most 85%, at most 90%, at most 95%, or at most 97% to amino acids 458-881 of SEQ ID NO: 8. In yet other aspects of this embodiment, a TeNT translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 458-881 of SEQ ID NO: 8; or at most 1, 2, 3, 4, 5, 6, 7, 8, 9, 10, 20, 30, 40, 50, or 100 non-contiguous amino acid deletions, additions, and/or substitutions relative to amino acids 458-881 of SEQ ID NO: 8. In still other aspects of this embodiment, a TeNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 458-881 of SEQ ID NO: 8; or at most 1, 2, 3, 4, 5, 6, 7, 8, 9, 10, 20, 30, 40, 50, or 100 contiguous amino acid deletions, additions, and/or substitutions relative to amino acids 458-881 of SEQ ID NO: 8.

In another embodiment, a Clostridial toxin translocation domain comprises a BaNT translocation domain. In an aspect of this embodiment, a BaNT translocation domain comprises amino acids 432-857 of SEQ ID NO: 9. In another aspect of this embodiment, a BaNT translocation domain comprises a naturally occurring BaNT translocation domain variant, such as, e.g., a translocation domain from a BaNT isoform or a translocation domain from a BaNT subtype. In another aspect of this embodiment, a BaNT translocation domain comprises amino acids 432-857 of a naturally occurring BaNT translocation domain variant of SEQ ID NO: 9, such as, e.g., amino acids 432-857 of a BaNT isoform of SEQ ID NO: 9 or amino acids 432-857 of a BaNT subtype of SEQ ID NO: 9. In still another aspect of this embodiment, a BaNT translocation domain comprises a non-naturally occurring BaNT translocation domain variant, such as, e.g., a conservative BaNT translocation domain variant, a non-conservative BaNT translocation domain variant, a BaNT chimeric translocation domain, an active BaNT translocation domain fragment, or any combination thereof. In still another aspect of this embodiment, a BaNT translocation domain comprises amino acids 432-857 of a non-naturally occurring BaNT translocation domain variant of SEQ ID NO: 9, such as, e.g., amino acids 432-857 of a conservative BaNT translocation domain variant of SEQ ID NO: 9, amino acids 432-857 of a non-conservative BaNT translocation domain variant of SEQ ID NO: 9, amino acids 432-857 of an active BaNT translocation domain fragment of SEQ ID NO: 9, or any combination thereof.

In other aspects of this embodiment, a BaNT translocation domain comprises a polypeptide having an amino acid identity of, e.g., at least 70%, at least 75%, at least 80%, at least 85%, at least 90%, at least 95%, or at least 97% to amino acids 432-857 of SEQ ID NO: 9; or at most 70%, at most 75%, at most 80%, at most 85%, at most 90%, at most 95%, or at most 97% to amino acids 432-857 of SEQ ID NO: 9. In yet other aspects of this embodiment, a BaNT translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 432-857 of SEQ ID NO: 9; or at most 1, 2, 3, 4, 5, 6, 7, 8, 9, 10, 20, 30, 40, 50, or 100 non-contiguous amino acid deletions, additions, and/or substitutions relative to amino acids 432-857 of SEQ ID NO: 9. In still other aspects of this embodiment, a BaNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 432-857 of SEQ ID NO: 9; or at most 1, 2, 3, 4, 5, 6, 7, 8, 9, 10, 20, 30, 40, 50, or 100 contiguous amino acid deletions, additions, and/or substitutions relative to amino acids 432-857 of SEQ ID NO: 9.

In another embodiment, a Clostridial toxin translocation domain comprises a BuNT translocation domain. In an aspect of this embodiment, a BuNT translocation domain comprises amino acids 423-847 of SEQ ID NO: 10. In another aspect of this embodiment, a BuNT translocation domain comprises a naturally occurring BuNT translocation domain variant, such as, e.g., a translocation domain from a BuNT isoform or a translocation domain from a BuNT subtype. In another aspect of this embodiment, a BuNT translocation domain comprises amino acids 423-847 of a naturally occurring BuNT translocation domain variant of SEQ ID NO: 10, such as, e.g., amino acids 423-847 of a BuNT isoform of SEQ ID NO: 10 or amino acids 423-847 of a BuNT subtype of SEQ ID NO: 10. In still another aspect of this embodiment, a BuNT translocation domain comprises a non-naturally occurring BuNT translocation domain variant, such as, e.g., a conservative BuNT translocation domain variant, a non-conservative BuNT translocation domain variant, a BuNT chimeric translocation domain, an active BuNT translocation domain fragment, or any combination thereof. In still another aspect of this embodiment, a BuNT translocation domain comprises amino acids 423-847 of a non-naturally occurring BuNT translocation domain variant of SEQ ID NO: 10, such as, e.g., amino acids 423-847 of a conservative BuNT translocation domain variant of SEQ ID NO: 10, amino acids 423-847 of a non-conservative BuNT translocation domain variant of SEQ ID NO: 10, amino acids 423-847 of an active BuNT translocation domain fragment of SEQ ID NO: 10, or any combination thereof.

In other aspects of this embodiment, a BuNT translocation domain comprises a polypeptide having an amino acid identity of, e.g., at least 70%, at least 75%, at least 80%, at least 85%, at least 90%, at least 95%, or at least 97% of amino acids 423-847 of SEQ ID NO: 10; or at most 70%, at most 75%, at most 80%, at most 85%, at most 90%, at most 95%, or at most 97% of amino acids 423-847 of SEQ ID NO: 10. In yet other aspects of this embodiment, a BuNT translocation domain comprises a polypeptide having, e.g., at least 1, 2, 3, 4, 5, 6, 7, 8, 9, 10, 20, 30, 40, 50, or 100 non-contiguous amino acid deletions, additions, and/or substitutions relative to amino acids 423-847 of SEQ ID NO: 10; or at most 1, 2, 3, 4, 5, 6, 7, 8, 9, 10, 20, 30, 40, 50, or 100 non-contiguous amino acid deletions, additions, and/or substitutions relative to amino acids 423-847 of SEQ ID NO: 10. In still other aspects of this embodiment, a BuNT translocation domain comprises a polypeptide having, e.g., at least 1, 2, 3, 4, 5, 6, 7, 8, 9, 10, 20, 30, 40, 50, or 100 contiguous amino acid deletions, additions, and/or substitutions relative to amino acids 423-847 of SEQ ID NO: 10; or at most 1, 2, 3, 4, 5, 6, 7, 8, 9, 10, 20, 30, 40, 50, or 100 contiguous amino acid deletions, additions, and/or substitutions relative to amino acids 423-847 of SEQ ID NO: 10.

In another aspect of the invention, a TVEMP comprises, in part, a retargeted peptide binding domain. As used herein, the term "peptide binding domain" refers to an amino acid sequence region able to selectively bind to a cell surface marker characteristic of the target cell under physiological conditions. As used herein, the term "retargeted peptide binding domain" refers to a peptide binding domain that does not selectively bind to a Clostridial toxin receptor under physiological conditions. The cell surface marker may comprise a polypeptide, a polysaccharide, a lipid, a glycoprotein, a lipoprotein, or may have structural characteristics of more than one of these. As used herein, the term "selectively bind" refers to molecule is able to bind its target receptor under physiological conditions, or in vitro conditions substantially approximating physiological conditions, to a statistically significantly greater degree relative to other, non-target receptors.

Thus, in an embodiment, a retargeted binding domain that selectively binds a target receptor has a dissociation equilibrium constant ($K_D$) that is greater for the target receptor relative to a non-target receptor by, e.g., at least one-fold, at least two-fold, at least three-fold, at least four fold, at least five-fold, at least 10 fold, at least 50 fold, at least 100 fold, at least 1000 fold, at least 10,000 fold, or at least 100,000 fold. In another embodiment, a retargeted binding domain that selectively binds a target receptor has a dissociation equilibrium constant ($K_D$) that is greater for the target receptor relative to a non-target receptor by, e.g., about one-fold to about three-fold, about one-fold to about five-fold, about one-fold to about 10-fold, about one-fold to about 100-fold, about one-fold to about 1000-fold, about five-fold to about 10-fold, about five-fold to about 100-fold, about five-fold to about 1000-fold, about 10-fold to about 100-fold, about 10-fold to about 1000-fold, about 10-fold to about 10,000-fold, or about 10-fold to about 100,000-fold.

An example of a retargeted binding element disclosed in the present specification is a galanin peptide binding domain. Non-limiting examples of a galanin peptide binding domain include a galanin or a galanin message-associated peptide (GMAP).

Thus, in an embodiment, a retargeted binding domain comprises a galanin peptide binding domain. In aspects of this embodiment, a galanin peptide binding domain comprises a galanin or a galanin message-associated peptide (GMAP). In other aspects of this embodiment, a galanin peptide binding domain comprises SEQ ID NO: 67 or SEQ ID NO: 68.

In other aspects of this embodiment, a galanin binding domain comprises a polypeptide having an amino acid identity of, e.g., at least 70%, at least 75%, at least 80%, at least 85%, at least 90%, at least 95%, or at least 97% to SEQ ID NO: 67 or SEQ ID NO: 68; or at most 70%, at most 75%, at most 80%, at most 85%, at most 90%, at most 95%, or at most 97% to SEQ ID NO: 67 or SEQ ID NO: 68. In yet other aspects of this embodiment, a galanin binding domain comprises a polypeptide having, e.g., at least 1, 2, 3, 4, 5, 6, 7, 8, 9, or 10 non-contiguous amino acid deletions, additions, and/or substitutions relative to SEQ ID NO: 67 or SEQ ID NO: 68; or at most 1, 2, 3, 4, 5, 6, 7, 8, 9, or 10 non-contiguous amino acid deletions, additions, and/or substitutions relative to SEQ ID NO: 67 or SEQ ID NO: 68. In still other aspects of this embodiment, a galanin binding domain comprises a polypeptide having, e.g., at least 1, 2, 3, 4, 5, 6, 7, 8, 9, or 10 contiguous amino acid deletions, additions, and/or substitutions relative to SEQ ID NO: 67 or SEQ ID NO: 68; or at most 1, 2, 3, 4, 5, 6, 7, 8, 9, or 10 contiguous amino acid deletions, additions, and/or substitutions relative to SEQ ID NO: 67 or SEQ ID NO: 68.

Another example of a retargeted binding element disclosed in the present specification is a protease activated receptor (PAR) peptide binding domain. Non-limiting examples of a PAR peptide binding domain include a PAR1 peptide, a PAR2 peptide, a PAR3 peptide and a PAR4 peptide.

Thus, in an embodiment, a retargeted binding element comprises a PAR peptide binding domain. In aspects of this embodiment, a PAR peptide binding domain comprises a PAR1 peptide, a PAR2 peptide, a PAR3 peptide or a PAR4 peptide. In other aspects of this embodiment, a PAR peptide binding domain comprises amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

In other aspects of this embodiment, a PAR peptide binding domain comprises a polypeptide having an amino acid identity of, e.g., at least 70%, at least 75%, at least 80%, at least 85%, at least 90%, at least 95%, or at least 97% to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72; or at most 70%, at most 75%, at most 80%, at most 85%, at most 90%, at most 95%, or at most 97% to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

In yet other aspects of this embodiment, a PAR peptide binding domain comprises a polypeptide having, e.g., at least 1, 2, 3, 4, or 5 non-contiguous amino acid deletions, additions, and/or substitutions relative to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72; or at most 1, 2, 3, 4, or 5 non-contiguous amino acid deletions, additions, and/or substitutions relative to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72. In still other aspects of this embodiment, a PAR peptide binding domain comprises a polypeptide having, e.g., at least 1, 2, 3, 4, or 5 contiguous amino acid deletions, additions, and/or substitutions relative to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72; or at most 1, 2, 3, 4, or 5 contiguous amino acid deletions, additions, and/or substitutions relative to amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

Another example of a retargeted binding element disclosed in the present specification is a somatostatin peptide binding domain. Thus, in an embodiment, a retargeted binding element comprises a somatostatin peptide binding domain. In aspects of this embodiment, a somatostatin peptide binding domain comprises SEQ ID NO: 73. In other aspects of this embodiment, a somatostatin peptide binding domain comprises amino acids 99-116 of SEQ ID NO: 73.

In other aspects of this embodiment, a somatostatin peptide binding domain comprises a polypeptide having an amino acid identity of, e.g., at least 70%, at least 75%, at least 80%, at least 85%, at least 90%, at least 95%, or at least 97% to SEQ ID NO: 73; or at most 70%, at most 75%, at most 80%, at most 85%, at most 90%, at most 95%, or at most 97% to SEQ ID NO: 73. In yet other aspects of this embodiment, a somatostatin peptide binding domain comprises a polypeptide having, e.g., at least 1, 2, 3, 4, 5, 6, 7, 8, 9, 10, 15 or 20 non-contiguous amino acid deletions, additions, and/or substitutions relative to SEQ ID NO: 73; or at most 1, 2, 3, 4, 5, 6, 7, 8, 9, 10, 15 or 20 non-contiguous amino acid deletions, additions, and/or substitutions relative to SEQ ID NO: 73. In still other aspects of this embodiment, a somatostatin peptide binding domain comprises a polypeptide having, e.g., at least 1, 2, 3, 4, 5, 6, 7, 8, 9, 10, 15 or 20 contiguous amino acid deletions, additions, and/or substitutions relative to SEQ ID NO: 73; or at most 1, 2, 3, 4, 5, 6, 7, 8, 9, 10, 15 or 20 contiguous amino acid deletions, additions, and/or substitutions relative to SEQ ID NO: 73.

In other aspects of this embodiment, a somatostatin peptide binding domain comprises a polypeptide having an amino acid identity of, e.g., at least 70%, at least 75%, at least 80%, at least 85%, at least 90%, at least 95%, or at least 97% to amino acids 99-116 of SEQ ID NO: 73; or at most 70%, at most 75%, at most 80%, at most 85%, at most 90%, at most 95%, or at most 97% to amino acids 99-116 of SEQ ID NO: 73. In yet other aspects of this embodiment, a somatostatin peptide binding domain comprises a polypeptide having, e.g., at least 1, 2, 3, 4, 5, 6, 7, 8, 9, or 10 non-contiguous amino acid deletions, additions, and/or substitutions relative to amino acids 99-116 of SEQ ID NO: 73; or at most 1, 2, 3, 4, 5, 6, 7, 8, 9, or 10 non-contiguous amino acid deletions, additions, and/or substitutions relative to amino acids 99-116 of SEQ ID NO: 73. In still other aspects of this embodiment, a somatostatin peptide binding domain comprises a polypeptide having, e.g., at least 1, 2, 3, 4, 5, 6, 7, 8, 9, or 10 contiguous amino acid deletions, additions, and/or substitutions relative to amino acids 99-116 of SEQ ID NO: 73; or at most 1, 2, 3, 4, 5, 6, 7, 8, 9, or 10 contiguous amino acid deletions, additions, and/or substitutions relative to amino acids 99-116 of SEQ ID NO: 73.

Another example of a retargeted binding element disclosed in the present specification is a neurotensin peptide binding domain. Non-limiting examples of a neurotensin peptide binding domain include a neurotensin or a neuromedin N.

Thus, in an embodiment, a retargeted binding element comprises a neurotensin peptide binding domain. In aspects of this embodiment, a neurotensin peptide binding domain comprises SEQ ID NO: 73. In other aspects of this embodiment, a neurotensin peptide binding domain comprises SEQ ID NO: 74. In other aspects of this embodiment, a neurotensin peptide binding domain comprises amino acids 143-148 or amino acids 151-163 of SEQ ID NO: 74.

In other aspects of this embodiment, a neurotensin peptide binding domain comprises a polypeptide having an amino acid identity of, e.g., at least 70%, at least 75%, at least 80%, at least 85%, at least 90%, at least 95%, or at least 97% to SEQ ID NO: 74; or at most 70%, at most 75%, at most 80%, at most 85%, at most 90%, at most 95%, or at most 97% to SEQ ID NO: 74. In yet other aspects of this embodiment, a neurotensin peptide binding domain comprises a polypeptide having, e.g., at least 1, 2, 3, 4, 5, 6, 7, 8, 9, 10, 15 or 20 non-contiguous amino acid deletions, additions, and/or substitutions relative to SEQ ID NO: 74; or at most 1, 2, 3, 4, 5, 6, 7, 8, 9, 10, 15 or 20 non-contiguous amino acid deletions, additions, and/or substitutions relative to SEQ ID NO: 74. In still other aspects of this embodiment, a neurotensin peptide binding domain comprises a polypeptide having, e.g., at least 1, 2, 3, 4, 5, 6, 7, 8, 9, 10, 15 or 20 contiguous amino acid deletions, additions, and/or substitutions relative to SEQ ID NO: 74; or at most 1, 2, 3, 4, 5, 6, 7, 8, 9, 10, 15 or 20 contiguous amino acid deletions, additions, and/or substitutions relative to SEQ ID NO: 74.

In other aspects of this embodiment, a neurotensin peptide binding domain comprises a polypeptide having an amino acid identity of, e.g., at least 70%, at least 75%, at least 80%, at least 85%, at least 90%, at least 95%, or at least 97% to amino acids 143-148 or amino acids 151-163 of SEQ ID NO: 74; or at most 70%, at most 75%, at most 80%, at most 85%, at most 90%, at most 95%, or at most 97% to amino acids 143-148 or amino acids 151-163 of SEQ ID NO: 74. In yet other aspects of this embodiment, a neurotensin peptide binding domain comprises a polypeptide having, e.g., at least 1, 2, 3, 4, 5, 6, 7, 8, 9, or 10 non-contiguous amino acid deletions, additions, and/or substitutions relative to amino acids 143-148 or amino acids 151-163 of SEQ ID NO: 74; or at most 1, 2, 3, 4, 5, 6, 7, 8, 9, or 10 non-contiguous amino acid deletions, additions, and/or substitutions relative to amino acids 143-148 or amino acids 151-163 of SEQ ID NO: 74. In still other aspects of this embodiment, a neurotensin peptide binding domain comprises a polypeptide having, e.g., at least 1, 2, 3, 4, 5, 6, 7, 8, 9, or 10 contiguous amino acid deletions, additions, and/or substitutions relative to amino acids 143-148 or amino acids 151-163 of SEQ ID NO: 74; or at most 1, 2, 3, 4, 5, 6, 7, 8, 9, or 10 contiguous amino acid deletions, additions, and/or substitutions relative to amino acids 143-148 or amino acids 151-163 of SEQ ID NO: 74.

Another example of a retargeted binding element disclosed in the present specification is a Ly6/urokinase plasminogen activator receptor-related protein (SLURP) peptide. Non-limiting examples of a SLURP peptide binding domain include a SLURP-1 or a SLURP-2.

Thus, in an embodiment, a retargeted binding domain comprises a SLURP peptide binding domain. In aspects of this embodiment, a SLURP peptide binding domain comprises a SLURP-1 or a SLURP-2. In other aspects of this embodiment, a SLURP peptide binding domain comprises SEQ ID NO: 75 or SEQ ID NO: 76. In other aspects of this embodiment, a SLURP peptide binding domain comprises amino acids 23-101 of SEQ ID NO: 75 or amino acids 23-95 of SEQ ID NO: 76.

In other aspects of this embodiment, a SLURP peptide binding domain comprises a polypeptide having an amino acid identity of, e.g., at least 70%, at least 75%, at least 80%, at least 85%, at least 90%, at least 95%, or at least 97% to SEQ ID NO: 75 or SEQ ID NO: 76; or at most 70%, at most 75%, at most 80%, at most 85%, at most 90%, at most 95%, or at most 97% to SEQ ID NO: 75 or SEQ ID NO: 76. In yet other aspects of this embodiment, a SLURP peptide binding domain comprises a polypeptide having, e.g., at least 1, 2, 3, 4, 5, 6, 7, 8, 9, 10, 15 or 20 non-contiguous amino acid deletions, additions, and/or substitutions relative to SEQ ID NO: 75 or SEQ ID NO: 76; or at most 1, 2, 3, 4, 5, 6, 7, 8, 9, 10, 15 or 20 non-contiguous amino acid deletions, additions, and/or substitutions relative to SEQ ID NO: 75 or SEQ ID NO: 76. In still other aspects of this embodiment, a SLURP peptide binding domain comprises a polypeptide having, e.g., at least 1, 2, 3, 4, 5, 6, 7, 8, 9, 10, 15 or 20 contiguous amino acid deletions, additions, and/or substitutions relative to SEQ ID NO: 75 or SEQ ID NO: 76; or at most 1, 2, 3, 4, 5, 6, 7, 8, 9, 10, 15 or 20 contiguous amino acid deletions, additions, and/or substitutions relative to SEQ ID NO: 75 or SEQ ID NO: 76.

In other aspects of this embodiment, a SLURP peptide binding domain comprises a polypeptide having an amino acid identity of, e.g., at least 70%, at least 75%, at least 80%, at least 85%, at least 90%, at least 95%, or at least 97% to amino acids 23-101 of SEQ ID NO: 75 or amino acids 23-95 of SEQ ID NO: 76; or at most 70%, at most 75%, at most 80%, at most 85%, at most 90%, at most 95%, or at most 97% to amino acids 23-101 of SEQ ID NO: 75 or amino acids 23-95 of SEQ ID NO: 76. In yet other aspects of this embodiment, a SLURP peptide binding domain comprises a polypeptide having, e.g., at least 1, 2, 3, 4, 5, 6, 7, 8, 9, 10, 15 or 20 non-contiguous amino acid deletions, additions, and/or substitutions relative to amino acids 23-101 of SEQ ID NO: 75 or amino acids 23-95 of SEQ ID NO: 76; or at most 1, 2, 3, 4, 5, 6, 7, 8, 9, 10, 15 or 20 non-contiguous amino acid deletions, additions, and/or substitutions relative to amino acids 23-101 of SEQ ID NO: 75 or amino acids 23-95 of SEQ ID NO: 76. In still other aspects of this embodiment, a SLURP peptide binding domain comprises a polypeptide having, e.g., at least 1, 2, 3, 4, 5, 6, 7, 8, 9, 10, 15 or 20 contiguous amino acid deletions, additions, and/or substitutions relative to amino acids 23-101 of SEQ ID NO: 75 or amino acids 23-95 of SEQ ID NO: 76; or at most 1, 2, 3, 4, 5, 6, 7, 8, 9, 10, 15 or 20 contiguous amino acid deletions, additions, and/or substitutions relative to amino acids 23-101 of SEQ ID NO: 75 or amino acids 23-95 of SEQ ID NO: 76.

Figure 2:
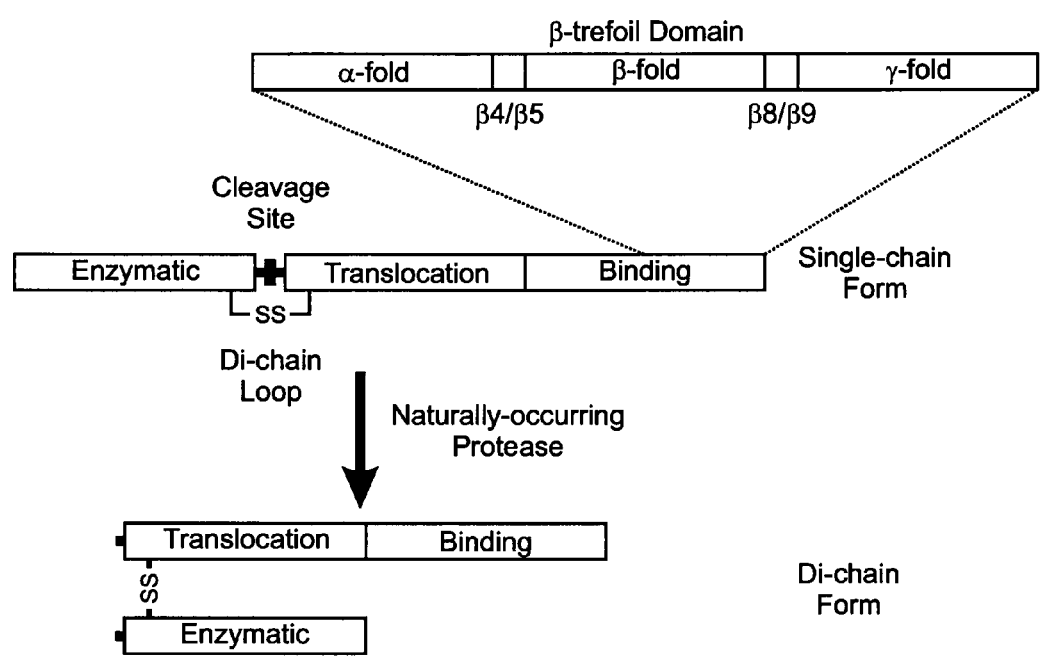
FIG. 2 shows the domain organization of naturally-occurring Clostridial toxins. The single-chain form depicts the amino to carboxyl linear organization comprising an enzymatic domain, a translocation domain, and a retargeted peptide binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single-chain form of the toxin into the di-chain form. Above the single-chain form, the HCC region of the Clostridial toxin binding domain is depicted. This region comprises the β-trefoil domain which comprises in an amino to carboxyl linear organization an α-fold, a β4/β5 hairpin turn, a β-fold, a β8/β9 hairpin turn and a γ-fold.

Clostridial toxins are each translated as a single-chain polypeptide of approximately 150 kDa that is subsequently cleaved by proteolytic scission within a disulfide loop by a naturally-occurring protease. This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains (FIG. 2). To facilitate recombinant production of a TVEMP, an exogenous protease cleavage site can be used to convert the single-chain polypeptide form of a TVEMP disclosed in the present specification into the di-chain form. See, e.g., Steward, L. E. et al., *Modified Clostridial Toxins with Enhanced Targeting Capabilities For Endogenous Clostridial Toxin Receptor Systems*, U.S. Patent Publication No. US 2008/0096248 (Apr. 24, 2008); Steward, L. E. et al., *Activatable Clostridial Toxins*, U.S. Patent Publication No. US 2008/0032930 (Feb. 7, 2008); Steward, supra, (2007); Dolly, supra, (2007); Foster, supra, WO 2006/059093 (2006); and Foster, supra, WO 2006/059105 (2006), each of which is hereby incorporated by reference in its entirety.

It is envisioned that any and all protease cleavage sites can be used to convert the single-chain polypeptide form of a Clostridial toxin into the di-chain form, including, without limitation, endogenous di-chain loop protease cleavage sites and exogenous protease cleavage sites. Thus, in an aspect of the invention, a TVEMP comprises, in part, an endogenous protease cleavage site within a di-chain loop region. In another aspect of the invention, a TVEMP comprises, in part, an exogenous protease cleavage site within a di-chain loop region. As used herein, the term "di-chain loop region" refers to the amino acid sequence of a Clostridial toxin containing a protease cleavage site used to convert the single-chain form of a Clostridial toxin into the di-chain form. Non-limiting examples of a Clostridial toxin di-chain loop region, include, a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; and a di-chain loop region of TeNT comprising amino acids 439-467 of SEQ ID NO: 8 (Table 4).

TABLE 4

Di-chain Loop Region

| Toxin | Di-chain Loop Region Containing the Naturally-occurring Protease Cleavage Site |
|---|---|
| BoNT/A | CVRGIITSKTKSLDKGYNK*----ALNDLC |
| BoNT/B | CKSVK*------------------APGIC |
| BoNT/C1 | CHKAIDGRSLYNK*------------TLDC |
| BoNT/D | CLRLTKNSR*---------------DDSTC |
| BoNT/E | CKNIVSVKGIR*--------------KSIC |
| BoNT/F | CKSVIPRKGTK*------------APPRLC |
| BoNT/G | CKPVMYKNTGK*--------------SEQC |
| TeNT | CKKIIPPTNIRENLYNRTA*SLTDLGGELC |
| BaNT | CKS-IVSKKGTK*------------NSLC |
| BuNT | CKN-IVSVKGIR*------------KSIC |

The amino acid sequence displayed are as follows: BoNT/A, residues 430-454 of SEQ ID NO: 1; BoNT/B, residues 437-446 of SEQ ID NO: 2; BoNT/C1, residues 437-453 of SEQ ID NO: 3; BoNT/D, residues 437-450 of SEQ ID NO: 4; BoNT/E, residues 412-426 of SEQ ID NO: 5; BoNT/F, residues 429-445 of SEQ ID NO: 6; BoNT/G, residues 436-450 of SEQ ID NO: 7; TeNT, residues 439-467 of SEQ ID NO: 8; BaNT, residues 421-435 of SEQ ID NO: 9; and BuNT, residues 412-426 of SEQ ID NO: 10. An asterisks (*) indicates the peptide bond that is cleaved by a Clostridial toxin protease.

As used herein, the term "endogenous di-chain loop protease cleavage site" is synonymous with a "naturally occurring di-chain loop protease cleavage site" and refers to a naturally occurring protease cleavage site found within the di-chain loop region of a naturally occurring Clostridial toxin and includes, without limitation, naturally occurring Clostridial toxin di-chain loop protease cleavage site variants, such as, e.g., Clostridial toxin di-chain loop protease cleavage site isoforms and Clostridial toxin di-chain loop protease cleavage site subtypes. Non-limiting examples of an endogenous protease cleavage site, include, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site and a TeNT di-chain loop protease cleavage site.

As mentioned above, Clostridial toxins are translated as a single-chain polypeptide of approximately 150 kDa that is subsequently cleaved by proteolytic scission within a disulfide loop by a naturally-occurring protease. This posttranslational processing yields a di-chain molecule comprising an approximately 50 kDa light chain (LC) and an approximately 100 kDa heavy chain (HC) held together by a single disulphide bond and noncovalent interactions. While the identity of the protease is currently unknown, the di-chain loop protease cleavage site for many Clostridial toxins has been determined. In BoNTs, cleavage at K448-A449 converts the single polypeptide form of BoNT/A into the di-chain form; cleavage at K441-A442 converts the single polypeptide form of BoNT/B into the di-chain form; cleavage at K449-T450 converts the single polypeptide form of BoNT/C1 into the di-chain form; cleavage at R445-D446 converts the single polypeptide form of BoNT/D into the di-chain form; cleavage at R422-K423 converts the single polypeptide form of BoNT/E into the di-chain form; cleavage at K439-A440 converts the single polypeptide form of BoNT/F into the di-chain form; and cleavage at K446-S447 converts the single polypeptide form of BoNT/G into the di-chain form. Proteolytic cleavage of the single polypeptide form of TeNT at A457-S458 results in the di-chain form. Proteolytic cleavage of the single polypeptide form of BaNT at K431-N432 results in the di-chain form. Proteolytic cleavage of the single polypeptide form of BuNT at R422-K423 results in the di-chain form. Such a di-chain loop protease cleavage site is operably-linked in-frame to a TVEMP as a fusion protein. However, it should also be noted that additional cleavage sites within the di-chain loop also appear to be cleaved resulting in the generation of a small peptide fragment being lost. As a non-limiting example, BoNT/A single-chain polypeptide cleavage ultimately results in the loss of a ten amino acid fragment within the di-chain loop.

Thus, in an embodiment, a protease cleavage site comprising an endogenous Clostridial toxin di-chain loop protease cleavage site is used to convert the single-chain toxin into the di-chain form. In aspects of this embodiment, conversion into the di-chain form by proteolytic cleavage occurs from a site comprising, e.g., a BoNT/A di-chain loop protease cleavage site, a BoNT/B di-chain loop protease cleavage site, a BoNT/C1 di-chain loop protease cleavage site, a BoNT/D di-chain loop protease cleavage site, a BoNT/E di-chain loop protease cleavage site, a BoNT/F di-chain loop protease cleavage site, a BoNT/G di-chain loop protease cleavage site, a TeNT di-chain loop protease cleavage site, a BaNT di-chain loop protease cleavage site, or a BuNT di-chain loop protease cleavage site.

In other aspects of this embodiment, conversion into the di-chain form by proteolytic cleavage occurs from a site comprising, e.g., a di-chain loop region of BoNT/A comprising amino acids 430-454 of SEQ ID NO: 1; a di-chain loop region of BoNT/B comprising amino acids 437-446 of SEQ ID NO: 2; a di-chain loop region of BoNT/C1 comprising amino acids 437-453 of SEQ ID NO: 3; a di-chain loop region of BoNT/D comprising amino acids 437-450 of SEQ ID NO: 4; a di-chain loop region of BoNT/E comprising amino acids 412-426 of SEQ ID NO: 5; a di-chain loop region of BoNT/F comprising amino acids 429-445 of SEQ ID NO: 6; a di-chain loop region of BoNT/G comprising amino acids 436-450 of SEQ ID NO: 7; or a di-chain loop region of TeNT comprising amino acids 439-467 of SEQ ID NO: 8; a di-chain loop region of BaNT comprising amino acids 421-435 of SEQ ID NO: 9; or a di-chain loop region of BuNT comprising amino acids 412-426 of SEQ ID NO: 10.

It is also envisioned that an exogenous protease cleavage site can be used to convert the single-chain polypeptide form of a TVEMP disclosed in the present specification into the di-chain form. As used herein, the term "exogenous protease cleavage site" is synonymous with a "non-naturally occurring protease cleavage site" or "non-native protease cleavage site" and refers to a protease cleavage site that is not normally present in a di-chain loop region from a naturally occurring Clostridial toxin, with the proviso that the exogenous protease cleavage site is not a human protease cleavage site or a protease cleavage site that is susceptible to a protease being expressed in the host cell that is expressing a construct encoding an activatable polypeptide disclosed in the present specification. It is envisioned that any and all exogenous protease cleavage sites can be used to convert the single-chain polypeptide form of a Clostridial toxin into the di-chain form are useful to practice aspects of the present invention. Non-limiting examples of exogenous protease cleavage sites include, e.g., a plant papain cleavage site, an insect papain cleavage site, a crustacian papain cleavage site, an enterokinase cleavage site, a human rhinovirus 3C protease cleavage site, a human enterovirus 3C protease cleavage site, a tobacco etch virus (TEV) protease cleavage site, a Tobacco Vein Mottling Virus (TVMV) cleavage site, a subtilisin cleavage site, a hydroxylamine cleavage site, or a Caspase 3 cleavage site.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can have a length of, e.g., at least 6, 7, 8, 9, 10, 15, 20, 25, 30, 40, 50, or at least 60 amino acids; or at most 6, 7, 8, 9, 10, 15, 20, 25, 30, 40, 50, or at least 60 amino acids.

In an embodiment, an exogenous protease cleavage site is located within the di-chain loop of a TVEMP. In aspects of this embodiment, a TVEMP comprises an exogenous protease cleavage site comprises, e.g., a plant papain cleavage site, an insect papain cleavage site, a crustacian papain cleavage site, a non-human enterokinase protease cleavage site, a Tobacco Etch Virus protease cleavage site, a Tobacco Vein Mottling Virus protease cleavage site, a human rhinovirus 3C protease cleavage site, a human enterovirus 3C protease cleavage site, a subtilisin cleavage site, a hydroxylamine cleavage site, a SUMO/ULP-1 protease cleavage site, and a non-human Caspase 3 cleavage site. In other aspects of this embodiment, an exogenous protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In an aspect of this embodiment, an exogenous protease cleavage site can comprise, e.g., a non-human enterokinase cleavage site is located within the di-chain loop of a TVEMP. In other aspects of the embodiment, an exogenous protease cleavage site can comprise, e.g., a bovine enterokinase protease cleavage site located within the di-chain loop of a TVEMP. In other aspects of the embodiment, an exogenous protease cleavage site can comprise, e.g., a bovine enterokinase protease cleavage site located within the di-chain loop of a TVEMP comprises SEQ ID NO: 21. In still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In another aspect of this embodiment, an exogenous protease cleavage site can comprise, e.g., a Tobacco Etch Virus protease cleavage site is located within the di-chain loop of a TVEMP. In other aspects of the embodiment, an exogenous protease cleavage site can comprise, e.g., a Tobacco Etch Virus protease cleavage site located within the di-chain loop of a TVEMP comprises the consensus sequence E-P5-P4-Y-P2-Q*-G (SEQ ID NO: 22) or E-P5-P4-Y-P2-Q*-S (SEQ ID NO: 23), where P2, P4 and P5 can be any amino acid. In other aspects of the embodiment, an exogenous protease cleavage site can comprise, e.g., a Tobacco Etch Virus protease cleavage site located within the di-chain loop of a TVEMP comprises SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In still other aspects of this embodiment, a Tobacco Etch Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In another aspect of this embodiment, an exogenous protease cleavage site can comprise, e.g., a Tobacco Vein Mottling Virus protease cleavage site is located within the di-chain loop of a TVEMP. In other aspects of the embodiment, an exogenous protease cleavage site can comprise, e.g., a Tobacco Vein Mottling Virus protease cleavage site located within the di-chain loop of a TVEMP comprises the consensus sequence P6-P5-V-R-F-Q*-G (SEQ ID NO: 34) or P6-P5-V-R-F-Q*-S (SEQ ID NO: 35), where P5 and P6 can be any amino acid. In other aspects of the embodiment, an exogenous protease cleavage site can comprise, e.g., a Tobacco Vein Mottling Virus protease cleavage site located within the di-chain loop of a TVEMP comprises SEQ ID NO: 36, SEQ ID NO: 37, SEQ ID NO: 38, or SEQ ID NO: 39. In still other aspects of this embodiment, a Tobacco Vein Mottling Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In still another aspect of this embodiment, an exogenous protease cleavage site can comprise, e.g., a human rhinovirus 3C protease cleavage site is located within the di-chain loop of a TVEMP. In other aspects of the embodiment, an exogenous protease cleavage site can comprise, e.g., a human rhinovirus 3C protease cleavage site located within the di-chain loop of a TVEMP comprises the consensus sequence P5-P4-L-F-Q*-G-P (SEQ ID NO: 40), where P4 is G, A, V, L, I, M, S or T and P5 can any amino acid, with D or E preferred. In other aspects of the embodiment, an exogenous protease cleavage site can comprise, e.g., a human rhinovirus 3C protease cleavage site located within the di-chain loop of a TVEMP comprises SEQ ID NO: 41, SEQ ID NO: 42, SEQ ID NO: 43, SEQ ID NO: 44, SEQ ID NO: 45 or SEQ ID NO: 46. In other aspects of the embodiment, an exogenous protease cleavage site can comprise, e.g., a human rhinovirus 3C protease located within the di-chain loop of a TVEMP that can be cleaved by PRESCISSION®, a modified human rhinovirus 3C protease (GE Healthcare Biosciences, Piscataway, N.J.). In still other aspects of this embodiment, a human rhinovirus 3C protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a subtilisin cleavage site is located within the di-chain loop of a TVEMP. In other aspects of the embodiment, an exogenous protease cleavage site can comprise, e.g., a subtilisin cleavage site located within the di-chain loop of a TVEMP comprises the consensus sequence P6-P5-P4-P3-H*-Y (SEQ ID NO: 47) or P6-P5-P4-P3-Y-H* (SEQ ID NO: 48), where P3, P4 and P5 and P6 can be any amino acid. In other aspects of the embodiment, an exogenous protease cleavage site can comprise, e.g., a subtilisin cleavage site located within the di-chain loop of a TVEMP comprises SEQ ID NO: 49, SEQ ID NO: 50, or SEQ ID NO: 51. In other aspects of the embodiment, an exogenous protease cleavage site can comprise, e.g., a subtilisin cleavage site located within the di-chain loop of a TVEMP that can be cleaved by GENENASE®, a modified subtilisin (New England Biolabs, Ipswich, Mass.). In still other aspects of this embodiment, a subtilisin cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a hydroxylamine cleavage site is located within the di-chain loop of a TVEMP. In other aspects of the embodiment, an exogenous protease cleavage site can comprise, e.g., a hydroxylamine cleavage site comprising multiples of the dipeptide N*G. In other aspects of the embodiment, an exogenous protease cleavage site can comprise, e.g., a hydroxylamine cleavage site located within the di-chain loop of a TVEMP comprises SEQ ID NO: 52, or SEQ ID NO: 53. In still other aspects of this embodiment, a hydroxylamine cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a SUMO/ULP-1 protease cleavage site is located within the di-chain loop of a TVEMP. In other aspects of the embodiment, an exogenous protease cleavage site can comprise, e.g., a SUMO/ULP-1 protease cleavage site located within the di-chain loop of a TVEMP comprising the consensus sequence G-G*-P1'-P2'-P3' (SEQ ID NO: 54), where P1', P2', and P3' can be any amino acid. In other aspects of the embodiment, an exogenous protease cleavage site can comprise, e.g., a SUMO/ULP-1 protease cleavage site located within the di-chain loop of a TVEMP comprises SEQ ID NO: 55. In still other aspects of this embodiment, a SUMO/ULP-1 protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In an aspect of this embodiment, an exogenous protease cleavage site can comprise, e.g., a non-human Caspase 3 cleavage site is located within the di-chain loop of a TVEMP. In other aspects of the embodiment, an exogenous protease cleavage site can comprise, e.g., a mouse Caspase 3 protease cleavage site located within the di-chain loop of a TVEMP. In other aspects of the embodiment, an exogenous protease cleavage site can comprise, e.g., a non-human Caspase 3 protease cleavage site located within the di-chain loop of a TVEMP comprises the consensus sequence D-P3-P2-D*P1' (SEQ ID NO: 56), where P3 can be any amino acid, with E preferred, P2 can be any amino acid and P1' can any amino acid, with G or S preferred. In other aspects of the embodiment, an exogenous protease cleavage site can comprise, e.g., a non-human Caspase 3 protease cleavage site located within the di-chain loop of a TVEMP comprising SEQ ID NO: 57, SEQ ID NO: 58, SEQ ID NO: 59, SEQ ID NO: 60, SEQ ID NO: 61, or SEQ ID NO: 62. In still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

A di-chain loop region is modified to replace a naturally-occurring di-chain loop protease cleavage site for an exogenous protease cleavage site. In this modification, the naturally-occurring di-chain loop protease cleavage site is made inoperable and thus can not be cleaved by its protease. Only the exogenous protease cleavage site can be cleaved by its corresponding exogenous protease. In this type of modification, the exogenous protease site is operably-linked in-frame to a TVEMP as a fusion protein and the site can be cleaved by its respective exogenous protease. Replacement of an endogenous di-chain loop protease cleavage site with an exogenous protease cleavage site can be a substitution of the sites where the exogenous site is engineered at the position approximating the cleavage site location of the endogenous site. Replacement of an endogenous di-chain loop protease cleavage site with an exogenous protease cleavage site can be an addition of an exogenous site where the exogenous site is engineered at the position different from the cleavage site location of the endogenous site, the endogenous site being engineered to be inoperable. The location and kind of protease cleavage site may be critical because certain binding domains require a free amino-terminal or carboxyl-terminal amino acid. For example, when a retargeted peptide binding domain is placed between two other domains, e.g., see FIG. 4, a criterion for selection of a protease cleavage site could be whether the protease that cleaves its site leaves a flush cut, exposing the free amino-terminal or carboxyl-terminal of the binding domain necessary for selective binding of the binding domain to its receptor.

A naturally-occurring protease cleavage site can be made inoperable by altering at least the two amino acids flanking the peptide bond cleaved by the naturally-occurring di-chain loop protease. More extensive alterations can be made, with the proviso that the two cysteine residues of the di-chain loop region remain intact and the region can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering the two amino acids flanking the peptide bond cleaved by a naturally-occurring protease. In other aspects of this embodiment, a naturally-occurring protease cleavage site is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

It is understood that a TVEMP disclosed in the present specification can optionally further comprise a flexible region comprising a flexible spacer. A flexible region comprising flexible spacers can be used to adjust the length of a polypeptide region in order to optimize a characteristic, attribute or property of a polypeptide. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present a retargeted peptide binding domain, thereby facilitating the binding of that binding domain to its receptor.

A flexible space comprising a peptide is at least one amino acid in length and comprises non-charged amino acids with small side-chain R groups, such as, e.g., glycine, alanine, valine, leucine or serine. Thus, in an embodiment a flexible spacer can have a length of, e.g., at least 1, 2, 3, 4, 5, 6, 7, 8, 9, or 10 amino acids; or at most 1, 2, 3, 4, 5, 6, 7, 8, 9, or 10 amino acids. In still another embodiment, a flexible spacer can be, e.g., between 1-3 amino acids, between 2-4 amino acids, between 3-5 amino acids, between 4-6 amino acids, or between 5-7 amino acids. Non-limiting examples of a flexible spacer include, e.g., a G-spacers such as GGG, GGGG (SEQ ID NO: 63), and GGGGS (SEQ ID NO: 64) or an A-spacers such as AAA, AAAA (SEQ ID NO: 65) and AAAAV (SEQ ID NO: 66). Such a flexible region is operably-linked in-frame to the TVEMP as a fusion protein.

Thus, in an embodiment, a TVEMP disclosed in the present specification can further comprise a flexible region comprising a flexible spacer. In another embodiment, a TVEMP disclosed in the present specification can further comprise flexible region comprising a plurality of flexible spacers in tandem. In aspects of this embodiment, a flexible region can comprise in tandem, e.g., at least 1, 2, 3, 4, or 5 G-spacers; or at most 1, 2, 3, 4, or 5 G-spacers. In still other aspects of this embodiment, a flexible region can comprise in tandem, e.g., at least 1, 2, 3, 4, or 5 A-spacers; or at most 1, 2, 3, 4, or 5 A-spacers. In another aspect of this embodiment, a TVEMP can comprise a flexible region comprising one or more copies of the same flexible spacers, one or more copies of different flexible-spacer regions, or any combination thereof.

In other aspects of this embodiment, a TVEMP comprising a flexible spacer can be, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

It is envisioned that a TVEMP disclosed in the present specification can comprise a flexible spacer in any and all locations with the proviso that TVEMP is capable of performing the intoxication process. In aspects of this embodiment, a flexible spacer is positioned between, e.g., an enzymatic domain and a translocation domain, an enzymatic domain and a retargeted peptide binding domain, an enzymatic domain and an exogenous protease cleavage site. In other aspects of this embodiment, a G-spacer is positioned between, e.g., an enzymatic domain and a translocation domain, an enzymatic domain and a retargeted peptide binding domain, an enzymatic domain and an exogenous protease cleavage site. In other aspects of this embodiment, an A-spacer is positioned between, e.g., an enzymatic domain and a translocation domain, an enzymatic domain and a retargeted peptide binding domain, an enzymatic domain and an exogenous protease cleavage site.

In other aspects of this embodiment, a flexible spacer is positioned between, e.g., a retargeted peptide binding domain and a translocation domain, a retargeted peptide binding domain and an enzymatic domain, a retargeted peptide binding domain and an exogenous protease cleavage site. In other aspects of this embodiment, a G-spacer is positioned between, e.g., a retargeted peptide binding domain and a translocation domain, a retargeted peptide binding domain and an enzymatic domain, a retargeted peptide binding domain and an exogenous protease cleavage site. In other aspects of this embodiment, an A-spacer is positioned between, e.g., a retargeted peptide binding domain and a translocation domain, a retargeted peptide binding domain and an enzymatic domain, a retargeted peptide binding domain and an exogenous protease cleavage site.

In yet other aspects of this embodiment, a flexible spacer is positioned between, e.g., a translocation domain and an enzymatic domain, a translocation domain and a retargeted peptide binding domain, a translocation domain and an exogenous protease cleavage site. In other aspects of this embodiment, a G-spacer is positioned between, e.g., a translocation domain and an enzymatic domain, a translocation domain and a retargeted peptide binding domain, a translocation domain and an exogenous protease cleavage site. In other aspects of this embodiment, an A-spacer is positioned between, e.g., a translocation domain and an enzymatic domain, a translocation domain and a retargeted peptide binding domain, a translocation domain and an exogenous protease cleavage site.

It is envisioned that a TVEMP disclosed in the present specification can comprise a retargeted peptide binding domain in any and all locations with the proviso that TVEMP is capable of performing the intoxication process. Non-limiting examples include, locating a retargeted peptide binding domain at the amino terminus of a TVEMP; locating a retargeted peptide binding domain between a Clostridial toxin enzymatic domain and a translocation domain of a TVEMP; and locating a retargeted peptide binding domain at the carboxyl terminus of a TVEMP. Other non-limiting examples include, locating a retargeted peptide binding domain between a Clostridial toxin enzymatic domain and a Clostridial toxin translocation domain of a TVEMP. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a retargeted peptide binding domain is in the amino-terminal position, an amino acid sequence comprising a start methionine and a protease cleavage site may be operably-linked in situations in which a retargeted peptide binding domain requires a free amino terminus, see, e.g., Shengwen Li et al., *Degradable Clostridial Toxins*, U.S. patent application Ser. No. 11/572,512 (Jan. 23, 2007), which is hereby incorporated by reference in its entirety. In addition, it is known in the art that when adding a polypeptide that is operably-linked to the amino terminus of another polypeptide comprising the start methionine that the original methionine residue can be deleted.

Figure 3A:
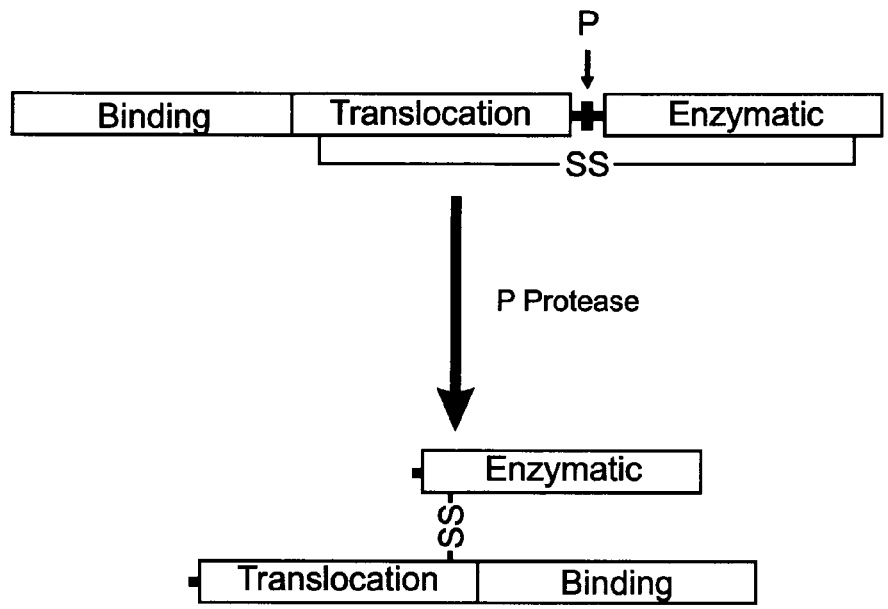
FIG. 3A depicts the single-chain polypeptide form of a TVEMP with an amino to carboxyl linear organization comprising a binding element, a translocation element, a di-chain loop region comprising an exogenous protease cleavage site (P), and a therapeutic element. Upon proteolytic cleavage with a P protease, the single-chain form of the toxin is converted to the di-chain form.

Thus, in an embodiment, a TVEMP can comprise an amino to carboxyl single polypeptide linear order comprising a retargeted peptide binding domain, a translocation domain, an exogenous protease cleavage site and an enzymatic domain (FIG. 3A). In an aspect of this embodiment, a TVEMP can comprise an amino to carboxyl single polypeptide linear order comprising a retargeted peptide binding domain, a Clostridial toxin translocation domain, an exogenous protease cleavage site and a Clostridial toxin enzymatic domain.

Figure 3B:
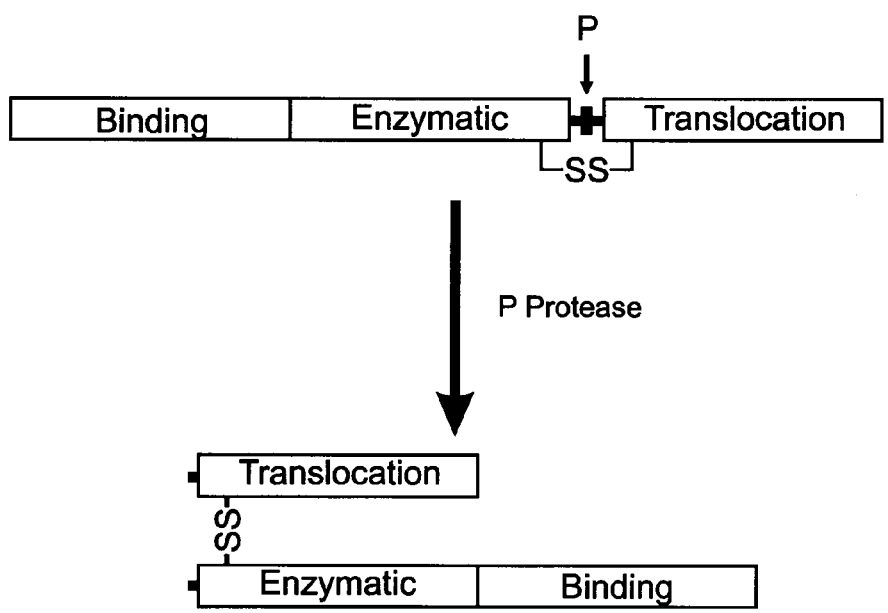
FIG. 3B depicts the single polypeptide form of a TVEMP with an amino to carboxyl linear organization comprising a binding element, a therapeutic element, a di-chain loop region comprising an exogenous protease cleavage site (P), and a translocation element. Upon proteolytic cleavage with a P protease, the single-chain form of the toxin is converted to the di-chain form.

In another embodiment, a TVEMP can comprise an amino to carboxyl single polypeptide linear order comprising a retargeted peptide binding domain, an enzymatic domain, an exogenous protease cleavage site, and a translocation domain (FIG. 3B). In an aspect of this embodiment, a TVEMP can comprise an amino to carboxyl single polypeptide linear order comprising a retargeted peptide binding domain, a Clostridial toxin enzymatic domain, an exogenous protease cleavage site, a Clostridial toxin translocation domain.

Figure 4A:
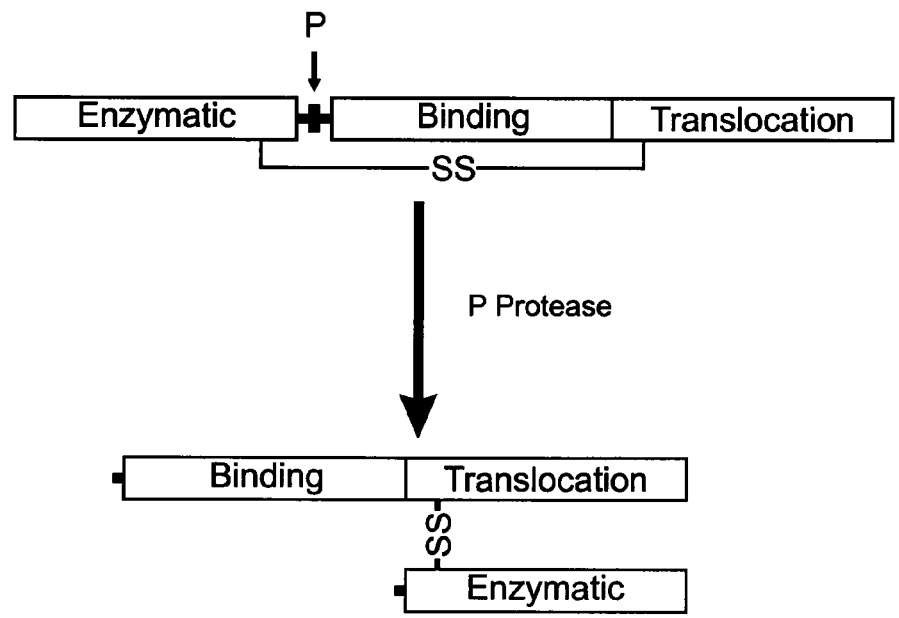
FIG. 4A depicts the single polypeptide form of a TVEMP with an amino to carboxyl linear organization comprising a therapeutic element, a di-chain loop region comprising an exogenous protease cleavage site (P), a binding element, and a translocation element. Upon proteolytic cleavage with a P protease, the single-chain form of the toxin is converted to the di-chain form.

In yet another embodiment, a TVEMP can comprise an amino to carboxyl single polypeptide linear order comprising an enzymatic domain, an exogenous protease cleavage site, a retargeted peptide binding domain, and a translocation domain (FIG. 4A). In an aspect of this embodiment, a TVEMP can comprise an amino to carboxyl single polypeptide linear order comprising a Clostridial toxin enzymatic domain, an exogenous protease cleavage site, a retargeted peptide binding domain, and a Clostridial toxin translocation domain.

Figure 4B:
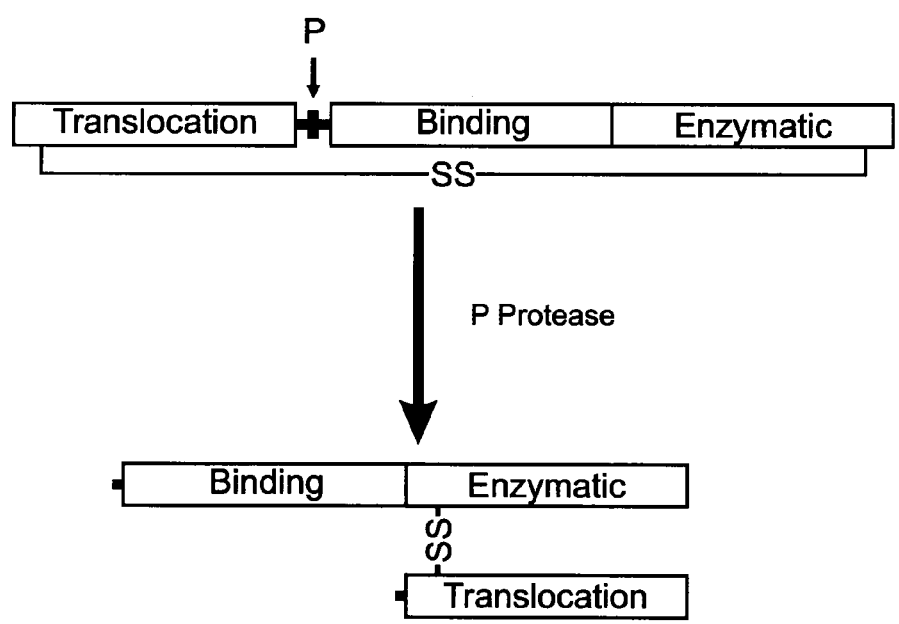
FIG. 4B depicts the single polypeptide form of a TVEMP with an amino to carboxyl linear organization comprising a translocation element, a di-chain loop region comprising an exogenous protease cleavage site (P), a binding element, and a therapeutic element. Upon proteolytic cleavage with a P protease, the single-chain form of the toxin is converted to the di-chain form.

In yet another embodiment, a TVEMP can comprise an amino to carboxyl single polypeptide linear order comprising a translocation domain, an exogenous protease cleavage site, a retargeted peptide binding domain, and an enzymatic domain (FIG. 4B). In an aspect of this embodiment, a TVEMP can comprise an amino to carboxyl single polypeptide linear order comprising a Clostridial toxin translocation domain, a retargeted peptide binding domain, an exogenous protease cleavage site and a Clostridial toxin enzymatic domain.

Figure 4C:
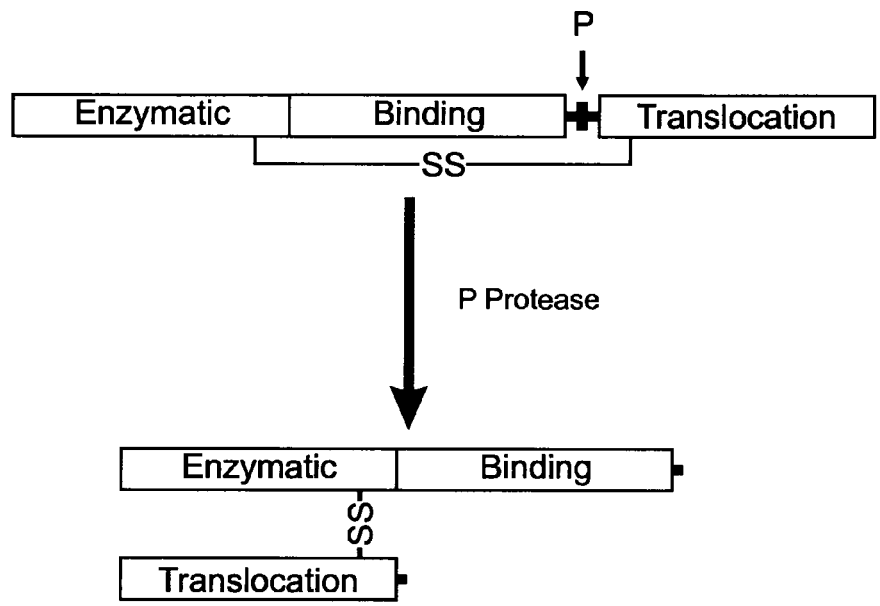
FIG. 4C depicts the single polypeptide form of a TVEMP with an amino to carboxyl linear organization comprising a therapeutic element, a binding element, a di-chain loop region comprising an exogenous protease cleavage site (P), and a translocation element. Upon proteolytic cleavage with a P protease, the single-chain form of the toxin is converted to the di-chain form.

In another embodiment, a TVEMP can comprise an amino to carboxyl single polypeptide linear order comprising an enzymatic domain, a retargeted peptide binding domain, an exogenous protease cleavage site, and a translocation domain (FIG. 4C). In an aspect of this embodiment, a TVEMP can comprise an amino to carboxyl single polypeptide linear order comprising a Clostridial toxin enzymatic domain, a retargeted peptide binding domain, an exogenous protease cleavage site, a Clostridial toxin translocation domain.

Figure 4D:
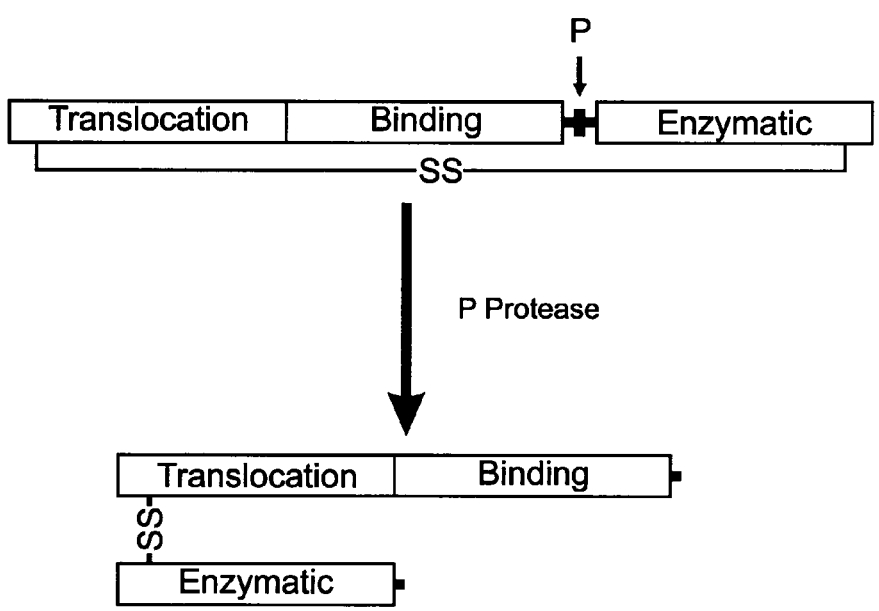
FIG. 4D depicts the single polypeptide form of a TVEMP with an amino to carboxyl linear organization comprising a translocation element, a binding element, a di-chain loop region comprising an exogenous protease cleavage site (P), and a therapeutic element. Upon proteolytic cleavage with a P protease, the single-chain form of the toxin is converted to the di-chain form.

In yet another embodiment, a TVEMP can comprise an amino to carboxyl single polypeptide linear order comprising a translocation domain, a retargeted peptide binding domain, an exogenous protease cleavage site and an enzymatic domain (FIG. 4D). In an aspect of this embodiment, a TVEMP can comprise an amino to carboxyl single polypeptide linear order comprising a Clostridial toxin translocation domain, a retargeted peptide binding domain, an exogenous protease cleavage site and a Clostridial toxin enzymatic domain.

Figure 5A:
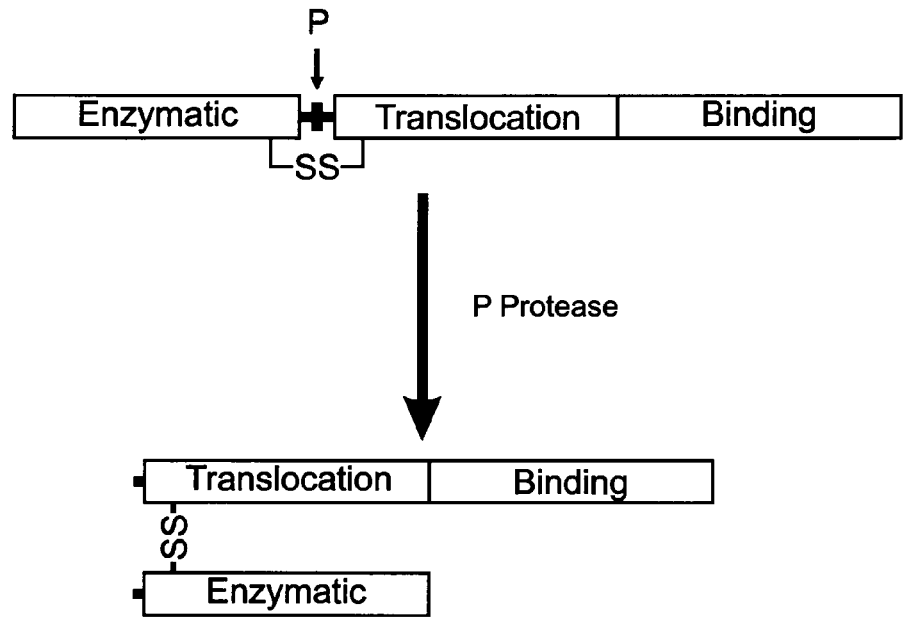
FIG. 5A depicts the single polypeptide form of a TVEMP with an amino to carboxyl linear organization comprising a therapeutic element, a di-chain loop region comprising an exogenous protease cleavage site (P), a translocation element, and a binding element. Upon proteolytic cleavage with a P protease, the single-chain form of the toxin is converted to the di-chain form.

In still another embodiment, a TVEMP can comprise an amino to carboxyl single polypeptide linear order comprising an enzymatic domain, an exogenous protease cleavage site, a translocation domain, and a retargeted peptide binding domain (FIG. 5A). In an aspect of this embodiment, a TVEMP can comprise an amino to carboxyl single polypeptide linear order comprising a Clostridial toxin enzymatic domain, an exogenous protease cleavage site, a Clostridial toxin translocation domain, and a retargeted peptide binding domain.

Figure 5B:
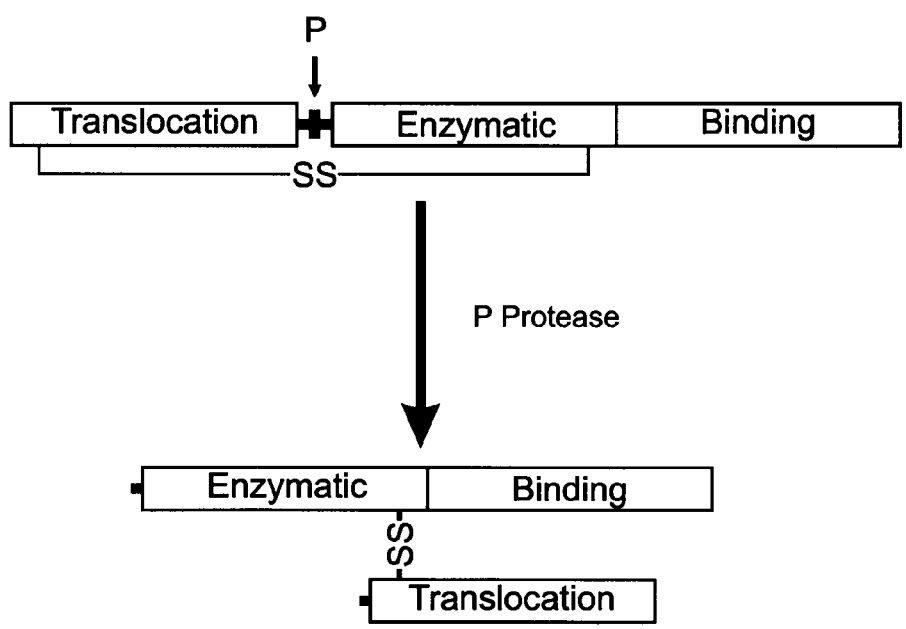
FIG. 5B depicts the single polypeptide form of a TVEMP with an amino to carboxyl linear organization comprising a translocation element, a di-chain loop region comprising an exogenous protease cleavage site (P), a therapeutic element, and a binding element. Upon proteolytic cleavage with a P protease, the single-chain form of the toxin is converted to the di-chain form.

In still another embodiment, a TVEMP can comprise an amino to carboxyl single polypeptide linear order comprising a translocation domain, an exogenous protease cleavage site, an enzymatic domain and a retargeted peptide binding domain, (FIG. 5B). In an aspect of this embodiment, a TVEMP can comprise an amino to carboxyl single polypeptide linear order comprising a Clostridial toxin translocation domain, a retargeted peptide binding domain, an exogenous protease cleavage site and a Clostridial toxin enzymatic domain.

A composition useful in the invention generally is administered as a pharmaceutical acceptable composition comprising a TVEMP. As used herein, the term "pharmaceutically acceptable" refers to any molecular entity or composition that does not produce an adverse, allergic or other untoward or unwanted reaction when administered to an individual. As used herein, the term "pharmaceutically acceptable composition" is synonymous with "pharmaceutical composition" and refers to a therapeutically effective concentration of an active ingredient, such as, e.g., any of the TVEMPs disclosed in the present specification. A pharmaceutical composition comprising a TVEMP is useful for medical and veterinary applications. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

Aspects of the present invention provide, in part, a composition comprising a TVEMP. It is envisioned that any of the composition disclosed in the present specification can be useful in a method of treating urogenital-neurological disorder in a mammal in need thereof, with the proviso that the composition prevents or reduces a symptom associated with the urogenital-neurological disorder. Non-limiting examples of compositions comprising a TVEMP include a TVEMP comprising a retargeted peptide binding domain, a Clostridial toxin translocation domain and a Clostridial toxin enzymatic domain. It is envisioned that any TVEMP disclosed in the present specification can be used, including those disclosed in, e.g., Steward, supra, (2007); Dolly, supra, (2007); Foster, supra, WO 2006/059093 (2006); Foster, supra, WO 2006/059105 (Jun. 8, 2006). It is also understood that the two or more different TVEMPs can be provided as separate compositions or as part of a single composition.

It is also envisioned that a pharmaceutical composition comprising a TVEMP can optionally include a pharmaceutically acceptable carriers that facilitate processing of an active ingredient into pharmaceutically acceptable compositions. As used herein, the term "pharmacologically acceptable carrier" is synonymous with "pharmacological carrier" and refers to any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, $7^{th}$ ed. 1999); REMINGTON: THE SCIENCE AND PRACTICE OF PHARMACY (Alfonso R. Gennaro ed., Lippincott, Williams & Wilkins, $20^{th}$ ed. 2000); GOODMAN & GILMAN'S THE PHARMACOLOGICAL BASIS OF THERAPEUTICS (Joel G. Hardman et al., eds., McGraw-Hill Professional, $10^{th}$ ed. 2001); and HANDBOOK OF PHARMACEUTICAL EXCIPIENTS (Raymond C. Rowe et al., APhA Publications, $4^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and methods for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

In an embodiment, a composition comprising a TVEMP is a pharmaceutical composition comprising a TVEMP. In aspects of this embodiment, a pharmaceutical composition comprising a TVEMP further comprises a pharmacological carrier, a pharmacological component, or both a pharmacological carrier and a pharmacological component. In other aspects of this embodiment, a pharmaceutical composition comprising a TVEMP further comprises at least one pharmacological carrier, at least one pharmacological component, or at least one pharmacological carrier and at least one pharmaceutical component.

Aspects of the present invention provide, in part, an urogenital-neurological disorder. As used herein, the term "urogenital-neurological disorder" refers to an urogenital-rooted disorder where at least one of the underlying symptoms being treated is due to a nerve-based etiology, such as, e.g., a spastic dysfunction and/or degeneration of the sacral reflex arcs. Non-limiting examples of urogenital-neurological disorders, include, without limitation, urinary incontinence, overactive bladder, detrusor dysfunction, lower urinary tract dysfunction, urinary retention, urinary hesitancy, polyuria, nocturia, chronic urinary tract infection, prostate disorders associated with or without other urogenital disorders, uterine disorders associated with or without other urogenital disorders, and urogenital disorders associated with neurogenic dysfunction (such as, e.g., urogenital disorders associated with Parkinson's Disease, multiple sclerosis, spina bifida, transverse myelitis, stroke, spinal cord injury, spasm reflex, and a neurologic lesion of the spinal cord or brain), and other such urogenital disorders of a nerve-based etiology.

An individual's ability to hold urine and maintain continence depends on normal function of the lower urinary tract, the kidneys, and the nervous system. The individual must also have a physical and psychological ability to recognize and appropriately respond to the urge to urinate. The bladder's ability to fill and store urine requires a functional sphincter muscle (which controls the flow of urine out of the body) and a stable bladder wall muscle (detrusor). Normal bladder function is dependent on the nerves that sense the fullness of the bladder and on those that trigger the muscle movements that either empty it or retain urine. The process of urination involves two phases: 1) filling and storage of bladder and 2) emptying of bladder. During the filling and storage phase, the bladder stretches so it can hold the increasing amount of urine. The bladder of an average person can hold 350 mL to 550 mL of urine. Generally, the reflex to urinate is triggered when the bladder of an individual when approximately 200 mL of urine collects in the bladder. The emptying phase requires that the detrusor muscle contract, forcing urine out of the bladder through the urethra. The sphincter muscle must relax at the same time, so that urine can flow out of the body. The bladder, internal sphincters, and external sphincters may all be affected by nerve-based disorders that create abnormalities in bladder function. The damage can cause the bladder to be underactive, in which it is unable to contract and unable to empty completely, or it can be overactive, in which it contracts too quickly or frequently.

One type of urogenital-neurological disorder is urinary incontinence. Urinary incontinence is the inability to control the passage of urine. This can range from an occasional leakage of urine, to a complete inability to hold any urine. Urinary incontinence can be caused by abnormalities in bladder capacity or malfunction of control mechanisms such as the bladder neck and/or external urethral sphincter muscle that are important for the bladder's storage function. The many types of urinary incontinence.

Stress incontinence is a type of urinary incontinence in which the strength of the muscles (urethral sphincter) that help control urination is reduced as a result of weakened pelvic muscles that support the bladder and urethra or because of malfunction of the urethral sphincter. The weakness may be caused by prior injury to the urethral area, neurological injury, some medications, or after surgery of the prostate or pelvic area. The sphincter is not able to prevent urine flow when there is increased pressure from the abdomen such as during certain activities like coughing, sneezing, laughing, or exercise. Stress urinary incontinence is the most common type of urinary incontinence in women. Studies have shown about 50% of all women have occasional urinary incontinence, and as many as 10% have frequent incontinence. Nearly 20% of women over age 75 experience daily urinary incontinence. Stress incontinence is often seen in women who have had multiple pregnancies and vaginal childbirths, whose bladder, urethra, or rectal wall stick out into the vaginal space (pelvic prolapse).

Urge incontinence is a type of urinary incontinence that involves a strong, sudden need to urinate, followed by instant bladder contraction and involuntary loss of urine which results in leakage. There is not enough time between when an individual suffering from urge incontinence recognizes the need to urinate and when urination actually occurs. Urge incontinence is leakage of urine due to bladder muscles that contract inappropriately. Often these contractions occur regardless of the amount of urine that is in the bladder. Urge incontinence may result from neurological injuries (such as spinal cord injury or stroke), neurological dysfunction (such as, e.g., Parkinson's Disease and multiple sclerosis), infection, bladder cancer, bladder stones, bladder inflammation, or bladder outlet obstruction. In men, urge incontinence may be due to neurological disease or bladder changes caused by benign prostatic hypertrophy (BPH) or bladder outlet obstruction from an enlarged prostate. The majority of cases of urge incontinence are idiopathic, meaning a specific cause cannot be identified. Although urge incontinence may occur in anyone at any age, it is more common in women and the elderly. Urge incontinence is also known as irritable bladder, spasmodic bladder, and unstable bladder.

Overflow urinary incontinence happens when small amounts of urine leak from a bladder that is always full. In older men, this can occur when the flow of urine from the bladder is blocked, usually by an enlarged prostate. It can sometimes be prevented by medication when early symptoms of prostate enlargement, such as frequent urination, appear. Some people with diabetes also have overflow incontinence. Mixed urinary incontinence describes a disorder where an individual exhibits symptoms associated with both stress incontinence and urge incontinence. Continuous urinary incontinence is the complaint of continuous leakage.

Thus, in an embodiment, a mammal suffering from urinary incontinence is treated with a composition comprising a therapeutically effective amount of a TVEMP where such administration reduces a symptom associated with the urinary incontinence. In an aspect of this embodiment, a mammal suffering from stress incontinence is treated with a composition comprising a therapeutically effective amount of a TVEMP where such administration reduces a symptom associated with the stress incontinence. In another aspect of this embodiment, a mammal suffering from urge incontinence is treated with a composition comprising a therapeutically effective amount of a TVEMP where such administration reduces a symptom associated with the urge incontinence. In still another aspect of this embodiment, a mammal suffering from overflow urinary incontinence is treated with a composition comprising a therapeutically effective amount of a TVEMP where such administration reduces a symptom associated with the overflow urinary incontinence. In a further aspect of this embodiment, a mammal suffering from mixed urinary incontinence is treated with a composition comprising a therapeutically effective amount of a TVEMP where such administration reduces a symptom associated with the mixed urinary incontinence. In a further aspect of this embodiment, a mammal suffering from continuous urinary incontinence is treated with a composition comprising a therapeutically effective amount of a TVEMP where such administration reduces a symptom associated with the continuous urinary incontinence.

Another type of urogenital-neurological disorder is overactive bladder. Overactive bladder is increased urinary urgency, with or without urge urinary incontinence, usually with frequency and nocturia. The individual may report symptoms of urinary urgency (the sudden, intense desire to urinate immediately), urinary frequency (the need to urinate more times than is normal), enuresis (any involuntary loss of urine), polyuria, nocturia, and/or urinary incontinence. Thus, overactive bladder describes a bladder that contracts more often than it should, so that a person feels the need to urinate more frequently and/or urgently than necessary and is characterized by uncontrolled, frequent expulsion of urine from the bladder. An overactive bladder usually, but not always, causes urinary incontinence. Individuals with overactive bladder may go to the bathroom very often, e.g., every two hours during the day and night, and may even wet the bed. Often, a strong urge to void is experienced when only a small amount of urine is in the bladder. There may be reduced bladder capacity and incomplete emptying of urine. An overactive bladder can be caused by interruptions in the nerve pathways to the bladder occurring above the sacrum. For example, spastic bladder may be caused by an inability of the detrusor muscle of the bladder to inhibit emptying contractions until a reasonable amount of urine has accumulated. As such, overactive bladder is often associated with detrusor overactivity, a pattern of bladder muscle contraction observed during urodynamics. Overactive bladder can also be caused by urinary tract infection, outflow obstruction and stress incontinence. Sometimes no cause is found, and such idiopathic cases may be due to anxiety or aging. Symptoms include the need to urinate may times throughout the day and night, the sensation of having to urinate immediately, and/or the sudden leakage of urine from the bladder.

Diseases extrinsic to the bladder may also cause the symptoms of overactive bladder. In the male patient, the extrinsic disorder most often responsible for overactive bladder is bladder outlet obstruction (BOO). Disorders extrinsic to the bladder in the female patient include urethral diverticulum, retroverted uterus, pelvic prolapse (including cystocele), gravid uterus, and loss or reduction of estrogen. Disorders extrinsic to the bladder common to both men and woman include pelvic mass, physiologic nocturnal diuresis, and polyuria caused by factors such as excessive fluid intake, diuretic use, or diabetes. Neuromuscular disorders may also account for the overactive bladder. Neurogenic disorders resulting from nerve damage can also cause overactive bladder, including, without limitation, Parkinson disease, multiple sclerosis, spina bifida, cervical stenosis, spinal cord injury, diabetic neuropathy, pelvic surgery, or invertebral disc herniation, hydrocephalus, stroke, spinal cord injuries and lesions of the spinal cord or brain. Bladder aging may also account for these symptoms. A patient history of pelvic trauma, pelvic radiation, or bladder, prostate, or urethral surgery should also be considered when seeking to determine the etiology of the overactive bladder.

Thus, in an embodiment, a mammal suffering from overactive bladder is treated with a composition comprising a therapeutically effective amount of a TVEMP where such administration reduces a symptom associated with the overactive bladder. In an aspect of this embodiment, a mammal suffering from overactive bladder is treated with a composition comprising a therapeutically effective amount of a TVEMP where such administration reduces incontinence, reduces urinary frequency, reduces urinary urgency, reduces enuresis, reduces polyuria, reduces nocturia, and/or reduces urinary incontinence.

Another type of urogenital-neurological disorder is detrusor dysfunction, including, without limitation, detrusor overactivity, detrusor instability, and detrusor-sphincter dyssynergia. One kind of detrusor dysfunction is detrusor overactivity or involuntary detrusor contractions (previously termed detrusor hyperreflexia). Detrusor overactivity involves increased involuntary contractions of the detrusor muscle during the filling phase which may be spontaneous or provoked resulting in uninhibitable bladder contractions. The muscle contraction patterns of detrusor overactivity include, without limitation, phasic detrusor overactivity and terminal detrusor overactivity. Detrusor overactivity can be either idiopathic in nature or they can be caused by non-neurogenic or neurogenic conditions. Symptoms of detrusor overactivity include, without limitation, uninhibitable bladder contractions, urinary urgency, urinary frequency, enuresis, polyuria, nocturia, and/or urinary incontinence. Another kind of detrusor dysfunction is detrusor instability. Detrusor instability involves uncontrolled involuntary contractions of the detrusor muscle resulting in uninhibitable bladder contractions irrespective of bladder capacity. Symptoms of detrusor instability include, without limitation, uninhibitable bladder contractions, urinary urgency, urinary frequency, enuresis, polyuria, nocturia, and/or urinary incontinence. Another kind of detrusor dysfunction is detrusor-sphincter dyssynergia (DSD). Detrusor-sphincter dyssynergia occurs when the contraction of the detrusor musculature is not coordinated with the relaxation of the sphincter thereby preventing the urethra from relaxing completely during voiding. Symptoms of detrusor-sphincter dyssynergia include, without limitation, urine flow interruption, raised detrusor pressure and/or urinary retention. DSD can be caused as a consequence of a neurological condition such as spinal injury or multiple sclerosis.

Thus, in an embodiment, a mammal suffering from detrusor dysfunction is treated with a composition comprising a therapeutically effective amount of a TVEMP where such administration reduces a symptom associated with the detrusor dysfunction. In an aspect of this embodiment, a mammal suffering from detrusor dysfunction is treated with a composition comprising a therapeutically effective amount of a TVEMP where such administration reduces uninhibitable bladder contractions, reduces urinary frequency, reduces urinary urgency, reduces enuresis, reduces polyuria, reduces nocturia, reduces urinary incontinence, reduces urine flow interruption, reduces detrusor pressure, and/or reduces urinary retention.

In another embodiment, a mammal suffering from detrusor overactivity is treated with a composition comprising a therapeutically effective amount of a TVEMP where such administration reduces a symptom associated with the detrusor overactivity. In an aspect of this embodiment, a mammal suffering from detrusor overactivity is treated with a composition comprising a therapeutically effective amount of a TVEMP where such administration reduces uninhibitable bladder contractions, reduces urinary frequency, reduces urinary urgency, reduces enuresis, reduces polyuria, reduces nocturia, and/or reduces urinary incontinence.

In yet another embodiment, a mammal suffering from detrusor instability is treated with a composition comprising a therapeutically effective amount of a TVEMP where such administration reduces a symptom associated with the detrusor instability. In an aspect of this embodiment, a mammal suffering from detrusor instability is treated with a composition comprising a therapeutically effective amount of a TVEMP where such administration reduces uninhibitable bladder contractions, reduces urinary frequency, reduces urinary urgency, reduces enuresis, reduces polyuria, reduces nocturia, and/or reduces urinary incontinence.

In still another embodiment, a mammal suffering from detrusor-sphincter dyssynergia is treated with a composition comprising a therapeutically effective amount of a TVEMP where such administration reduces a symptom associated with the detrusor-sphincter dyssynergia. In an aspect of this embodiment, a mammal suffering from detrusor-sphincter dyssynergia is treated with a composition comprising a therapeutically effective amount of a TVEMP where such administration reduces urine flow interruption, reduces detrusor pressure, and/or reduces urinary retention.

Another type of urogenital-neurological disorder is a lower urinary tract dysfunction (LUTD). See e.g., Paul Abrams et al., *The Standardisation of Terminology of Lower Urinary Tract Function: Reposrt from the Standardisation Subcommittee of the International Continence Society,* 21 Neurourol Urodyn. 167-178 (2002), which is hereby incorporated by reference in its entirety. Lower urinary tract dysfunctions manifest three general types of symptoms: storage, voiding, and post-micturition symptoms. Storage symptoms are experienced during the storage phase of the bladder and include, without limitation, urinary urgency, urinary frequency, enuresis, polyuria, nocturia increased bladder sensation, decreased bladder sensation, absent bladder sensation, non-specific bladder sensation, and/or urinary incontinence. Voiding symptoms are experienced during the voiding phase. Symptoms include, without limitation, reduced urine flow, splitting or spraying of urine, intermittent urine flow, urinary hesitancy, strained effort to void urine, and/or terminal dribble of urine. Post-micturition symptoms are experienced immediately after micturition and include, without limitation, sensation of incomplete emptying and/or post-micturition dribble.

Thus, in an embodiment, a mammal suffering from a lower urinary tract dysfunction is treated with a composition comprising a therapeutically effective amount of a TVEMP where such administration reduces a symptom associated with the lower urinary tract dysfunction. In an aspect of this embodiment, a mammal suffering from a lower urinary tract dysfunction is treated with a composition comprising a therapeutically effective amount of a TVEMP where such administration reduces storage symptoms. In aspects of this embodiment, the storage symptom reduced is urinary urgency, urinary frequency, enuresis, polyuria, nocturia increased bladder sensation, decreased bladder sensation, absent bladder sensation, non-specific bladder sensation, or urinary incontinence. In another aspect of this embodiment, a mammal suffering from a lower urinary tract dysfunction is treated with a composition comprising a therapeutically effective amount of a TVEMP where such administration reduces voiding symptoms. In aspects of this embodiment, the voiding symptom reduced is reduced urine flow, splitting or spraying of urine, intermittent urine flow, urinary hesitancy, strained effort to void urine, or terminal dribble of urine. In yet another aspect of this embodiment, a mammal suffering from a lower urinary tract dysfunction is treated with a composition comprising a therapeutically effective amount of a TVEMP where such administration reduces post-micturition symptoms. In aspects of this embodiment, the post-micturition symptom reduced is sensation of incomplete emptying or post-micturition dribble.

Another type of urogenital-neurological disorder is urinary retention. Urinary retention is the inability to pass urine from the bladder and may be either an acute or chronic condition. Normally, the reflex to urinate is triggered when the bladder fills to approximately 300-500 mL. The bladder is then emptied when the contraction of the bladder wall forces urine out through the urethra. The bladder, internal sphincters, and external sphincters may all be affected by disorders that create abnormalities in bladder function resulting in urinary retention. Urinary retention can result either from loss of bladder muscle contracting performance or loss of appropriate coordination between the bladder muscle and the urethral sphincter muscle. The inability to properly relax the urinary sphincter muscles causing difficulty in emptying the bladder, which can lead to urinary retention. Often, a strong urge to void is experienced when only a small amount of urine is in the bladder. In addition, there may be reduced bladder capacity and incomplete emptying of urine. Urinary retention may also be caused by difficulty in relaxing the urinary sphincter muscle because the sphincter may be spastic. Alternatively, the bladder neck may be hypertrophied. Other causes of urinary retention include interruptions in the nerve pathways to the bladder occurring above the sacrum. This nerve damage results in a loss of sensation and motor control and is often seen in stroke, Parkinson's disease, spina bifida, diabetes, pelvic surgery, or invertebral disc herniation, and most forms of spinal cord injuries. Sometimes no cause is found, and such idiopathic cases may be due to anxiety or aging. Urinary retention can also occur by a blockage to the flow of urine due to prostate enlargement or urinary tract stones. Another type of urinary retention disorder is stones, which block the urinary tract of an individual thereby causing stoppage of urine flow and/or infection. Either chronic or acute retention may lead to incontinence due to leakage of urine from an overfull bladder.

Thus, in an embodiment, a mammal suffering from urinary retention is treated with a composition comprising a therapeutically effective amount of a TVEMP where such administration reduces a symptom associated with the urinary retention. In an aspect of this embodiment, a mammal suffering from urinary retention is treated with a composition comprising a therapeutically effective amount of a TVEMP where such administration reduces urinary urgency, reduces urinary frequency, increases bladder capacity, reduces urinary incontinence, and/or restores normal urine flow.

In another embodiment, a mammal suffering from acute urinary retention is treated with a composition comprising a therapeutically effective amount of a TVEMP where such administration reduces a symptom associated with the acute urinary retention. In yet another embodiment, a mammal suffering from chronic urinary retention is treated with a composition comprising a therapeutically effective amount of a TVEMP where such administration reduces a symptom associated with the chronic urinary retention.

Another type of urogenital-neurological disorder is urinary hesitancy. Urinary hesitancy is difficulty starting or maintaining a urinary stream. This problem affects people of all ages and occurs in both sexes, but it is most common in older men with enlarged prostate glands. Urinary hesitancy usually comes on gradually. It sometimes goes unnoticed until urinary retention (complete inability to urinate) produces distention and discomfort in the bladder. Almost all older men have some degree of difficulty in starting urination, dribbling, or decreased force of the urinary stream. Urinary hesitancy can be caused by benign prostatic hyperplasia (enlarged prostate), urinary tract infection, especially if chronic and recurrent, prostatitis (inflammation or infection of the prostate gland), drugs (some cold remedies, some nasal decongestants, tricyclic antidepressants, and anticholinergics which may be used for incontinence), shy or bashful bladder syndrome in younger people (unable to urinate when another person is in the room), and neurological disorders.

Thus, in an embodiment, a mammal suffering from urinary hesitancy is treated with a composition comprising a therapeutically effective amount of a TVEMP where such administration reduces a symptom associated with the urinary hesitancy. In an aspect of this embodiment, a mammal suffering from urinary hesitancy is treated with a composition comprising a therapeutically effective amount of a TVEMP where such administration reduces urinary urgency, reduces urinary frequency, increases bladder capacity, reduces urinary incontinence, and/or restores normal urine flow.

Another type of urogenital-neurological disorder is polyuria. Polyuria is when a person releases abnormally excessive volume of urine each day. An excessive volume of urination for an adult would be at least 2.5 liters of urine per day. Polyuria is a fairly common symptom, which is often noticed when you have to get up to use the bathroom at night. Thus, in an embodiment, a mammal suffering from polyuria is treated with a composition comprising a therapeutically effective amount of a TVEMP where such administration reduces a symptom associated with the polyuria.

Another type of urogenital-neurological disorder is nocturia. Nocturia is excessive urination at night, such as by waking up several times during the night to urinate. Normally, urine decreases in amount and become more concentrated at night, and as such, most people can sleep 6 to 8 hours without having to urinate. But, persons with nocturia get up more than once during the night to urinate. Because of this, those who have excessive urination at night often have disrupted sleep cycles. Causes include benign prostatic hyperplasia, certain drugs including diuretics, cardiac glycosides, demeclocycline, lithium, methoxyflurane, phenytoin, propoxyphene, and excessive vitamin D, chronic or recurrent urinary tract infection, chronic renal failure, congestive heart failure, cystitis, diabetes, drinking too much fluid before bedtime, particularly coffee, caffeinated beverages, or alcohol, and obstructive sleep apnea and other sleeping disorders. Thus, in an embodiment, a mammal suffering from nocturia is treated with a composition comprising a therapeutically effective amount of a TVEMP where such administration reduces a symptom associated with the nocturia.

Another type of urogenital-neurological disorder is chronic urinary tract infection (recurrent infection). Chronic urinary tract infection (UTI) is a bacterial infection of the bladder or lower urinary tract (urethra) that lasts for a long time. Most urinary tract infections occur in the lower urinary tract, which includes the bladder and urethra. The condition occurs when the normally clean lower urinary tract is infected by bacteria and becomes inflamed. Urinary tract infections are very common. Most of the time, symptoms of a urinary tract infection disappear within 24-48 hours after treatment begins. However, if the condition occurs more than twice in 6 months, lasts longer than 2 weeks, or does not respond to usual treatment, it is considered chronic. The elderly are at increased risk for such infections because the bladder doesn't empty fully due to such conditions as benign prostatic hyperplasia, prostatitis, and urethral strictures. Other irritating symptoms may include painful urination (dysuria), which may be a result of a urinary tract infection (UTI) caused by urine being held too long in the bladder. UTI with fever is a sign of potential severe kidney infection (pyelonephritis) and is a more worrisome situation as it may result in permanent damage of the kidney(s). Another type of urinary tract infection is vesicoureteral reflux (VUR). Vesicoureteral reflux is an abnormal backup of urine from the bladder to the kidney(s) that occurs as a way of releasing high pressure within the bladder. A UTI is of particular concern as VUR may place the patient at significant risk for a severe kidney infection by transporting infected bladder urine directly to the kidney(s).

Thus, in an embodiment, a mammal suffering from chronic urinary tract infection is treated with a composition comprising a therapeutically effective amount of a TVEMP where such administration reduces a symptom associated with the chronic urinary tract infection. In another embodiment, a mammal suffering from dysuria is treated with a composition comprising a therapeutically effective amount of a TVEMP where such administration reduces a symptom associated with the dysuria. In yet another embodiment, a mammal suffering from vesicoureteral reflux is treated with a composition comprising a therapeutically effective amount of a TVEMP where such administration reduces a symptom associated with the vesicoureteral reflux.

Other types of urogenital-neurological disorders are disorders associated with prostate disorders. The prostate is a partially glandular and partially fibromuscular organ of the male reproductive system that that produces the fluid that carries sperm during ejaculation. It surrounds the urethra, the tube through which urine passes out of the body. One type of prostate disorder is benign prostatic hyperplasia (BPH). During aging, the prostate tends to enlarge (hypertrophy) and this enlarged prostate is often called benign prostatic hyperplasia (BPH) or benign prostatic hypertrophy. Prostatic enlargement can lead to urethral obstruction and voiding dysfunction because the enlarged gland can press on the urethra. BPH is not cancer, and it does not raise your risk for prostate cancer. One type of prostate disorder is prostatitis. Prostatitis is an inflammation of the prostate gland. Prostatitis includes acute and chronic bacterial prostatitis and inflammation not caused by bacterial infection (abacterial prostatitis). One type of prostate disorder is prostatodynia. Prostatodynia is a type of inflammation of the prostate not due to bacterial infection that may be caused by abnormal nerves or muscles in the region. Prostatodynia is typically a chronic, painful disease. The symptoms (including chills, fever, pain in the lower back and genital area, body aches, burning or painful urination, and the frequent and urgent need to urinate) characteristically go away and then come back without warning.

Thus, in an embodiment, a mammal suffering from a urogenital-neurological disorder associated with a prostate disorder is treated with a composition comprising a therapeutically effective amount of a TVEMP where such administration reduces a symptom associated with the urogenital-neurological disorder associated with the prostate disorder. In another aspect of this embodiment, a mammal suffering from urogenital-neurological disorder associated with benign prostatic hyperplasia is treated with a composition comprising a therapeutically effective amount of a TVEMP where such administration reduces a symptom associated with the urogenital-neurological disorder associated with benign prostatic hyperplasia. In yet another aspect of this embodiment, a mammal suffering from urogenital-neurological disorder associated with prostatitis is treated with a composition comprising a therapeutically effective amount of a TVEMP where such administration reduces a symptom associated with the urogenital-neurological disorder associated with prostatitis. In still another aspect of this embodiment, a mammal suffering from urogenital-neurological disorder associated with prostatodynia is treated with a composition comprising a therapeutically effective amount of a TVEMP where such administration reduces a symptom associated with the urogenital-neurological disorder associated with prostatodynia.

In another embodiment, a mammal suffering from a prostate disorder is treated with a composition comprising a therapeutically effective amount of a TVEMP where such administration reduces a symptom associated with the prostate disorder. In an aspect of this embodiment, a mammal suffering from benign prostatic hyperplasia is treated with a composition comprising a therapeutically effective amount of a TVEMP where such administration reduces a symptom associated with the benign prostatic hyperplasia. In yet another aspect of this embodiment, a mammal suffering from prostatitis is treated with a composition comprising a therapeutically effective amount of a TVEMP where such administration reduces a symptom associated with the prostatitis. In still another aspect of this embodiment, a mammal suffering from prostatodynia is treated with a composition comprising a therapeutically effective amount of a TVEMP where such administration reduces a symptom associated with the prostatodynia.

Other types of urogenital-neurological disorders are disorders associated with uterine disorders. The uterus is a hollow, muscular pear-shaped female reproductive organ in which the fertilized zygote implants and develops into the fetus. The uterus comprises a corpus made up of two layers of tissue, fundus, isthmus, and cervix located between the urinary bladder and the rectum in the pelvic cavity of female mammals. One type of uterine disorder is endometriosis. Endometriosis is a condition in which the tissue that lines the inside of the uterus (called the endometrium or endometrial lining) is found growing in other areas outside of the uterus (commonly the ovaries, fallopian tubes, outer surface of the uterus, outer surface of the intestines, and nearby structures of the pelvis). This condition often causes severe pain within the lower abdomen and pelvis that may be associated with your periods each month. The symptoms of endometriosis include pain before and during menstrual periods, pain at the time of ovulation, pain during or after sexual activity, heavy or irregular bleeding, fatigue, pain with bowel movements at the time of the period, pain with urination. Another type of uterine disorder is dysmenorrhea. Dysmenorrhea is the pain or discomfort (menstrual cramps) during or just before a menstrual period. There are two types of dysmenorrheal, primary dysmenorrhea and secondary dysmenorrhea. Primary dysmenorrhea is severe, disabling cramps without underlying illness. Symptoms may include backache, leg pain, nausea, vomiting, diarrhea, headache, and dizziness. This kind of dysmenorrhea usually affects young woman within two years of the onset of menstruation and lasts one or two days each month. Secondary dysmenorrhea is cramps caused by another medical problem(s) such as endometriosis (abnormalities in the lining of the uterus), adenomyosis (nonmalignant growth of the endometrium into the muscular layer of the uterus), pelvic inflammatory disease, uterine fibroids, cervical narrowing, uterine malposition, pelvic tumors or an IUD (intra-uterine device). This condition usually occurs in older women.

Thus, in an embodiment, a mammal suffering from a urogenital-neurological disorder associated with a uterine disorder is treated with a composition comprising a therapeutically effective amount of a TVEMP where such administration reduces a symptom associated with the urogenital-neurological disorder associated with the uterine disorder. In an aspect of this embodiment, a mammal suffering from endometriosis is treated with a composition comprising a therapeutically effective amount of a TVEMP where such administration reduces a symptom associated with the endometriosis. In an aspect of this embodiment, a mammal suffering from dysmenorrhea is treated with a composition comprising a therapeutically effective amount of a TVEMP where such administration reduces a symptom associated with the dysmenorrhea.

Other types of urogenital-neurological disorders are urogenital-neurological disorders associated with neurogenic dysfunction. Thus, in an embodiment, a mammal suffering from a urogenital-neurological disorder associated with a neurogenic dysfunction is treated with a composition comprising a therapeutically effective amount of a TVEMP where such administration reduces a symptom associated with the urogenital-neurological disorder associated with the neurogenic dysfunction. In an aspect of this embodiment, a mammal suffering from a urogenital-neurological disorder associated with Parkinson's Disease is treated with a composition comprising a therapeutically effective amount of a TVEMP where such administration reduces a symptom associated with the urogenital-neurological disorder associated with Parkinson's Disease. In another aspect of this embodiment, a mammal suffering from a urogenital-neurological disorder associated with multiple sclerosis is treated with a composition comprising a therapeutically effective amount of a TVEMP where such administration reduces a symptom associated with the urogenital-neurological disorder associated with multiple sclerosis. In yet another aspect of this embodiment, a mammal suffering from a urogenital-neurological disorder associated with spina bifida is treated with a composition comprising a therapeutically effective amount of a TVEMP where such administration reduces a symptom associated with the urogenital-neurological disorder associated with spina bifida. In yet another aspect of this embodiment, a mammal suffering from a urogenital-neurological disorder associated with transverse myelitis is treated with a composition comprising a therapeutically effective amount of a TVEMP where such administration reduces a symptom associated with the urogenital-neurological disorder associated with transverse myelitis. In yet another aspect of this embodiment, a mammal suffering from a urogenital-neurological disorder associated with stroke is treated with a composition comprising a therapeutically effective amount of a TVEMP where such administration reduces a symptom associated with the urogenital-neurological disorder associated with stroke. In still another aspect of this embodiment, a mammal suffering from a urogenital-neurological disorder associated with a spinal cord injury is treated with a composition comprising a therapeutically effective amount of a TVEMP where such administration reduces a symptom associated with the urogenital-neurological disorder associated with the spinal cord injury. In still another aspect of this embodiment, a mammal suffering from a urogenital-neurological disorder associated with a spasm reflex is treated with a composition comprising a therapeutically effective amount of a TVEMP where such administration reduces a symptom associated with the urogenital-neurological disorder associated with the spasm reflex. In a further aspect of this embodiment, a mammal suffering from a urogenital-neurological disorder associated with a neurologic lesion of the spinal cord or brain is treated with a composition comprising a therapeutically effective amount of a TVEMP where such administration reduces a symptom associated with the urogenital-neurological disorder associated with the neurologic lesion of the spinal cord or brain.

Aspects of the present invention provide, in part, a mammal. A mammal includes a human, and a human can be a patient. Other aspects of the present invention provide, in part, an individual. An individual includes a human, and a human can be a patient.

Aspects of the present invention provide, in part, administering a composition comprising a TVEMP. As used herein, the term "administering" refers to any delivery mechanism that provides a composition comprising a TVEMP to a patient that potentially results in a clinically, therapeutically, or experimentally beneficial result. A TVEMP can be delivered to a patient using a cellular uptake approach where a TVEMP is delivered intracellular or a gene therapy approach where a TVEMP is express derived from precursor RNAs expressed from an expression vectors.

A composition comprising a TVEMP as disclosed in the present specification can be administered to a mammal using a cellular uptake approach. Administration of a composition comprising a TVEMP using a cellular uptake approach comprise a variety of enteral or parenteral approaches including, without limitation, oral administration in any acceptable form, such as, e.g., tablet, liquid, capsule, powder, or the like; topical administration in any acceptable form, such as, e.g., drops, spray, creams, gels or ointments; intravascular administration in any acceptable form, such as, e.g., intravenous bolus injection, intravenous infusion, intra-arterial bolus injection, intra-arterial infusion and catheter instillation into the vasculature; peri- and intra-tissue administration in any acceptable form, such as, e.g., intraperitoneal injection, intramuscular injection, subcutaneous injection, subcutaneous infusion, intraocular injection, retinal injection, or sub-retinal injection or epidural injection; intravesicular administration in any acceptable form, such as, e.g., catheter instillation; and by placement device, such as, e.g., an implant, a patch, a pellet, a catheter, an osmotic pump, a suppository, a bioerodible delivery system, a non-bioerodible delivery system or another implanted extended or slow release system. An exemplary list of biodegradable polymers and methods of use are described in, e.g., Handbook of Biodegradable Polymers (Abraham J. Domb et al., eds., Overseas Publishers Association, 1997).

A composition comprising a TVEMP can be administered to a mammal by a variety of methods known to those of skill in the art, including, but not restricted to, encapsulation in liposomes, by ionophoresis, or by incorporation into other vehicles, such as hydrogels, cyclodextrins, biodegradable nanocapsules, and bioadhesive microspheres, or by proteinaceous vectors. Delivery mechanisms for administering a composition comprising a TVEMP to a patient are described in, e.g., Leonid Beigelman et al., Compositions for the Delivery of Negatively Charged Molecules, U.S. Pat. No. 6,395,713 (May 28, 2002); and Achim Aigner, Delivery Systems for the Direct Application of siRNAs to Induce RNA Interference (RNAi) in vivo, 2006(716559) J. Biomed. Biotech. 1-15 (2006); Controlled Drug Delivery: Designing Technologies for the Future (Kinam Park & Randy J. Mrsny eds., American Chemical Association, 2000); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/ 0137059 (Jul. 15, 2004); Patrick M. Hughes et al., Anti-Angiogenic Sustained Release Intraocular Implants and Related Methods, U.S. patent application Ser. No. 11/364,687 (Feb. 27, 2006); and Patrick M. Hughes et al., Sustained Release Intraocular Drug Delivery Systems, U.S. Patent Publication 2006/0182783 (Aug. 17, 2006), each of which is hereby incorporated by reference in its entirety.

A composition comprising a TVEMP as disclosed in the present specification can also be administered to a patient using a gene therapy approach by expressing a TVEMP within in a cell manifesting a nerve-based etiology that contributes to a urogenital-neurological disorder. A TVEMP can be expressed from nucleic acid molecules operably-linked to an expression vector, see, e.g., P. D. Good et al., Expression of Small, Therapeutic RNAs in Human Cell Nuclei, 4(1) Gene Ther. 45-54 (1997); James D. Thompson, Polymerase III-based expression of therapeutic RNAs, U.S. Pat. No. 6,852,535 (Feb. 8, 2005); Maciej Wiznerowicz et al., Tuning Silence: Conditional Systems for RNA Interference, 3(9) Nat. Methods 682-688m (2006); Ola Snøve and John J. Rossi, Expressing Short Hairpin RNAi in vivo, 3(9) Nat. Methods 689-698 (2006); and Charles X. Li et al., Delivery of RNA Interference, 5(18) Cell Cycle 2103-2109 (2006). A person of ordinary skill in the art would realize that any TVEMP can be expressed in eukaryotic cells using an appropriate expression vector.

Expression vectors capable of expressing a TVEMP can provide persistent or stable expression of the TVEMP in a cell manifesting a nerve-based etiology that contributes to a urogenital-neurological disorder. Alternatively, expression vectors capable of expressing a TVEMP can provide for transient expression of the TVEMP in a cell manifesting a nerve-based etiology that contributes to a urogenital-neurological disorder. Such transiently expressing vectors can be repeatedly administered as necessary. A TVEMP-expressing vectors can be administered by a delivery mechanism and route of administration discussed above, by administration to target cells ex-planted from a patient followed by reintroduction into the patient, or by any other method that would allow for introduction into the desired target cell, see, e.g., Larry A. Couture and Dan T. Stinchcomb, Anti-gene Therapy: The Use of Ribozymes to Inhibit Gene Function, 12(12) Trends Genet. 510-515 (1996).

The actual delivery mechanism used to administer a composition comprising a TVEMP to a mammal can be determined by a person of ordinary skill in the art by taking into account factors, including, without limitation, the type of urogenital-neurological disorder, the location of the urogenital-neurological disorder, the cause of the urogenital-neurological disorder, the severity of the urogenital-neurological disorder, the degree of relief desired, the duration of relief desired, the particular TVEMP used, the rate of excretion of the TVEMP used, the pharmacodynamics of the TVEMP used, the nature of the other compounds to be included in the composition, the particular route of administration, the particular characteristics, history and risk factors of the patient, such as, e.g., age, weight, general health and the like, or any combination thereof.

In an embodiment, a composition comprising a TVEMP is administered to the site to be treated by injection. In aspects of this embodiment, injection of a composition comprising a TVEMP is by, e.g., intramuscular injection, subdermal injection, or dermal injection. In aspects of this embodiment, injection of a composition comprising a TVEMP is into the lower urinary tract, including the bladder wall, the urinary sphincter or bladder neck.

A composition comprising a TVEMP can be administered to a mammal using a variety of routes. Routes of administration suitable for a method of treating an urogenital-neurological disorder as disclosed in the present specification include both local and systemic administration. Local administration results in significantly more delivery of a composition to a specific location as compared to the entire body of the mammal, whereas, systemic administration results in delivery of a composition to essentially the entire body of the patient. Routes of administration suitable for a method of treating an urogenital-neurological disorder as disclosed in the present specification also include both central and peripheral administration. Central administration results in delivery of a composition to essentially the central nervous system of the patient and includes, e.g., intrathecal administration, epidural administration as well as a cranial injection or implant. Peripheral administration results in delivery of a composition to essentially any area of a patient outside of the central nervous system and encompasses any route of administration other than direct administration to the spine or brain. The actual route of administration of a composition comprising a TVEMP used in a mammal can be determined by a person of ordinary skill in the art by taking into account factors, including, without limitation, the type of urogenital-neurological disorder, the location of the urogenital-neurological disorder, the cause of the urogenital-neurological disorder, the severity of the urogenital-neurological disorder, the degree of relief desired, the duration of relief desired, the particular TVEMP used, the rate of excretion of the TVEMP used, the pharmacodynamics of the TVEMP used, the nature of the other compounds to be included in the composition, the particular route of administration, the particular characteristics, history and risk factors of the mammal, such as, e.g., age, weight, general health and the like, or any combination thereof.

In an embodiment, a composition comprising a TVEMP is administered systemically to a mammal. In another embodiment, a composition comprising a TVEMP is administered locally to a mammal. In an aspect of this embodiment, a composition comprising a TVEMP is administered to the bladder of a mammal. In another aspect of this embodiment, a composition comprising a TVEMP is administered to the prostate of a mammal. In another aspect of this embodiment, a composition comprising a TVEMP is administered to the uterus of a mammal.

Aspects of the present invention provide, in part, administering a therapeutically effective amount of a composition comprising a TVEMP. As used herein, the term "therapeutically effective amount" is synonymous with "therapeutically effective dose" and when used in reference to treating an urogenital-neurological disorder refers to the minimum dose of a TVEMP necessary to achieve the desired therapeutic effect and includes a dose sufficient to reduce a symptom associated with an urogenital-neurological disorder. In aspects of this embodiment, a therapeutically effective amount of a composition comprising a TVEMP reduces a symptom associated with an urogenital-neurological disorder by, e.g., at least 30%, at least 40%, at least 50%, at least 60%, at least 70%, at least 80%, at least 90% or at least 100%. In other aspects of this embodiment, a therapeutically effective amount of a composition comprising a TVEMP reduces a symptom associated with an urogenital-neurological disorder by, e.g., at most 30%, at most 40%, at most 50%, at most 60%, at most 70%, at most 80%, at most 90% or at most 100%. In yet other aspects of this embodiment, a therapeutically effective amount of a composition comprising a TVEMP reduces a symptom associated with an urogenital-neurological disorder by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In other aspects of this embodiment, a therapeutically effective amount of a composition comprising a TVEMP reduces a symptom associated with an urogenital-neurological disorder by, e.g., about one week, about one month, about two months, about three months, about four months, about five months, about six months, about seven months, about eight months, about nine months, about ten months, about eleven months, or about twelve months. In yet other aspects of this embodiment, a therapeutically effective amount of a composition comprising a TVEMP reduces a symptom associated with an urogenital-neurological disorder by, e.g., at least one week, at least one month, at least two months, at least three months, at least four months, at least five months, at least six months, at least seven months, at least eight months, at least nine months, at least ten months, at least eleven months, or at least twelve months. In still other aspects of this embodiment, a therapeutically effective amount of a composition comprising a TVEMP reduces a symptom associated with an urogenital-neurological disorder by, e.g., about 1 week to about three months, about one month to about six months, about one month to about nine months, about one month to about twelve months, about three months to about six months, about three months to about nine months, about three months to about twelve months.

The actual therapeutically effective amount of a composition comprising a TVEMP to be administered to a mammal can be determined by a person of ordinary skill in the art by taking into account factors, including, without limitation, the type of urogenital-neurological disorder, the location of the urogenital-neurological disorder, the cause of the urogenital-neurological disorder, the severity of the urogenital-neurological disorder, the degree of relief desired, the duration of relief desired, the particular TVEMP used, the rate of excretion of the TVEMP used, the pharmacodynamics of the TVEMP used, the nature of the other compounds to be included in the composition, the particular route of administration, the particular characteristics, history and risk factors of the patient, such as, e.g., age, weight, general health and the like, or any combination thereof. Additionally, where repeated administration of a composition comprising a TVEMP is used, the actual effect amount of a composition comprising a TVEMP will further depend upon factors, including, without limitation, the frequency of administration, the half-life of the composition comprising a TVEMP, or any combination thereof. In is known by a person of ordinary skill in the art that an effective amount of a composition comprising a TVEMP can be extrapolated from in vitro assays and in vivo administration studies using animal models prior to administration to humans. Wide variations in the necessary effective amount are to be expected in view of the differing efficiencies of the various routes of administration. For instance, oral administration generally would be expected to require higher dosage levels than administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending physician in consideration of the above-identified factors.

As a non-limiting example, when administering a composition comprising a TVEMP to a mammal, a therapeutically effective amount generally is in the range of about 1 fg to about 3.0 mg. In aspects of this embodiment, an effective amount of a composition comprising a TVEMP can be, e.g., about 100 fg to about 3.0 mg, about 100 µg to about 3.0 mg, about 100 ng to about 3.0 mg, or about 100 µg to about 3.0 mg. In other aspects of this embodiment, an effective amount of a composition comprising a TVEMP can be, e.g., about 100 fg to about 750 µg, about 100 µg to about 750 µg, about 100 ng to about 750 µg, or about 1 µg to about 750 µg. In yet other aspects of this embodiment, a therapeutically effective amount of a composition comprising a TVEMP can be, e.g., at least 1 fg, at least 250 fg, at least 500 fg, at least 750 fg, at least 1 µg, at least 250 µg, at least 500 µg, at least 750 µg, at least 1 ng, at least 250 ng, at least 500 ng, at least 750 ng, at least 1 µg, at least 250 µg, at least 500 µg, at least 750 µg, or at least 1 mg. In still other aspects of this embodiment, a therapeutically effective amount of a composition comprising a TVEMP can be, e.g., at most 1 fg, at most 250 fg, at most 500 fg, at most 750 fg, at most 1 µg, at most 250 µg, at most 500 µg, at most 750 µg, at most 1 ng, at most 250 ng, at most 500 ng, at most 750 ng, at most 1 µg, at least 250 µg, at most 500 µg, at most 750 µg, or at most 1 mg.

As another non-limiting example, when administering a composition comprising a TVEMP to a mammal, a therapeutically effective amount generally is in the range of about 0.00001 mg/kg to about 3.0 mg/kg. In aspects of this embodiment, an effective amount of a composition comprising a TVEMP can be, e.g., about 0.0001 mg/kg to about 0.001 mg/kg, about 0.03 mg/kg to about 3.0 mg/kg, about 0.1 mg/kg to about 3.0 mg/kg, or about 0.3 mg/kg to about 3.0 mg/kg. In yet other aspects of this embodiment, a therapeutically effective amount of a composition comprising a TVEMP can be, e.g., at least 0.00001 mg/kg, at least 0.0001 mg/kg, at least 0.001 mg/kg, at least 0.01 mg/kg, at least 0.1 mg/kg, or at least 1 mg/kg. In yet other aspects of this embodiment, a therapeutically effective amount of a composition comprising a TVEMP can be, e.g., at most 0.00001 mg/kg, at most 0.0001 mg/kg, at most 0.001 mg/kg, at most 0.01 mg/kg, at most 0.1 mg/kg, or at most 1 mg/kg.

Dosing can be single dosage or cumulative (serial dosing), and can be readily determined by one skilled in the art. For instance, treatment of an urogenital-neurological disorder may comprise a one-time administration of an effective dose of a composition comprising a TVEMP. As a non-limiting example, an effective dose of a composition comprising a TVEMP can be administered once to a patient, e.g., as a single injection or deposition at or near the site exhibiting a symptom of an urogenital-neurological disorder. Alternatively, treatment of an urogenital-neurological disorder may comprise multiple administrations of an effective dose of a composition comprising a TVEMP carried out over a range of time periods, such as, e.g., daily, once every few days, weekly, monthly or yearly. As a non-limiting example, a composition comprising a TVEMP can be administered once or twice yearly to a mammal. The timing of administration can vary from mammal to mammal, depending upon such factors as the severity of a mammal's symptoms. For example, an effective dose of a composition comprising a TVEMP can be administered to a mammal once a month for an indefinite period of time, or until the patient no longer requires therapy. A person of ordinary skill in the art will recognize that the condition of the mammal can be monitored throughout the course of treatment and that the effective amount of a composition comprising a TVEMP that is administered can be adjusted accordingly.

A composition comprising a TVEMP as disclosed in the present specification can also be administered to a mammal in combination with other therapeutic compounds to increase the overall therapeutic effect of the treatment. The use of multiple compounds to treat an indication can increase the beneficial effects while reducing the presence of side effects.

Aspects of the present invention can also be described as follows:

1. A method of treating urogenital-neurological disorder in a mammal, the method comprising the step of administering to the mammal in need thereof a therapeutically effective amount of a composition including a TVEMP comprising a retargeted peptide binding domain, a Clostridial toxin translocation domain and a Clostridial toxin enzymatic domain, wherein administration of the composition reduces a symptom of the urogenital-neurological disorder, thereby treating the mammal.

2. The method of 1, wherein the TVEMP comprises a linear amino-to-carboxyl single polypeptide order of 1) the Clostridial toxin enzymatic domain, the Clostridial toxin translocation domain, the retargeted peptide binding domain, 2) the Clostridial toxin enzymatic domain, the retargeted peptide binding domain, the Clostridial toxin translocation domain, 3) the retargeted peptide binding domain, the Clostridial toxin translocation domain, and the Clostridial toxin enzymatic domain, 4) the retargeted peptide binding domain, the Clostridial toxin enzymatic domain, the Clostridial toxin translocation domain, 5) the Clostridial toxin translocation domain, the Clostridial toxin enzymatic domain and the retargeted peptide binding domain, or 6) the Clostridial toxin translocation domain, the retargeted peptide binding domain and the Clostridial toxin enzymatic domain.

3. The method of 1, wherein the retargeted peptide binding domain is a galanin peptide binding domain, a PAR peptide binding domain, a somatostatin peptide binding domain, a neurotensin peptide binding domain, a SLURP peptide binding domain.

4. The method of 3, wherein the galanin peptide binding domain is a galanin or a galanin message-associated peptide (GMAP).

5. The method of 3, wherein the galanin peptide binding domain comprises SEQ ID NO: 67 or SEQ ID NO: 68.

6. The method of 3, wherein the PAR peptide binding domain is a PAR1 peptide, a PAR2 peptide, a PAR3 peptide and a PAR4 peptide.

7. The method of 3, wherein the PAR peptide binding domain comprises amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

8. The method of 3, wherein the somatostatin peptide binding domain is a somatostatin peptide.

9. The method of 3, wherein the somatostatin peptide binding domain comprises amino acids 99-116 of SEQ ID NO: 73.

10. The method of 3, wherein the neurotensin peptide binding domain a neurotensin or a neuromedin N.

11. The method of 3, wherein the neurotensin peptide binding domain comprises amino acids 143-148 or amino acids 151-163 of SEQ ID NO: 74.

12. The method of 3, wherein the SLURP peptide binding domain is a SLURP-1 or a SLURP-2.

13. The method of 3, wherein the SLURP peptide binding domain comprises amino acids 23-101 of SEQ ID NO: 75 or amino acids 23-95 of SEQ ID NO: 76.

14. The method of 1, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

15. The method of 1, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

16. The method of 1, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

17. The method of 16, wherein the urinary incontinence is an urge urinary incontinence, a stress urinary incontinence, an overflow urinary incontinence, a mixed urinary incontinence, or a continuous urinary incontinence.

18. The method of 16, wherein the detrusor dysfunction is a detrusor overactivity, a detrusor instability, or a detrusor-sphincter dyssynergia.

19. The method of 16, wherein the urogenital disorder associated with a prostate disorder is an urogenital disorder associated with benign prostatic hyperplasia, an urogenital disorder associated with prostatitis, or an urogenital disorder associated with prostatodynia.

20. The method of 16, wherein the urogenital disorder associated with a neurogenic dysfunction is an urogenital disorder associated with Parkinson's Disease, an urogenital disorder associated with multiple sclerosis, an urogenital disorder associated with spina bifida, an urogenital disorder associated with transverse myelitis, an urogenital disorder associated with stroke, an urogenital disorder associated with a spinal cord injury, an urogenital disorder associated with a spasm reflex, an urogenital disorder associated with a neurologic lesion of the spinal cord, or an urogenital disorder associated with a neurologic lesion of the brain.

21. A method of treating urogenital-neurological disorder in a mammal, the method comprising the step of administering to the mammal in need thereof a therapeutically effective amount of a composition including a TVEMP comprising a retargeted peptide binding domain, a Clostridial toxin translocation domain, a Clostridial toxin enzymatic domain, and an exogenous protease cleavage site, wherein administration of the composition reduces a symptom of the urogenital-neurological disorder, thereby treating the mammal.

22. The method of 21, wherein the TVEMP comprises a linear amino-to-carboxyl single polypeptide order of 1) the Clostridial toxin enzymatic domain, the exogenous protease cleavage site, the Clostridial toxin translocation domain, the retargeted peptide binding domain, 2) the Clostridial toxin enzymatic domain, the exogenous protease cleavage site, the retargeted peptide binding domain, the Clostridial toxin translocation domain, 3) the retargeted peptide binding domain, the Clostridial toxin translocation domain, the exogenous protease cleavage site and the Clostridial toxin enzymatic domain, 4) the retargeted peptide binding domain, the Clostridial toxin enzymatic domain, the exogenous protease cleavage site, the Clostridial toxin translocation domain, 5) the Clostridial toxin translocation domain, the exogenous protease cleavage site, the Clostridial toxin enzymatic domain and the retargeted peptide binding domain, or 6) the Clostridial toxin translocation domain, the exogenous protease cleavage site, the retargeted peptide binding domain and the Clostridial toxin enzymatic domain.

23. The method of 21, wherein the retargeted peptide binding domain is a galanin peptide binding domain, a PAR peptide binding domain, a somatostatin peptide binding domain, a neurotensin peptide binding domain, a SLURP peptide binding domain.

24. The method of 23, wherein the galanin peptide binding domain is a galanin or a galanin message-associated peptide (GMAP).

25. The method of 23, wherein the galanin peptide binding domain comprises SEQ ID NO: 67 or SEQ ID NO: 68.

26. The method of 23, wherein the PAR peptide binding domain is a PAR1 peptide, a PAR2 peptide, a PAR3 peptide and a PAR4 peptide.

27. The method of 23, wherein the PAR peptide binding domain comprises amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

28. The method of 23, wherein the somatostatin peptide binding domain is a somatostatin peptide.

29. The method of 23, wherein the somatostatin peptide binding domain comprises amino acids 99-116 of SEQ ID NO: 73.

30. The method of 23, wherein the neurotensin peptide binding domain a neurotensin or a neuromedin N.

31. The method of 23, wherein the neurotensin peptide binding domain comprises amino acids 143-148 or amino acids 151-163 of SEQ ID NO: 74.

32. The method of 23, wherein the SLURP peptide binding domain is a SLURP-1 or a SLURP-2.

33. The method of 23, wherein the SLURP peptide binding domain comprises amino acids 23-101 of SEQ ID NO: 75 or amino acids 23-95 of SEQ ID NO: 76.

34. The method of 21, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

35. The method of 21, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

36. The method of 21, wherein the exogenous protease cleavage site is a plant papain cleavage site, an insect papain cleavage site, a crustacian papain cleavage site, an enterokinase cleavage site, a human rhinovirus 3C protease cleavage site, a human enterovirus 3C protease cleavage site, a tobacco etch virus protease cleavage site, a Tobacco Vein Mottling Virus cleavage site, a subtilisin cleavage site, a hydroxylamine cleavage site, or a Caspase 3 cleavage site.

37. The method of 21, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

38. The method of 37, wherein the urinary incontinence is an urge urinary incontinence, a stress urinary incontinence, an overflow urinary incontinence, a mixed urinary incontinence, or a continuous urinary incontinence.

39. The method of 37, wherein the detrusor dysfunction is a detrusor overactivity, a detrusor instability, or a detrusor-sphincter dyssynergia.

40. The method of 37, wherein the urogenital disorder associated with a prostate disorder is an urogenital disorder associated with benign prostatic hyperplasia, an urogenital disorder associated with prostatitis, or an urogenital disorder associated with prostatodynia.

41. The method of 37, wherein the urogenital disorder associated with a neurogenic dysfunction is an urogenital disorder associated with Parkinson's Disease, an urogenital disorder associated with multiple sclerosis, an urogenital disorder associated with spina bifida, an urogenital disorder associated with transverse myelitis, an urogenital disorder associated with stroke, an urogenital disorder associated with a spinal cord injury, an urogenital disorder associated with a spasm reflex, an urogenital disorder associated with a neurologic lesion of the spinal cord, or an urogenital disorder associated with a neurologic lesion of the brain.

42. A manufacturing of a medicament for treating urogenital-neurological disorder in a mammal in need thereof, wherein the medicament comprises a TVEMP including a retargeted peptide binding domain, a Clostridial toxin translocation domain and a Clostridial toxin enzymatic domain and wherein administration of a therapeutically effective amount of the medicament to the mammal reduces a symptom of the urogenital-neurological disorder, thereby treating the mammal.

43. A use of a composition for treating urogenital-neurological disorder in a mammal in need thereof, the use comprising the step of administering to the mammal in need thereof a therapeutically effective amount of a composition, wherein the composition comprises a TVEMP including a retargeted peptide binding domain, a Clostridial toxin translocation domain and a Clostridial toxin enzymatic domain and wherein administration of the composition reduces a symptom of the urogenital-neurological disorder, thereby treating the mammal.

44. The medicament of 42 or use of 43, wherein the TVEMP comprises a linear amino-to-carboxyl single polypeptide order of 1) the Clostridial toxin enzymatic domain, the Clostridial toxin translocation domain, the retargeted peptide binding domain, 2) the Clostridial toxin enzymatic domain, the retargeted peptide binding domain, the Clostridial toxin translocation domain, 3) the retargeted peptide binding domain, the Clostridial toxin translocation domain, and the Clostridial toxin enzymatic domain, 4) the retargeted peptide binding domain, the Clostridial toxin enzymatic domain, the Clostridial toxin translocation domain, 5) the Clostridial toxin translocation domain, the Clostridial toxin enzymatic domain and the retargeted peptide binding domain, or 6) the Clostridial toxin translocation domain, the retargeted peptide binding domain and the Clostridial toxin enzymatic domain.

45. The medicament of 42 or use of 43, wherein the retargeted peptide binding domain is a galanin peptide binding domain, a PAR peptide binding domain, a somatostatin peptide binding domain, a neurotensin peptide binding domain, a SLURP peptide binding domain.

46. The medicament or use of 45, wherein the galanin peptide binding domain is a galanin or a galanin message-associated peptide (GMAP).

47. The medicament or use of 45, wherein the galanin peptide binding domain comprises SEQ ID NO: 67 or SEQ ID NO: 68.

48. The medicament or use of 45, wherein the PAR peptide binding domain is a PAR1 peptide, a PAR2 peptide, a PAR3 peptide and a PAR4 peptide.

49. The medicament or use of 45, wherein the PAR peptide binding domain comprises amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

50. The medicament or use of 45, wherein the somatostatin peptide binding domain is a somatostatin peptide.

51. The medicament or use of 45, wherein the somatostatin peptide binding domain comprises amino acids 99-116 of SEQ ID NO: 73.

52. The medicament or use of 45, wherein the neurotensin peptide binding domain a neurotensin or a neuromedin N.

53. The medicament or use of 45, wherein the neurotensin peptide binding domain comprises amino acids 143-148 or amino acids 151-163 of SEQ ID NO: 74.

54. The medicament or use of 45, wherein the SLURP peptide binding domain is a SLURP-1 or a SLURP-2.

55. The medicament or use of 45, wherein the SLURP peptide binding domain comprises amino acids 23-101 of SEQ ID NO: 75 or amino acids 23-95 of SEQ ID NO: 76.

56. The medicament of 42 or use of 43, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

57. The medicament of 42 or use of 43, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

58. The medicament of 42 or use of 43, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

59. The medicament or use of 58, wherein the urinary incontinence is an urge urinary incontinence, a stress urinary incontinence, an overflow urinary incontinence, a mixed urinary incontinence, or a continuous urinary incontinence.

60. The medicament or use of 58, wherein the detrusor dysfunction is a detrusor overactivity, a detrusor instability, or a detrusor-sphincter dyssynergia.

61. The medicament or use of 58, wherein the urogenital disorder associated with a prostate disorder is an urogenital disorder associated with benign prostatic hyperplasia, an urogenital disorder associated with prostatitis, or an urogenital disorder associated with prostatodynia.

62. The medicament or use of 58, wherein the urogenital disorder associated with a neurogenic dysfunction is an urogenital disorder associated with Parkinson's Disease, an urogenital disorder associated with multiple sclerosis, an urogenital disorder associated with spina bifida, an urogenital disorder associated with transverse myelitis, an urogenital disorder associated with stroke, an urogenital disorder associated with a spinal cord injury, an urogenital disorder associated with a spasm reflex, an urogenital disorder associated with a neurologic lesion of the spinal cord, or an urogenital disorder associated with a neurologic lesion of the brain.

63. A manufacturing of a medicament for treating urogenital-neurological disorder in a mammal in need thereof, wherein the medicament comprises a TVEMP including a retargeted peptide binding domain, a Clostridial toxin translocation domain, a Clostridial toxin enzymatic domain, and an exogenous protease cleavage site and wherein administration of a therapeutically effective amount of the medicament to the mammal reduces a symptom of the urogenital-neurological disorder, thereby treating the mammal.

64. A use of a composition for treating urogenital-neurological disorder in a mammal in need thereof, the use comprising the step of administering to the mammal in need thereof a therapeutically effective amount of a composition, wherein the composition comprises a TVEMP including a retargeted peptide binding domain, a Clostridial toxin translocation domain, a Clostridial toxin enzymatic domain, and an exogenous protease cleavage site, and wherein administration of the composition reduces a symptom of the urogenital-neurological disorder, thereby treating the mammal.

65. The medicament of 63 or use of 64, wherein the TVEMP comprises a linear amino-to-carboxyl single polypeptide order of 1) the Clostridial toxin enzymatic domain, the exogenous protease cleavage site, the Clostridial toxin translocation domain, the retargeted peptide binding domain, 2) the Clostridial toxin enzymatic domain, the exogenous protease cleavage site, the retargeted peptide binding domain, the Clostridial toxin translocation domain, 3) the retargeted peptide binding domain, the Clostridial toxin translocation domain, the exogenous protease cleavage site and the Clostridial toxin enzymatic domain, 4) the retargeted peptide binding domain, the Clostridial toxin enzymatic domain, the exogenous protease cleavage site, the Clostridial toxin translocation domain, 5) the Clostridial toxin translocation domain, the exogenous protease cleavage site, the Clostridial toxin enzymatic domain and the retargeted peptide binding domain, or 6) the Clostridial toxin translocation domain, the exogenous protease cleavage site, the retargeted peptide binding domain and the Clostridial toxin enzymatic domain.

66. The medicament of 63 or use of 64, wherein the retargeted peptide binding domain is a galanin peptide binding domain, a PAR peptide binding domain, a somatostatin peptide binding domain, a neurotensin peptide binding domain, a SLURP peptide binding domain.

67. The medicament of 66, wherein the galanin peptide binding domain is a galanin or a galanin message-associated peptide (GMAP).

68. The medicament of 66, wherein the galanin peptide binding domain comprises SEQ ID NO: 67 or SEQ ID NO: 68.

69. The medicament of 66, wherein the PAR peptide binding domain is a PAR1 peptide, a PAR2 peptide, a PAR3 peptide and a PAR4 peptide.

70. The medicament of 66, wherein the PAR peptide binding domain comprises amino acids 42-47, amino acids 42-55, amino acids 29-64 or amino acids 1-64 of SEQ ID NO: 69; amino acids 35-40, amino acids 35-48, amino acids 24-59 or amino acids 1-59 of SEQ ID NO: 70; amino acids 39-44, amino acids 39-52, amino acids 26-60 or amino acids 1-60 of SEQ ID NO: 71; amino acids 48-53, amino acids 48-61, amino acids 35-70 or amino acids 1-70 of SEQ ID NO: 72.

71. The medicament of 66, wherein the somatostatin peptide binding domain is a somatostatin peptide.

72. The medicament of 66, wherein the somatostatin peptide binding domain comprises amino acids 99-116 of SEQ ID NO: 73.

73. The medicament of 66, wherein the neurotensin peptide binding domain a neurotensin or a neuromedin N.

74. The medicament of 66, wherein the neurotensin peptide binding domain comprises amino acids 143-148 or amino acids 151-163 of SEQ ID NO: 74.

75. The medicament of 66, wherein the SLURP peptide binding domain is a SLURP-1 or a SLURP-2.

76. The medicament of 66, wherein the SLURP peptide binding domain comprises amino acids 23-101 of SEQ ID NO: 75 or amino acids 23-95 of SEQ ID NO: 76.

77. The medicament of 63 or use of 64, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

78. The medicament of 63 or use of 64, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

79. The medicament of 63 or use of 64, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

80. The medicament or use of 79, wherein the urinary incontinence is an urge urinary incontinence, a stress urinary incontinence, an overflow urinary incontinence, a mixed urinary incontinence, or a continuous urinary incontinence.

81. The medicament or use of 79, wherein the detrusor dysfunction is a detrusor overactivity, a detrusor instability, or a detrusor-sphincter dyssynergia.

82. The medicament or use of 79, wherein the urogenital disorder associated with a prostate disorder is an urogenital disorder associated with benign prostatic hyperplasia, an urogenital disorder associated with prostatitis, or an urogenital disorder associated with prostatodynia.

83. The medicament or use of 79, wherein the urogenital disorder associated with a neurogenic dysfunction is an urogenital disorder associated with Parkinson's Disease, an urogenital disorder associated with multiple sclerosis, an urogenital disorder associated with spina bifida, an urogenital disorder associated with transverse myelitis, an urogenital disorder associated with stroke, an urogenital disorder associated with a spinal cord injury, an urogenital disorder associated with a spasm reflex, an urogenital disorder associated with a neurologic lesion of the spinal cord, or an urogenital disorder associated with a neurologic lesion of the brain.

84. The medicament of 63 or use of 64, wherein the exogenous protease cleavage site is a plant papain cleavage site, an insect papain cleavage site, a crustacian papain cleavage site, an enterokinase cleavage site, a human rhinovirus 3C protease cleavage site, a human enterovirus 3C protease cleavage site, a tobacco etch virus protease cleavage site, a Tobacco Vein Mottling Virus cleavage site, a subtilisin cleavage site, a hydroxylamine cleavage site, or a Caspase 3 cleavage site.

EXAMPLES

The following non-limiting examples are provided for illustrative purposes only in order to facilitate a more complete understanding of disclosed embodiments and are in no way intended to limit any of the embodiments disclosed in the present specification.

Example 1

Treatment of Urinary Incontinence

A 69 year old female complains of the inability to control the passage of urine. A physician diagnosis the patient with urinary incontinence having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates there is improvement of her ability to control the passage of urine. At one and three month check-ups, the woman indicates that she continues to have increased control over her ability to pass urine. This reduction in an urinary incontinence symptom indicates successful treatment with the composition comprising a TVEMP.

A 72 year old female complains of the inability to control the passage of urine, and leakage occurs especially when she coughs, sneezes, laughs or exercises. A physician diagnosis the patient with stress urinary incontinence having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates there is improvement of her ability to control the passage of urine, especially when she coughs, sneezes, laughs or exercises. At one and three month check-ups, the woman indicates that she continues to have increased control over her ability to pass urine. This reduction in a stress urinary incontinence symptom indicates successful treatment with the composition comprising a TVEMP.

A 62 year old male complains of the inability to control the passage of urine, experiencing a sudden need to urinate. A physician diagnosis the patient with urge urinary incontinence having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates there is improvement of his ability to control the passage of urine because of a reduced sudden need to urinate. At one and three month check-ups, the man indicates that he continues to have increased control over his ability to pass urine. This reduction in an urge urinary incontinence symptom indicates successful treatment with the composition comprising a TVEMP.

A 58 year old male complains of the inability to control the passage of urine because of leakage that occurs. A physician diagnosis the patient with overflow urinary incontinence having a neurological component involving abnormal neuron activity that is causing blockage. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates there is improvement of his ability to control the passage of urine because of reduced leakage. At one and three month check-ups, the man indicates that he continues to have increased control over his ability to pass urine. This reduction in an overflow urinary incontinence symptom indicates successful treatment with the composition comprising a TVEMP.

Example 2

Treatment of Overactive Bladder

A 58 year old male complains of increased urinary urgency. A physician diagnosis the patient with overactive bladder having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he has a reduced urgency to urinate. At one and three month check-ups, the man indicates that he continues to have a reduced urgency to urinate. This reduction in an overactive bladder symptom indicates successful treatment with the composition comprising a TVEMP.

A 66 year old female complains of having to wake up several times during the night to urinate. A physician determines that this is nocturia and diagnosis the patient with overactive bladder having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that she has a reduced need to wake up several times during the night to urinate. At one and three month check-ups, the woman indicates that she continues to have a reduced need to wake up several times during the night to urinate. This reduction in an overactive bladder symptom indicates successful treatment with the composition comprising a TVEMP.

A 47 year old female complains of having to urinate several times a day. A physician determines that this is polyuria and diagnosis the patient with overactive bladder having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that she has a reduced need to urinate during the day. At one and three month check-ups, the woman indicates that she continues to have a reduced need urinate during the day. This reduction in an overactive bladder symptom indicates successful treatment with the composition comprising a TVEMP.

A 67 year old male complains of the inability to control the passage of urine because of a sudden need to urinate. A physician determines that this is urge incontinence and diagnosis the patient with overactive bladder having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he has a reduced urgency to urinate. At one and three month check-ups, the man indicates that he continues to have a reduced urgency to urinate. This reduction in an overactive bladder symptom indicates successful treatment with the composition comprising a TVEMP.

Example 3

Treatment of Detrusor Dysfunction

A 44 year old female complains of uncontrollable bladder contractions. A physician determines that this is uninhibitable bladder contractions and diagnosis the patient with a detrusor dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in uncontrollable bladder contractions. At one and three month check-ups, the woman indicates that she continues to have a reduction in uncontrollable bladder contractions. This reduction in a detrusor dysfunction symptom indicates successful treatment with the composition comprising a TVEMP.

In an alternative scenario, the physician determines that this is uninhibitable bladder contractions and diagnosis the patient with detrusor overactivity having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in uncontrollable bladder contractions. At one and three month check-ups, the woman indicates that she continues to have a reduction in uncontrollable bladder contractions. This reduction in a detrusor overactivity symptom indicates successful treatment with the composition comprising a TVEMP.

In another alternative scenario, the physician determines that this is uninhibitable bladder contractions and diagnosis the patient with detrusor instability having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in uncontrollable bladder contractions. At one and three month check-ups, the woman indicates that she continues to have a reduction in uncontrollable bladder contractions. This reduction in a detrusor instability symptom indicates successful treatment with the composition comprising a TVEMP.

A 50 year old female complains of an urgency to urinate. A physician determines that this is urinary urgency and diagnosis the patient with a detrusor dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the urgency to urinate. At one and three month check-ups, the woman indicates that she continues to have a reduction in the urgency to urinate. This reduction in a detrusor dysfunction symptom indicates successful treatment with the composition comprising a TVEMP.

In an alternative scenario, the physician determines that this is urinary urgency and diagnosis the patient with detrusor overactivity having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the urgency to urinate. At one and three month check-ups, the woman indicates that she continues to have a reduction in the urgency to urinate. This reduction in a detrusor overactivity symptom indicates successful treatment with the composition comprising a TVEMP.

In another alternative scenario, the physician determines that this is urinary urgency and diagnosis the patient with detrusor instability having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the urgency to urinate. At one and three month check-ups, the woman indicates that she continues to have a reduction in the urgency to urinate. This reduction in a detrusor instability symptom indicates successful treatment with the composition comprising a TVEMP.

A 59 year old male complains of having to urinate all the time. A physician determines that this is urinary frequency and diagnosis the patient with a detrusor dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in the need to urinate all the time. At one and three month check-ups, the man indicates that he continues to have a reduction in the need to urinate all the time. This reduction in a detrusor dysfunction symptom indicates successful treatment with the composition comprising a TVEMP.

In an alternative scenario, the physician determines that this is urinary frequency and diagnosis the patient with detrusor overactivity having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in the need to urinate all the time. At one and three month check-ups, the man indicates that he continues to have a reduction in the need to urinate all the time. This reduction in a detrusor overactivity symptom indicates successful treatment with the composition comprising a TVEMP.

In another alternative scenario, the physician determines that this is urinary frequency and diagnosis the patient with detrusor instability having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in the need to urinate all the time. At one and three month check-ups, the man indicates that he continues to have a reduction in the need to urinate all the time. This reduction in a detrusor instability symptom indicates successful treatment with the composition comprising a TVEMP.

A 74 year old male complains of the involuntary loss of urine. A physician determines that this is enuresis and diagnosis the patient with a detrusor dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in the involuntary loss of urine. At one and three month check-ups, the man indicates that he continues to have a reduction in the involuntary loss of urine. This reduction in a detrusor dysfunction symptom indicates successful treatment with the composition comprising a TVEMP.

In an alternative scenario, the physician determines that this is enuresis and diagnosis the patient with detrusor overactivity having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in the involuntary loss of urine. At one and three month check-ups, the man indicates that he continues to have a reduction in the involuntary loss of urine. This reduction in a detrusor overactivity symptom indicates successful treatment with the composition comprising a TVEMP.

In another alternative scenario, the physician determines that this is enuresis and diagnosis the patient with detrusor instability having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in the involuntary loss of urine. At one and three month check-ups, the man indicates that he continues to have a reduction in the involuntary loss of urine. This reduction in a detrusor instability symptom indicates successful treatment with the composition comprising a TVEMP.

A 63 year old male complains of having to wake up several times during the night to urinate. A physician determines that this is nocturia and diagnosis the patient with a detrusor dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in need to wake up several times during the night to urinate. At one and three month check-ups, the man indicates that he continues to have a reduction in need to wake up several times during the night to urinate. This reduction in a detrusor dysfunction symptom indicates successful treatment with the composition comprising a TVEMP.

In an alternative scenario, the physician determines that this is nocturia and diagnosis the patient with detrusor overactivity having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in need to wake up several times during the night to urinate. At one and three month check-ups, the man indicates that he continues to have a reduction in need to wake up several times during the night to urinate. This reduction in a detrusor overactivity symptom indicates successful treatment with the composition comprising a TVEMP.

In another alternative scenario, the physician determines that this is nocturia and diagnosis the patient with detrusor instability having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in need to wake up several times during the night to urinate. At one and three month check-ups, the man indicates that he continues to have a reduction in need to wake up several times during the night to urinate. This reduction in a detrusor instability symptom indicates successful treatment with the composition comprising a TVEMP.

A 61 year old female complains of having to urinate several times a day. A physician determines that this is polyuria and diagnosis the patient with a detrusor dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the need to urinate several times a day. At one and three month check-ups, the woman indicates that she continues to have a reduction in the need to urinate several times a day. This reduction in a detrusor dysfunction symptom indicates successful treatment with the composition comprising a TVEMP.

In an alternative scenario, the physician determines that this is polyuria and diagnosis the patient with detrusor overactivity having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the need to urinate several times a day. At one and three month check-ups, the woman indicates that she continues to have a reduction in the need to urinate several times a day. This reduction in a detrusor overactivity symptom indicates successful treatment with the composition comprising a TVEMP.

In another alternative scenario, the physician determines that this is polyuria and diagnosis the patient with detrusor instability having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the need to urinate several times a day. At one and three month check-ups, the woman indicates that she continues to have a reduction in the need to urinate several times a day. This reduction in a detrusor instability symptom indicates successful treatment with the composition comprising a TVEMP.

A 65 year old female complains of the inability to control the passage of urine. A physician determines that this is urinary incontinence and diagnosis the patient with a detrusor dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from the treatment, and the woman indicates there is improvement of her ability to control the passage of urine. At one and three month check-ups, the woman indicates that she continues to have an improved ability to control the passage of urine since the treatment. This reduction in a detrusor dysfunction symptom indicates successful treatment with the composition comprising a TVEMP.

In an alternative scenario, the physician determines that this is urinary incontinence and diagnosis the patient with detrusor overactivity having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from the treatment, and the woman indicates there is improvement of her ability to control the passage of urine. At one and three month check-ups, the woman indicates that she continues to have an improved ability to control the passage of urine since the treatment. This reduction in a detrusor overactivity symptom indicates successful treatment with the composition comprising a TVEMP.

In another alternative scenario, the physician determines that this is urinary incontinence and diagnosis the patient with detrusor instability having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from the treatment, and the woman indicates there is improvement of her ability to control the passage of urine. At one and three month check-ups, the woman indicates that she continues to have an improved ability to control the passage of urine since the treatment. This reduction in a detrusor instability symptom indicates successful treatment with the composition comprising a TVEMP.

A 55 year old female complains of an interruption of urine flow when she urinates. A physician diagnosis the patient with a detrusor dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in urine flow interruption. At one and three month check-ups, the woman indicates that she continues to have a reduced urine flow interruption since the treatment. This reduction in a detrusor dysfunction symptom indicates successful treatment with the composition comprising a TVEMP.

In an alternative scenario, the physician diagnosis the patient with a detrusor-sphincter dyssynergia having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in urine flow interruption. At one and three month check-ups, the woman indicates that she continues to have a reduced urine flow interruption since the treatment. This reduction in a detrusor-sphincter dyssynergia symptom indicates successful treatment with the composition comprising a TVEMP.

A 53 year old male complains of increased bladder pressure. A physician determines that this is raised detrusor pressure and diagnosis the patient with a detrusor dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in bladder pressure. At one and three month check-ups, the man indicates that he continues to have a reduced bladder pressure since the treatment. This reduction in a detrusor dysfunction symptom indicates successful treatment with the composition comprising a TVEMP.

In an alternative scenario, the physician determines that this is raised detrusor pressure and diagnosis the patient with a detrusor-sphincter dyssynergia having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that there is a reduction in bladder pressure. At one and three month check-ups, the man indicates that he continues to have a reduced bladder pressure since the treatment. This reduction in a detrusor-sphincter dyssynergia symptom indicates successful treatment with the composition comprising a TVEMP.

A 75 year old male complains of the inability to urinate. A physician determines that this is urinary retention and diagnosis the patient with a detrusor dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he has regained the ability to urinate. At one and three month check-ups, the man indicates that he continues to have the ability to urinate. This reduction in a detrusor dysfunction symptom indicates successful treatment with the composition comprising a TVEMP.

In an alternative scenario, the physician determines that this is urinary retention and diagnosis the patient with a detrusor-sphincter dyssynergia having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that he has regained the ability to urinate. At one and three month check-ups, the man indicates that he continues to have the ability to urinate. This reduction in a detrusor-sphincter dyssynergia symptom indicates successful treatment with the composition comprising a TVEMP.

Example 4

Treatment of Lower Urinary Tract Dysfunction

A 69 year old male complains of the need to urinate suddenly. A physician determines that this is a urine storage problem and diagnosis the patient with a lower urinary tract dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in the sudden need to urinate. At one and three month check-ups, the man indicates that he still experiences a reduced need to urinate. This reduction in a lower urinary tract dysfunction indicates successful treatment with the composition comprising a TVEMP. In similar scenarios the patient could have complained of other storage symptoms of lower urinary tract dysfunction such as, e.g., urinary frequency, enuresis, polyuria, nocturia increased bladder sensation, decreased bladder sensation, absent bladder sensation, non-specific bladder sensation, and/or urinary incontinence. In each case, after diagnosis of lower urinary tract dysfunction, a physician would treat the patient as indicated above and there would be a reduction in the lower urinary tract dysfunction storage symptom.

A 70 year old male complains of having difficulty urinating and having to strain in order to urinate. A physician determines that this is a urine voiding problem and diagnosis the patient with a lower urinary tract dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that it is easier to urinate and he does not have to strain as much in order to urinate. At one and three month check-ups, the man indicates that he still experiences an easier time to urinate. This reduction in a lower urinary tract dysfunction indicates successful treatment with the composition comprising a TVEMP. In similar scenarios the patient could have complained of other voiding symptoms of lower urinary tract dysfunction such as, e.g., reduced urine flow, splitting or spraying of urine, intermittent urine flow, urinary hesitancy, and/or terminal dribble of urine. In each case, after diagnosis of lower urinary tract dysfunction, a physician would treat the patient as indicated above and there would be a reduction in the lower urinary tract dysfunction voiding symptom.

A 77 year old male complains of urine dribbling after he finishes urinating. A physician determines that this is a urine post-micturition problem and diagnosis the patient with a lower urinary tract dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in urine dribbling after he finishes urinating. At one and three month check-ups, the man indicates that he still experiences reduced dribbling after he finishes urinating. This reduction in a lower urinary tract dysfunction indicates successful treatment with the composition comprising a TVEMP. In similar scenarios the patient could have complained of other post-micturition symptoms of lower urinary tract dysfunction such as, e.g., sensation of incomplete emptying. In each case, after diagnosis of lower urinary tract dysfunction, a physician would treat the patient as indicated above and there would be a reduction in the lower urinary tract dysfunction post-micturition symptom.

Example 5

Treatment of Urinary Retention

A 79 year old female complains that she cannot urinate. A physician diagnosis the patient with urinary retention having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that she has regained the ability to urinate. At one and three month check-ups, the woman indicates that she still continues to have control over her ability to urinate. This reduction in a urinary retention symptom indicates successful treatment with the composition comprising a TVEMP.

Example 6

Treatment of Urinary Hesitancy

A 78 year old male complains that he has difficulty starting and/or maintaining his ability to urinate. A physician diagnosis the patient with urinary hesitancy having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he has less difficulty in starting and/or maintaining his ability to urinate. At one and three month check-ups, the man indicates that he still experiences less difficulty in starting and/or maintaining his ability to urinate. This reduction in a urinary hesitancy symptom indicates successful treatment with the composition comprising a TVEMP.

Example 7

Treatment of Polyuria

A 68 year old male complains that he has to urinate all the time during the day. A physician diagnosis the patient with polyuria having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that does not have to urinate as many times during the day as before the treatment. At one and three month check-ups, the man still indicates that does not have to urinate as many times during the day as before the treatment. This reduction in a polyuria symptom indicates successful treatment with the composition comprising a TVEMP.

Example 8

Treatment of Nocturia

A 57 year old female complains that she has to wake up several times during the night in order to urinate. A physician diagnosis the patient with nocturia having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that she does not have to get up as many times during the night to urinate as she did before the treatment. At one and three month check-ups, the woman still indicates that she does not have to get up as many times during the night to urinate as she did before the treatment. This reduction in a nocturia symptom indicates successful treatment with the composition comprising a TVEMP.

Example 9

Treatment of Chronic Urinary Tract Infection

A 76 year old female complains that she has urinary tract infections all the time. A physician determines that the chrionic urinary tract infections is abacterial and diagnosis the patient with urogential disorder having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the physician indicates that she does not have a urinary tract infection. At one and three month check-ups, the woman indicates that she has not had a urinary tract infection since the treatment. This reduction in a urinary tract infection symptom indicates successful treatment with the composition comprising a TVEMP.

A 75 year old female complains that she has urinary tract infections all the time. A physician determines that the chrionic urinary tract infection is due to vesicoureteral reflux and diagnosis the patient with urogential disorder having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the physician determines that the abnormal backup of urine from the bladder to the kidneys is reduced in the patient. At one and three month check-ups, the woman indicates that she has not had a urinary tract infection since the treatment. This reduction in a urinary tract infection symptom indicates successful treatment with the composition comprising a TVEMP.

Example 10

Treatment of Urogenital Disorder Associated with a Prostate Disorder

A 78 year old male complains that he has difficulty starting and/or maintaining his ability to urinate. A physician determines that he has benign prostatic hyperplasia and that this enlargement is blocking the normal flow of urine. The physician diagnosis the patient with urinary hesitancy associated with benign prostatic hyperplasia having a neurological component involving abnormal neuron activity. The man is treated by injecting a composition comprising a TVEMP as disclosed in the present specification into the prostate and/or in the surrounding area of the prostate depending on the location of abnormal neuron activity. The patient's condition is monitored and after about 1-2 weeks from the treatment, the man indicates that he has less difficulty in starting and/or maintaining his ability to urinate. The physician determines that the size of the prostate has reduced since the treatment. At one and three month check-ups, the man indicates that he still experiences less difficulty in starting and/or maintaining his ability to urinate. This reduction in a urinary hesitancy symptom associated with benign prostatic hyperplasia indicates successful treatment with the composition comprising a TVEMP.

Example 11

Treatment of Urogenital Disorder Associated with a Neurogenic Dysfunction

A 81 year old female diagnosed with Parkinson's Disease complains about having a sudden need to urinate. A physician determines that this urinary urgency is due to her Parkinson's Disease and diagnosis the patient with urogential disorder associated with a neurogenic dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the sudden need to urinate. At one and three month check-ups, the woman indicates that she continues to experience a reduced sudden need to urinate. This reduction in a urogenital disorder symptom associated with a neurogenic dysfunction indicates successful treatment with the composition comprising a TVEMP.

A 39 year old female diagnosed with multiple sclerosis complains about having a need to urinate all the time. A physician determines that this urinary frequency is due to her multiple sclerosis and diagnosis the patient with urogential disorder associated with a neurogenic dysfunction having a neurological component involving abnormal neuron activity. The woman is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the woman indicates that there is a reduction in the need to urinate all the time. At one and three month check-ups, the woman indicates that she still experiences a reduced need to urinate all the time. This reduction in a urogenital disorder symptom associated with a neurogenic dysfunction indicates successful treatment with the composition comprising a TVEMP.

A 12 year old male diagnosed with spina bifida complains about the inability to control the passage of urine. A physician determines that this urinary incontinence is due to his spina bifida and diagnosis the patient with urogential disorder associated with a neurogenic dysfunction having a neurological component involving abnormal neuron activity. The boy is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the boy indicates that he has an increased ability to control the passage or urine. At one and three month check-ups, the boy indicates that he still experiences an increased ability to control the passage or urine. This reduction in a urogenital disorder symptom associated with a neurogenic dysfunction indicates successful treatment with the composition comprising a TVEMP.

A 84 year old male who experienced a stroke complains about not being able to urinate. A physician determines that this urinary retention is due to his stroke and diagnosis the patient with urogential disorder associated with a neurogenic dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that he can urinate. At one and three month check-ups, the man indicates that he continues to experience the ability to urinate. This reduction in a urogenital disorder symptom associated with a neurogenic dysfunction indicates successful treatment with the composition comprising a TVEMP.

A 23 year old man suffering from a spinal cord injury resulting from a car accident complains about the inability to control the passage of urine. A physician determines that this urinary incontinence is due to his spinal cord injury and diagnosis the patient with urogential disorder associated with a neurogenic dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, or lower pelvic muscles. The patient's condition is monitored and after about 1-3 days from treatment, and the man indicates that he has an increased ability to control the passage or urine. At one and three month check-ups, the man indicates that he still experiences an increased ability to control the passage or urine. This reduction in a urogenital disorder symptom associated with a neurogenic dysfunction indicates successful treatment with the composition comprising a TVEMP.

A 63 year old male who has cancerous lesion in his brain complains about having a need to urinate all the time. A physician determines that this urinary frequency is due to his lesion and diagnosis the patient with urogential disorder associated with a neurogenic dysfunction having a neurological component involving abnormal neuron activity. The man is treated by injecting urethroscopically a composition comprising a TVEMP as disclosed in the present specification. Depending on the location of abnormal neuron activity, the toxin can be administered into e.g., the detrusor, the bladder neck including the external and internal urethral sphincters, the trigone, the bladder dome or other areas of the bladder wall, and/or other areas surrounding the bladder, such as the urethra, ureter, urogenital diaphragm, lower pelvic muscles, prostate, bulbourethral gland, bulb, crus or penis. The patient's condition is monitored and after about 1-3 days from treatment, and the man indicates that there is a reduction in the need to urinate all the time. At one and three month check-ups, the man indicates that he still experiences a reduced need to urinate all the time. This reduction in a urogenital disorder symptom associated with a neurogenic dysfunction indicates successful treatment with the composition comprising a TVEMP.

In closing, it is to be understood that although aspects of the present specification have been described with reference to the various embodiments, one skilled in the art will readily appreciate that the specific examples disclosed are only illustrative of the principles of the subject matter disclosed in the present specification. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing quantities of ingredients, properties such as molecular weight, reaction conditions, and so forth used in the specification and claims are to be understood as being modified in all instances by the term "about." As used herein, the term "about" when qualifying a value of a stated item, number, percentage, parameter, or term refers to a range of plus or minus ten percent of the value of the stated item, number, percentage, parameter, or term. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

All patents, patent publications, and other publications referenced and identified in the present specification are individually and expressly incorporated herein by reference in their entirety for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed:

1. A method of treating urogenital-neurological disorder in a mammal, the method comprising the step of administering to the mammal in need thereof a therapeutically effective amount of a composition including a Targeted Vesicular Exocytosis Modulating Protein (TVEMP) comprising a retargeted peptide binding domain, a Clostridial toxin translocation domain and a Clostridial toxin enzymatic domain, wherein the retargeted peptide binding domain is a galanin peptide binding domain, a PAR peptide binding domain, a somatostatin peptide binding domain, a neurotensin peptide binding domain, or a SLURP peptide binding domain, and wherein administration of the composition reduces a symptom of the urogenital-neurological disorder, thereby treating the mammal.

2. The method of claim 1, wherein the TVEMP comprises a linear amino-to-carboxyl single polypeptide order of 1) the Clostridial toxin enzymatic domain, the Clostridial toxin translocation domain, the retargeted peptide binding domain, 2) the Clostridial toxin enzymatic domain, the retargeted peptide binding domain, the Clostridial toxin translocation domain, 3) the retargeted peptide binding domain, the Clostridial toxin translocation domain, and the Clostridial toxin enzymatic domain, 4) the retargeted peptide binding domain, the Clostridial toxin enzymatic domain, the Clostridial toxin translocation domain, 5) the Clostridial toxin translocation domain, the Clostridial toxin enzymatic domain and the retargeted peptide binding domain, or 6) the Clostridial toxin translocation domain, the retargeted peptide binding domain and the Clostridial toxin enzymatic domain.

3. The method of claim 1, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

4. The method of claim 1, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

5. The method of claim 1, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

6. A method of treating urogenital-neurological disorder in a mammal, the method comprising the step of administering to the mammal in need thereof a therapeutically effective amount of a composition including a TVEMP comprising a retargeted peptide binding domain, a Clostridial toxin translocation domain, a Clostridial toxin enzymatic domain, and an exogenous protease cleavage site, wherein the retargeted peptide binding domain is a galanin peptide binding domain, a PAR peptide binding domain, a somatostatin peptide binding domain, a neurotensin peptide binding domain, or a SLURP peptide binding domain, and wherein administration of the composition reduces a symptom of the urogenital-neurological disorder, thereby treating the mammal.

7. The method of claim 6, wherein the TVEMP comprises a linear amino-to-carboxyl single polypeptide order of 1) the Clostridial toxin enzymatic domain, the exogenous protease cleavage site, the Clostridial toxin translocation domain, the retargeted peptide binding domain, 2) the Clostridial toxin enzymatic domain, the exogenous protease cleavage site, the retargeted peptide binding domain, the Clostridial toxin translocation domain, 3) the retargeted peptide binding domain, the Clostridial toxin translocation domain, the exogenous protease cleavage site and the Clostridial toxin enzymatic domain, 4) the retargeted peptide binding domain, the Clostridial toxin enzymatic domain, the exogenous protease cleavage site, the Clostridial toxin translocation domain, 5) the Clostridial toxin translocation domain, the exogenous protease cleavage site, the Clostridial toxin enzymatic domain and the retargeted peptide binding domain, or 6) the Clostridial toxin translocation domain, the exogenous protease cleavage site, the retargeted peptide binding domain and the Clostridial toxin enzymatic domain.

8. The method of claim 6, wherein the Clostridial toxin translocation domain is a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, or a BuNT translocation domain.

9. The method of claim 6, wherein the Clostridial toxin enzymatic domain is a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, or a BuNT enzymatic domain.

10. The method of claim 6, wherein the exogenous protease cleavage site is a plant papain cleavage site, an insect papain cleavage site, a crustacian papain cleavage site, an enterokinase cleavage site, a human rhinovirus 3C protease cleavage site, a human enterovirus 3C protease cleavage site, a tobacco etch virus protease cleavage site, a Tobacco Vein Mottling Virus cleavage site, a subtilisin cleavage site, a hydroxylamine cleavage site, or a Caspase 3 cleavage site.

11. The method of claim 6, wherein the urogenital-neurological disorder is urinary incontinence, overactive bladder, detrusor dysfunction, lower urinary tract dysfunction, urinary retention, urinary hesitancy, polyuria, nocturia, chronic urinary tract infection, an urogenital disorder associated with a prostate disorder, an urogenital disorder associated with a uterine disorder, or an urogenital disorder associated with a neurogenic dysfunction.

* * * * *

UNITED STATES PATENT AND TRADEMARK OFFICE
CERTIFICATE OF CORRECTION

PATENT NO.       : 8,198,229 B2
APPLICATION NO.  : 12/781078
DATED            : June 12, 2012
INVENTOR(S)      : Joseph Francis et al.

It is certified that error appears in the above-identified patent and that said Letters Patent is hereby corrected as shown below:

On first page, in column 1, field (54), and column 1, line 4, in "Title", delete "ENDOPEPIDASES" and insert -- ENDOPEPTIDASES --, therefor.

In column 2, line 4, delete "urogentital" and insert -- urogenital --, therefor.

In column 4, line 39, delete "synonomous" and insert -- synonymous --, therefor.

In column 40, line 7, delete "crustacian" and insert -- crustacean --, therefor.

In column 40, line 25, delete "crustacian" and insert -- crustacean --, therefor.

In column 48, lines 55-56, delete "oxy chloro" and insert -- oxychloro --, therefor.

In column 51, line 65, delete "invertebral" and insert -- intervertebral --, therefor.

In column 53, line 31, delete "Reposrt" and insert -- Report --, therefor.

In column 54, line 35, delete "invertebral" and insert -- intervertebral --, therefor.

In column 63, line 6, delete "μg" and insert -- pg --, therefor.

In column 63, line 10, delete "μg" and insert -- pg --, therefor.

In column 63, line 15, delete "μg" and insert -- pg --, therefor.

In column 63, line 15, delete "μg" and insert -- pg --, therefor.

In column 63, line 15, delete "μg" and insert -- pg --, therefor.

In column 63, line 15, delete "μg" and insert -- pg --, therefor.

In column 63, line 21, delete "μg" and insert -- pg --, therefor.

In column 63, line 21, delete "μg" and insert -- pg --, therefor.

In column 63, line 22, delete "μg" and insert -- pg --, therefor.

In column 63, line 22, delete "μg" and insert -- pg --, therefor.

In column 66, line 66, delete "crustacian" and insert -- crustacean --, therefor.

In column 71, line 20, delete "crustacian" and insert -- crustacean --, therefor.

In column 84-85, line 66 (Col. 84), 1 (Col. 85), delete "chrionic" and insert -- chronic --, therefor.

Signed and Sealed this
Twenty-third Day of October, 2012

David J. Kappos
*Director of the United States Patent and Trademark Office*

CERTIFICATE OF CORRECTION (continued)
U.S. Pat. No. 8,198,229 B2

In column 85, line 2, delete "urogential" and insert -- urogenital --, therefor.

In column 85, lines 21-22, delete "chrionic" and insert -- chronic --, therefor.

In column 85, line 23, delete "urogential" and insert -- urogenital --, therefor.

In column 86, line 8, delete "urogential" and insert -- urogenital --, therefor.

In column 86, line 30, delete "urogential" and insert -- urogenital --, therefor.

In column 86, line 52, delete "urogential" and insert -- urogenital --, therefor.

In column 87, line 8, delete "urogential" and insert -- urogenital --, therefor.

In column 87, line 31, delete "urogential" and insert -- urogenital --, therefor.

In column 87, line 53, delete "urogential" and insert -- urogenital --, therefor.

In column 180, line 39, in claim 10, delete "crustacian" and insert -- crustacean --, therefor.

SEQUENCE LISTING

```
<160> NUMBER OF SEQ ID NOS: 76

<210> SEQ ID NO 1
<211> LENGTH: 1296
<212> TYPE: PRT
<213> ORGANISM: Clostridium botulinum Serotype A

<400> SEQUENCE: 1

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
```

```
            195                 200                 205
Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
                370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
610                 615                 620
```

-continued

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Phe Val Gly Ala Leu
            645                 650                 655

Ile Phe Ser Gly Ala Val Ile Leu Glu Phe Ile Pro Glu Ile Ala
                660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg Leu
            1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
                1045                1050                1055

```
Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
        1075                1080                1085

Asp Asn Gln Ser Asn Ser Gly Ile Leu Lys Asp Phe Trp Gly Asp Tyr
    1090                1095                1100

Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1291
<212> TYPE: PRT
<213> ORGANISM: Clostridium botulinum Serotype B

<400> SEQUENCE: 2

Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Thr Gly Arg
             20                  25                  30

Tyr Tyr Lys Ala Phe Lys Ile Thr Asp Arg Ile Trp Ile Ile Pro Glu
         35                  40                  45

Arg Tyr Thr Phe Gly Tyr Lys Pro Glu Asp Phe Asn Lys Ser Ser Gly
     50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140
```

```
Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
            165                 170                 175

Ile Gln Asn His Phe Ala Ser Arg Glu Gly Phe Gly Gly Ile Met Gln
        180                 185                 190

Met Lys Phe Cys Pro Glu Tyr Val Ser Val Phe Asn Asn Val Gln Glu
            195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
            245                 250                 255

Phe Met Gln Ser Thr Asp Ala Ile Gln Ala Glu Glu Leu Tyr Thr Phe
        260                 265                 270

Gly Gly Gln Asp Pro Ser Ile Ile Thr Pro Ser Thr Asp Lys Ser Ile
            275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
            485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
            530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
```

```
                565                 570                 575
Tyr Ile Lys Thr Ala Asn Lys Val Val Glu Ala Gly Leu Phe Ala Gly
                580                 585                 590

Trp Val Lys Gln Ile Val Asn Asp Phe Val Ile Glu Ala Asn Lys Ser
                595                 600                 605

Asn Thr Met Asp Lys Ile Ala Asp Ile Ser Leu Ile Val Pro Tyr Ile
                610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
                690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Lys Ser Asn Ile Asn Ile Asp
                740                 745                 750

Phe Asn Asp Ile Asn Ser Lys Leu Asn Glu Gly Ile Asn Gln Ala Ile
                755                 760                 765

Asp Asn Ile Asn Asn Phe Ile Asn Gly Cys Ser Val Ser Tyr Leu Met
                770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
                835                 840                 845

Leu Ile Glu Met Phe Asn Lys Tyr Asn Ser Glu Ile Leu Asn Asn Ile
                850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
                900                 905                 910

Gln Asn Gln Asn Ile Ile Phe Asn Ser Val Phe Leu Asp Phe Ser Val
                915                 920                 925

Ser Phe Trp Ile Arg Ile Pro Lys Tyr Lys Asn Asp Gly Ile Gln Asn
                930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
                980                 985                 990
```

-continued

Glu Asp Ile Ser Glu Tyr Ile Asn Arg Trp Phe Phe Val Thr Ile Thr
    995                 1000                1005

Asn Asn Leu Asn Asn Ala Lys Ile Tyr Ile Asn Gly Lys Leu Glu Ser
    1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
                1045                1050                1055

Lys Tyr Phe Ser Ile Phe Asn Thr Glu Leu Ser Gln Ser Asn Ile Glu
                1060                1065                1070

Glu Arg Tyr Lys Ile Gln Ser Tyr Ser Glu Tyr Leu Lys Asp Phe Trp
                1075                1080                1085

Gly Asn Pro Leu Met Tyr Asn Lys Glu Tyr Tyr Met Phe Asn Ala Gly
                1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
                1125                1130                1135

Arg Asp Leu Tyr Ile Gly Glu Lys Phe Ile Ile Arg Arg Lys Ser Asn
                1140                1145                1150

Ser Gln Ser Ile Asn Asp Asp Ile Val Arg Lys Glu Asp Tyr Ile Tyr
                1155                1160                1165

Leu Asp Phe Phe Asn Leu Asn Gln Glu Trp Arg Val Tyr Thr Tyr Lys
                1170                1175                1180

Tyr Phe Lys Lys Glu Glu Glu Lys Leu Phe Leu Ala Pro Ile Ser Asp
1185                1190                1195                1200

Ser Asp Glu Phe Tyr Asn Thr Ile Gln Ile Lys Glu Tyr Asp Glu Gln
                1205                1210                1215

Pro Thr Tyr Ser Cys Gln Leu Leu Phe Lys Lys Asp Glu Glu Ser Thr
                1220                1225                1230

Asp Glu Ile Gly Leu Ile Gly Ile His Arg Phe Tyr Glu Ser Gly Ile
                1235                1240                1245

Val Phe Glu Glu Tyr Lys Asp Tyr Phe Cys Ile Ser Lys Trp Tyr Leu
                1250                1255                1260

Lys Glu Val Lys Arg Lys Pro Tyr Asn Leu Lys Leu Gly Cys Asn Trp
1265                1270                1275                1280

Gln Phe Ile Pro Lys Asp Glu Gly Trp Thr Glu
                1285                1290

<210> SEQ ID NO 3
<211> LENGTH: 1291
<212> TYPE: PRT
<213> ORGANISM: Clostridium botulinum Serotype C1

<400> SEQUENCE: 3

Met Pro Ile Thr Ile Asn Asn Phe Asn Tyr Ser Asp Pro Val Asp Asn
  1               5                  10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

-continued

```
Ser Asp Lys Asp Pro Phe Leu Lys Glu Ile Ile Lys Leu Phe Lys Arg
             85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Thr Pro Ile Asn Thr Phe Asp
        115                 120                 125

Phe Asp Val Asp Phe Asn Ser Val Asp Val Lys Thr Arg Gln Gly Asn
        130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
        210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
        290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
        355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
        435                 440                 445

Lys Thr Leu Asp Cys Arg Glu Leu Leu Val Lys Asn Thr Asp Leu Pro
        450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
            500                 505                 510
```

```
Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
        530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
        595                 600                 605

Phe Thr Thr Asn Ile Leu Arg Lys Asp Thr Leu Asp Lys Ile Ser Asp
        610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Pro Glu Phe Thr Ile Pro Ala Leu Gly
            660                 665                 670

Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Asn Ile Asn Lys Phe Ile Arg
        770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
        850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
```

930             935             940
Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr Ile
    1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
        1075                1080                1085

Phe Asn Ser Leu Gln Tyr Thr Asn Val Val Lys Asp Tyr Trp Gly Asn
    1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
        1155                1160                1165

Tyr Phe Asp Met Thr Ile Asn Asn Lys Ala Tyr Asn Leu Phe Met Lys
    1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
                1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr Leu
    1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
                1285                1290

<210> SEQ ID NO 4
<211> LENGTH: 1276
<212> TYPE: PRT
<213> ORGANISM: Clostridium botulinum Serotype D

<400> SEQUENCE: 4

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr

-continued

```
                 20                  25                  30
Pro Val Lys Ala Phe Met Ile Thr Gln Asn Ile Trp Val Ile Pro Glu
             35                  40                  45

Arg Phe Ser Ser Asp Thr Asn Pro Ser Leu Ser Lys Pro Pro Arg Pro
             50                  55                  60

Thr Ser Lys Tyr Gln Ser Tyr Asp Pro Ser Tyr Leu Ser Thr Asp
 65                  70                  75                  80

Glu Gln Lys Asp Thr Phe Leu Lys Gly Ile Ile Lys Leu Phe Lys Arg
                         85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
            115                 120                 125

Phe Thr Arg His Thr Thr Asn Ile Ala Val Glu Lys Phe Glu Asn Gly
            130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
            195                 200                 205

Gln Ser Ser Ala Val Leu Gly Lys Ser Ile Phe Cys Met Asp Pro Val
            210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
            275                 280                 285

Leu Arg Glu Lys Ala Leu Gly His Tyr Lys Asp Ile Ala Lys Arg Leu
            290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
            370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
            435                 440                 445
```

```
Thr Cys Ile Lys Val Lys Asn Asn Arg Leu Pro Tyr Val Ala Asp Lys
450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Ser Ile
                485                 490                 495

Leu Asp Gly Gln Val Pro Ile Asn Pro Glu Ile Val Asp Pro Leu Leu
                500                 505                 510

Pro Asn Val Asn Met Glu Pro Leu Asn Leu Pro Gly Glu Glu Ile Val
                515                 520                 525

Phe Tyr Asp Asp Ile Thr Lys Tyr Val Asp Tyr Leu Asn Ser Tyr Tyr
530                 535                 540

Tyr Leu Glu Ser Gln Lys Leu Ser Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
                580                 585                 590

Leu Phe Leu Asn Trp Ala Asn Glu Val Val Glu Asp Phe Thr Thr Asn
                595                 600                 605

Ile Met Lys Lys Asp Thr Leu Asp Lys Ile Ser Asp Val Ser Val Ile
                610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
                660                 665                 670

Tyr Ser Ser Ile Gln Glu Arg Glu Lys Ile Ile Lys Thr Ile Glu Asn
                675                 680                 685

Cys Leu Glu Gln Arg Val Lys Arg Trp Lys Asp Ser Tyr Gln Trp Met
                690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735

Lys Ile Asp Leu Glu Tyr Lys Lys Tyr Ser Gly Ser Asp Lys Glu Asn
                740                 745                 750

Ile Lys Ser Gln Val Glu Asn Leu Lys Asn Ser Leu Asp Val Lys Ile
                755                 760                 765

Ser Glu Ala Met Asn Asn Ile Asn Lys Phe Ile Arg Glu Cys Ser Val
770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
                820                 825                 830

Asn Glu Ser Phe Glu Asn Thr Met Pro Phe Asn Ile Phe Ser Tyr Thr
                835                 840                 845

Asn Asn Ser Leu Leu Lys Asp Ile Ile Asn Glu Tyr Phe Asn Ser Ile
                850                 855                 860

Asn Asp Ser Lys Ile Leu Ser Leu Gln Asn Lys Lys Asn Ala Leu Val
865                 870                 875                 880
```

```
Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Gly Asp
        900                 905                 910

Lys Ile Ile Val Asn Leu Asn Asn Ile Leu Tyr Ser Ala Ile Tyr
        915                 920                 925

Glu Asn Ser Ser Val Ser Phe Trp Ile Lys Ile Ser Lys Asp Leu Thr
        930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
                980                 985                 990

Leu Ser His Thr Gly Tyr Thr Asn Lys Trp Phe Phe Val Thr Ile Thr
                995                 1000                1005

Asn Asn Ile Met Gly Tyr Met Lys Leu Tyr Ile Asn Gly Glu Leu Lys
        1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
                1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
        1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
                1140                1145                1150

Asp Asn Ile Ile Leu His Met Leu Tyr Asn Ser Arg Lys Tyr Met Ile
                1155                1160                1165

Ile Arg Asp Thr Asp Thr Ile Tyr Ala Thr Gln Gly Gly Glu Cys Ser
        1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
                1205                1210                1215

Cys Ser Gln Ile Phe Ser Ser Phe Arg Glu Asn Thr Met Leu Leu Ala
                1220                1225                1230

Asp Ile Tyr Lys Pro Trp Arg Phe Ser Phe Lys Asn Ala Tyr Thr Pro
        1235                1240                1245

Val Ala Val Thr Asn Tyr Glu Thr Lys Leu Leu Ser Thr Ser Ser Phe
        1250                1255                1260

Trp Lys Phe Ile Ser Arg Asp Pro Gly Trp Val Glu
1265                1270                1275

<210> SEQ ID NO 5
<211> LENGTH: 1252
<212> TYPE: PRT
```

<213> ORGANISM: Clostridium botulinum Serotype E

<400> SEQUENCE: 5

```
Met Pro Lys Ile Asn Ser Phe Asn Tyr Asn Asp Pro Val Asn Asp Arg
 1               5                  10                  15
Thr Ile Leu Tyr Ile Lys Pro Gly Gly Cys Gln Glu Phe Tyr Lys Ser
                20                  25                  30
Phe Asn Ile Met Lys Asn Ile Trp Ile Ile Pro Glu Arg Asn Val Ile
            35                  40                  45
Gly Thr Thr Pro Gln Asp Phe His Pro Pro Thr Ser Leu Lys Asn Gly
        50                  55                  60
Asp Ser Ser Tyr Tyr Asp Pro Asn Tyr Leu Gln Ser Asp Glu Glu Lys
 65                 70                  75                  80
Asp Arg Phe Leu Lys Ile Val Thr Lys Ile Phe Asn Arg Ile Asn Asn
                85                  90                  95
Asn Leu Ser Gly Gly Ile Leu Leu Glu Glu Leu Ser Lys Ala Asn Pro
            100                 105                 110
Tyr Leu Gly Asn Asp Asn Thr Pro Asp Asn Gln Phe His Ile Gly Asp
        115                 120                 125
Ala Ser Ala Val Glu Ile Lys Phe Ser Asn Gly Ser Gln Asp Ile Leu
130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
            180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
```

```
                        405                 410                 415
Ser Val Lys Gly Ile Arg Lys Ser Ile Cys Ile Glu Ile Asn Asn Gly
            420                 425                 430

Glu Leu Phe Phe Val Ala Ser Glu Asn Ser Tyr Asn Asp Asp Asn Ile
            435                 440                 445

Asn Thr Pro Lys Glu Ile Asp Asp Thr Val Thr Ser Asn Asn Asn Tyr
            450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
            500                 505                 510

Asp Val Asn Glu Leu Asn Val Phe Phe Tyr Leu Asp Ala Gln Lys Val
            515                 520                 525

Pro Glu Gly Glu Asn Asn Val Asn Leu Thr Ser Ser Ile Asp Thr Ala
            530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
                565                 570                 575

Gln Gln Val Leu Val Asp Phe Thr Thr Glu Ala Asn Gln Lys Ser Thr
            580                 585                 590

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830
```

```
Asp Lys Ile Leu Ile Ser Tyr Phe Asn Lys Phe Phe Lys Arg Ile Lys
    835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
                900                 905                 910

Lys Asn Phe Ser Ile Ser Phe Trp Val Arg Ile Pro Asn Tyr Asp Asn
                915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
                980                 985                 990

Val Thr Ile Thr Asn Asp Arg Leu Gly Asp Ser Lys Leu Tyr Ile Asn
                995                 1000                1005

Gly Asn Leu Ile Asp Gln Lys Ser Ile Leu Asn Leu Gly Asn Ile His
    1010                1015                1020

Val Ser Asp Asn Ile Leu Phe Lys Ile Val Asn Cys Ser Tyr Thr Arg
1025                1030                1035                1040

Tyr Ile Gly Ile Arg Tyr Phe Asn Ile Phe Asp Lys Glu Leu Asp Glu
                1045                1050                1055

Thr Glu Ile Gln Thr Leu Tyr Ser Asn Glu Pro Asn Thr Asn Ile Leu
                1060                1065                1070

Lys Asp Phe Trp Gly Asn Tyr Leu Leu Tyr Asp Lys Glu Tyr Tyr Leu
                1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
                1140                1145                1150

Val Ala Ser Lys Thr His Leu Phe Pro Leu Tyr Ala Asp Thr Ala Thr
    1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
                1220                1225                1230

Thr Asn Ser Asn Gly Cys Phe Trp Asn Phe Ile Ser Glu Glu His Gly
    1235                1240                1245

Trp Gln Glu Lys
    1250
```

<210> SEQ ID NO 6
<211> LENGTH: 1274
<212> TYPE: PRT
<213> ORGANISM: Clostridium botulinum Serotype F

<400> SEQUENCE: 6

```
Met Pro Val Ala Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
130                 135                 140

Val Glu Ser Ser Met Leu Leu Asn Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380
```

```
Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
            405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
            435                 440                 445

Asn Asn Ser Glu Leu Phe Phe Val Ala Ser Glu Ser Ser Tyr Asn Glu
            450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Gln Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
            530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
            565                 570                 575

Phe Ile Asp Thr Ile Asn Lys Pro Val Asn Ala Ala Leu Phe Ile Asp
            580                 585                 590

Trp Ile Ser Lys Val Ile Arg Asp Phe Thr Thr Glu Ala Thr Gln Lys
            595                 600                 605

Ser Thr Val Asp Lys Ile Ala Asp Ile Ser Leu Ile Val Pro Tyr Val
610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
            645                 650                 655

Glu Leu Thr Ile Pro Val Ile Leu Val Phe Thr Ile Lys Ser Tyr Ile
            660                 665                 670

Asp Ser Tyr Glu Asn Lys Asn Lys Ala Ile Lys Ala Ile Asn Asn Ser
            675                 680                 685

Leu Ile Glu Arg Glu Ala Lys Trp Lys Glu Ile Tyr Ser Trp Ile Val
690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
            725                 730                 735

Ile Glu Tyr Lys Tyr Asn Asn Tyr Thr Ser Asp Glu Lys Asn Arg Leu
            740                 745                 750

Glu Ser Glu Tyr Asn Ile Asn Asn Ile Glu Glu Leu Asn Lys Lys
            755                 760                 765

Val Ser Leu Ala Met Lys Asn Ile Glu Arg Phe Met Thr Glu Ser Ser
            770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
```

-continued

```
            805                 810                 815
Asp His Arg Ser Ile Leu Gly Glu Gln Thr Asn Glu Leu Ser Asp Leu
            820                 825                 830

Val Thr Ser Thr Leu Asn Ser Ser Ile Pro Phe Glu Leu Ser Ser Tyr
            835                 840                 845

Thr Asn Asp Lys Ile Leu Ile Ile Tyr Phe Asn Arg Leu Tyr Lys Lys
            850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                    885                 890                 895

Tyr Ile Tyr Ser Thr Asn Arg Asn Gln Phe Gly Ile Tyr Asn Ser Arg
            900                 905                 910

Leu Ser Glu Val Asn Ile Ala Gln Asn Asn Asp Ile Tyr Asn Ser
            915                 920                 925

Arg Tyr Gln Asn Phe Ser Ile Ser Phe Trp Val Arg Ile Pro Lys His
            930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
                    965                 970                 975

Cys Glu Ile Ile Trp Thr Leu Gln Asp Thr Ser Gly Asn Lys Glu Asn
            980                 985                 990

Leu Ile Phe Arg Tyr Glu Glu Leu Asn Arg Ile Ser Asn Tyr Ile Asn
            995                 1000                1005

Lys Trp Ile Phe Val Thr Ile Thr Asn Asn Arg Leu Gly Asn Ser Arg
            1010                1015                1020

Ile Tyr Ile Asn Gly Asn Leu Ile Val Glu Lys Ser Ile Ser Asn Leu
1025                1030                1035                1040

Gly Asp Ile His Val Ser Asp Asn Ile Leu Phe Lys Ile Val Gly Cys
                    1045                1050                1055

Asp Asp Glu Thr Tyr Val Gly Ile Arg Tyr Phe Lys Val Phe Asn Thr
            1060                1065                1070

Glu Leu Asp Lys Thr Glu Ile Glu Thr Leu Tyr Ser Asn Glu Pro Asp
            1075                1080                1085

Pro Ser Ile Leu Lys Asn Tyr Trp Gly Asn Tyr Leu Leu Tyr Asn Lys
            1090                1095                1100

Lys Tyr Tyr Leu Phe Asn Leu Leu Arg Lys Asp Lys Tyr Ile Thr Leu
1105                1110                1115                1120

Asn Ser Gly Ile Leu Asn Ile Asn Gln Gln Arg Gly Val Thr Glu Gly
                    1125                1130                1135

Ser Val Phe Leu Asn Tyr Lys Leu Tyr Glu Gly Val Glu Val Ile Ile
            1140                1145                1150

Arg Lys Asn Gly Pro Ile Asp Ile Ser Asn Thr Asp Asn Phe Val Arg
            1155                1160                1165

Lys Asn Asp Leu Ala Tyr Ile Asn Val Val Asp Arg Gly Val Glu Tyr
            1170                1175                1180

Arg Leu Tyr Ala Asp Thr Lys Ser Glu Lys Glu Lys Ile Ile Arg Thr
1185                1190                1195                1200

Ser Asn Leu Asn Asp Ser Leu Gly Gln Ile Ile Val Met Asp Ser Ile
                    1205                1210                1215

Gly Asn Asn Cys Thr Met Asn Phe Gln Asn Asn Asn Gly Ser Asn Ile
            1220                1225                1230
```

```
Gly Leu Leu Gly Phe His Ser Asn Asn Leu Val Ala Ser Ser Trp Tyr
        1235                1240                1245

Tyr Asn Asn Ile Arg Arg Asn Thr Ser Ser Asn Gly Cys Phe Trp Ser
        1250                1255                1260

Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum Serotype G

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335
```

```
Tyr Ser Val Asp Lys Asp Lys Phe Asp Lys Leu Tyr Lys Ala Leu Met
                340                 345                 350
Phe Gly Phe Thr Glu Thr Asn Leu Ala Gly Glu Tyr Gly Ile Lys Thr
            355                 360                 365
Arg Tyr Ser Tyr Phe Ser Glu Tyr Leu Pro Pro Ile Lys Thr Glu Lys
        370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
            420                 425                 430
Ile Ala Met Cys Lys Pro Val Met Tyr Lys Asn Thr Gly Lys Ser Glu
        435                 440                 445
Gln Cys Ile Ile Val Asn Asn Glu Asp Leu Phe Phe Ile Ala Asn Lys
450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
            500                 505                 510
Glu Pro Phe Thr Asn Phe Asp Asp Ile Asp Ile Pro Val Tyr Ile Lys
        515                 520                 525
Gln Ser Ala Leu Lys Lys Ile Phe Val Asp Gly Asp Ser Leu Phe Glu
530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
            580                 585                 590
Ser Leu Phe Val Asn Trp Val Lys Gly Val Ile Asp Asp Phe Thr Ser
        595                 600                 605
Glu Ser Thr Gln Lys Ser Thr Ile Asp Lys Val Ser Asp Val Ser Ile
610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
            660                 665                 670
Leu Glu Ser Tyr Val Gly Asn Lys Gly His Ile Ile Met Thr Ile Ser
        675                 680                 685
Asn Ala Leu Lys Lys Arg Asp Gln Lys Trp Thr Asp Met Tyr Gly Leu
690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
            740                 745                 750
Asn Ile Asn Ile Asp Phe Asn Asp Ile Asp Phe Lys Leu Asn Gln Ser
        755                 760                 765
```

```
Ile Asn Leu Ala Ile Asn Ile Asp Asp Phe Ile Asn Gln Cys Ser
    770             775             780
Ile Ser Tyr Leu Met Asn Arg Met Ile Pro Leu Ala Val Lys Lys Leu
785             790             795             800
Lys Asp Phe Asp Asp Asn Leu Lys Arg Asp Leu Leu Glu Tyr Ile Asp
            805             810             815
Thr Asn Glu Leu Tyr Leu Leu Asp Glu Val Asn Ile Leu Lys Ser Lys
        820             825             830
Val Asn Arg His Leu Lys Asp Ser Ile Pro Phe Asp Leu Ser Leu Tyr
        835             840             845
Thr Lys Asp Thr Ile Leu Ile Gln Val Phe Asn Asn Tyr Ile Ser Asn
        850             855             860
Ile Ser Ser Asn Ala Ile Leu Ser Leu Ser Tyr Arg Gly Gly Arg Leu
865             870             875             880
Ile Asp Ser Ser Gly Tyr Gly Ala Thr Met Asn Val Gly Ser Asp Val
            885             890             895
Ile Phe Asn Asp Ile Gly Asn Gly Gln Phe Lys Leu Asn Asn Ser Glu
        900             905             910
Asn Ser Asn Ile Thr Ala His Gln Ser Lys Phe Val Val Tyr Asp Ser
        915             920             925
Met Phe Asp Asn Phe Ser Ile Asn Phe Trp Val Arg Thr Pro Lys Tyr
    930             935             940
Asn Asn Asn Asp Ile Gln Thr Tyr Leu Gln Asn Glu Tyr Thr Ile Ile
945             950             955             960
Ser Cys Ile Lys Asn Asp Ser Gly Trp Lys Val Ser Ile Lys Gly Asn
            965             970             975
Arg Ile Ile Trp Thr Leu Ile Asp Val Asn Ala Lys Ser Lys Ser Ile
        980             985             990
Phe Phe Glu Tyr Ser Ile Lys Asp Asn Ile Ser Asp Tyr Ile Asn Lys
        995             1000            1005
Trp Phe Ser Ile Thr Ile Thr Asn Asp Arg Leu Gly Asn Ala Asn Ile
    1010            1015            1020
Tyr Ile Asn Gly Ser Leu Lys Lys Ser Glu Lys Ile Leu Asn Leu Asp
1025            1030            1035            1040
Arg Ile Asn Ser Ser Asn Asp Ile Asp Phe Lys Leu Ile Asn Cys Thr
            1045            1050            1055
Asp Thr Thr Lys Phe Val Trp Ile Lys Asp Phe Asn Ile Phe Gly Arg
        1060            1065            1070
Glu Leu Asn Ala Thr Glu Val Ser Ser Leu Tyr Trp Ile Gln Ser Ser
        1075            1080            1085
Thr Asn Thr Leu Lys Asp Phe Trp Gly Asn Pro Leu Arg Tyr Asp Thr
        1090            1095            1100
Gln Tyr Tyr Leu Phe Asn Gln Gly Met Gln Asn Ile Tyr Ile Lys Tyr
1105            1110            1115            1120
Phe Ser Lys Ala Ser Met Gly Glu Thr Ala Pro Arg Thr Asn Phe Asn
            1125            1130            1135
Asn Ala Ala Ile Asn Tyr Gln Asn Leu Tyr Leu Gly Leu Arg Phe Ile
        1140            1145            1150
Ile Lys Lys Ala Ser Asn Ser Arg Asn Ile Asn Asn Asp Asn Ile Val
        1155            1160            1165
Arg Glu Gly Asp Tyr Ile Tyr Leu Asn Ile Asp Asn Ile Ser Asp Glu
    1170            1175            1180
Ser Tyr Arg Val Tyr Val Leu Val Asn Ser Lys Glu Ile Gln Thr Gln
```

```
                                1185                1190                1195                1200
Leu Phe Leu Ala Pro Ile Asn Asp Asp Pro Thr Phe Tyr Asp Val Leu
                1205                1210                1215
Gln Ile Lys Lys Tyr Tyr Glu Lys Thr Thr Tyr Asn Cys Gln Ile Leu
        1220                1225                1230
Cys Glu Lys Asp Thr Lys Thr Phe Gly Leu Phe Gly Ile Gly Lys Phe
        1235                1240                1245
Val Lys Asp Tyr Gly Tyr Val Trp Asp Thr Tyr Asp Asn Tyr Phe Cys
    1250                1255                1260
Ile Ser Gln Trp Tyr Leu Arg Arg Ile Ser Glu Asn Ile Asn Lys Leu
1265                1270                1275                1280
Arg Leu Gly Cys Asn Trp Gln Phe Ile Pro Val Asp Glu Gly Trp Thr
                1285                1290                1295
Glu

<210> SEQ ID NO 8
<211> LENGTH: 1315
<212> TYPE: PRT
<213> ORGANISM: Clostridium tetani

<400> SEQUENCE: 8

Met Pro Ile Thr Ile Asn Asn Phe Arg Tyr Ser Asp Pro Val Asn Asn
 1               5                  10                  15
Asp Thr Ile Ile Met Met Glu Pro Pro Tyr Cys Lys Gly Leu Asp Ile
                20                  25                  30
Tyr Tyr Lys Ala Phe Lys Ile Thr Asp Arg Ile Trp Ile Val Pro Glu
            35                  40                  45
Arg Tyr Glu Phe Gly Thr Lys Pro Glu Asp Phe Asn Pro Pro Ser Ser
    50                  55                  60
Leu Ile Glu Gly Ala Ser Glu Tyr Tyr Asp Pro Asn Tyr Leu Arg Thr
65                  70                  75                  80
Asp Ser Asp Lys Asp Arg Phe Leu Gln Thr Met Val Lys Leu Phe Asn
                85                  90                  95
Arg Ile Lys Asn Asn Val Ala Gly Glu Ala Leu Leu Asp Lys Ile Ile
            100                 105                 110
Asn Ala Ile Pro Tyr Leu Gly Asn Ser Tyr Ser Leu Leu Asp Lys Phe
        115                 120                 125
Asp Thr Asn Ser Asn Ser Val Ser Phe Asn Leu Leu Glu Gln Asp Pro
    130                 135                 140
Ser Gly Ala Thr Thr Lys Ser Ala Met Leu Thr Asn Leu Ile Ile Phe
145                 150                 155                 160
Gly Pro Gly Pro Val Leu Asn Lys Asn Glu Val Arg Gly Ile Val Leu
                165                 170                 175
Arg Val Asp Asn Lys Asn Tyr Phe Pro Cys Arg Asp Gly Phe Gly Ser
            180                 185                 190
Ile Met Gln Met Ala Phe Cys Pro Glu Tyr Val Pro Thr Phe Asp Asn
        195                 200                 205
Val Ile Glu Asn Ile Thr Ser Leu Thr Ile Gly Lys Ser Lys Tyr Phe
    210                 215                 220
Gln Asp Pro Ala Leu Leu Leu Met His Glu Leu Ile His Val Leu His
225                 230                 235                 240
Gly Leu Tyr Gly Met Gln Val Ser Ser His Glu Ile Ile Pro Ser Lys
                245                 250                 255
Gln Glu Ile Tyr Met Gln His Thr Tyr Pro Ile Ser Ala Glu Glu Leu
            260                 265                 270
```

```
Phe Thr Phe Gly Gly Gln Asp Ala Asn Leu Ile Ser Ile Asp Ile Lys
            275                 280                 285

Asn Asp Leu Tyr Glu Lys Thr Leu Asn Asp Tyr Lys Ala Ile Ala Asn
            290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
            355                 360                 365

Ile Lys Thr Arg Leu Ser Tyr Phe Ser Met Asn His Asp Pro Val Lys
            370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
            405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
            450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
            485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
            530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
            565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
            610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
            645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
            675                 680                 685

Ser Ile Ala Glu Ser Ser Thr Gln Lys Glu Lys Ile Ile Lys Thr Ile
```

```
                690              695              700
Asp Asn Phe Leu Glu Lys Arg Tyr Glu Lys Trp Ile Glu Val Tyr Lys
705              710              715              720

Leu Val Lys Ala Lys Trp Leu Gly Thr Val Asn Thr Gln Phe Gln Lys
                725              730              735

Arg Ser Tyr Gln Met Tyr Arg Ser Leu Glu Tyr Gln Val Asp Ala Ile
                740              745              750

Lys Lys Ile Ile Asp Tyr Glu Tyr Lys Ile Tyr Ser Gly Pro Asp Lys
                755              760              765

Glu Gln Ile Ala Asp Glu Ile Asn Asn Leu Lys Asn Lys Leu Glu Glu
                770              775              780

Lys Ala Asn Lys Ala Met Ile Asn Ile Asn Ile Phe Met Arg Glu Ser
785              790              795              800

Ser Arg Ser Phe Leu Val Asn Gln Met Ile Asn Glu Ala Lys Lys Gln
                805              810              815

Leu Leu Glu Phe Asp Thr Gln Ser Lys Asn Ile Leu Met Gln Tyr Ile
                820              825              830

Lys Ala Asn Ser Lys Phe Ile Gly Ile Thr Glu Leu Lys Lys Leu Glu
                835              840              845

Ser Lys Ile Asn Lys Val Phe Ser Thr Pro Ile Pro Phe Ser Tyr Ser
850              855              860

Lys Asn Leu Asp Cys Trp Val Asp Asn Glu Glu Asp Ile Asp Val Ile
865              870              875              880

Leu Lys Lys Ser Thr Ile Leu Asn Leu Asp Ile Asn Asn Asp Ile Ile
                885              890              895

Ser Asp Ile Ser Gly Phe Asn Ser Ser Val Ile Thr Tyr Pro Asp Ala
                900              905              910

Gln Leu Val Pro Gly Ile Asn Gly Lys Ala Ile His Leu Val Asn Asn
                915              920              925

Glu Ser Ser Glu Val Ile Val His Lys Ala Met Asp Ile Glu Tyr Asn
                930              935              940

Asp Met Phe Asn Asn Phe Thr Val Ser Phe Trp Leu Arg Val Pro Lys
945              950              955              960

Val Ser Ala Ser His Leu Glu Gln Tyr Gly Thr Asn Glu Tyr Ser Ile
                965              970              975

Ile Ser Ser Met Lys Lys His Ser Leu Ser Ile Gly Ser Gly Trp Ser
                980              985              990

Val Ser Leu Lys Gly Asn Asn Leu Ile Trp Thr Leu Lys Asp Ser Ala
                995             1000             1005

Gly Glu Val Arg Gln Ile Thr Phe Arg Asp Leu Pro Asp Lys Phe Asn
               1010             1015             1020

Ala Tyr Leu Ala Asn Lys Trp Val Phe Ile Thr Ile Thr Asn Asp Arg
1025             1030             1035             1040

Leu Ser Ser Ala Asn Leu Tyr Ile Asn Gly Val Leu Met Gly Ser Ala
                1045             1050             1055

Glu Ile Thr Gly Leu Gly Ala Ile Arg Glu Asp Asn Asn Ile Thr Leu
                1060             1065             1070

Lys Leu Asp Arg Cys Asn Asn Asn Asn Gln Tyr Val Ser Ile Asp Lys
                1075             1080             1085

Phe Arg Ile Phe Cys Lys Ala Leu Asn Pro Lys Glu Ile Glu Lys Leu
                1090             1095             1100

Tyr Thr Ser Tyr Leu Ser Ile Thr Phe Leu Arg Asp Phe Trp Gly Asn
1105             1110             1115             1120
```

```
Pro Leu Arg Tyr Asp Thr Glu Tyr Tyr Leu Ile Pro Val Ala Ser Ser
        1125                1130                1135

Ser Lys Asp Val Gln Leu Lys Asn Ile Thr Asp Tyr Met Tyr Leu Thr
        1140                1145                1150

Asn Ala Pro Ser Tyr Thr Asn Gly Lys Leu Asn Ile Tyr Tyr Arg Arg
            1155                1160                1165

Leu Tyr Asn Gly Leu Lys Phe Ile Ile Lys Arg Tyr Thr Pro Asn Asn
1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
                1205                1210                1215

Ala Phe Asn Asn Leu Asp Arg Ile Leu Arg Val Gly Tyr Asn Ala Pro
                1220                1225                1230

Gly Ile Pro Leu Tyr Lys Lys Met Glu Ala Val Lys Leu Arg Asp Leu
                1235                1240                1245

Lys Thr Tyr Ser Val Gln Leu Lys Leu Tyr Asp Asp Lys Asn Ala Ser
            1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
                1285                1290                1295

Lys Ile Leu Gly Cys Asp Trp Tyr Phe Val Pro Thr Asp Glu Gly Trp
                1300                1305                1310

Thr Asn Asp
        1315

<210> SEQ ID NO 9
<211> LENGTH: 1268
<212> TYPE: PRT
<213> ORGANISM: Clostridium baratii

<400> SEQUENCE: 9

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175
```

-continued

```
Ile Ala Tyr Asp Pro Ser Glu Lys Gly Phe Gly Ser Ile Gln Leu Met
            180                 185                 190

Ser Phe Ser Thr Glu Tyr Glu Ala Phe Asn Asp Asn Thr Asp Leu
        195                 200                 205

Phe Ile Ala Asp Pro Ala Ile Ser Leu Ala His Glu Leu Ile His Val
        210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
                245                 250                 255

Glu Glu Phe Ile Thr Phe Gly Gly Gln Asp Leu Asn Ile Ile Thr Asn
                260                 265                 270

Ser Thr Asn Gln Lys Ile Tyr Val Ile Leu Leu Ser Asn Tyr Thr Ala
        275                 280                 285

Ile Ala Ser Arg Leu Ser Gln Val Asn Arg Asn Asn Ser Ala Leu Asn
        290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
                340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
        370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
                420                 425                 430

Ser Leu Cys Ile Lys Val Asn Asn Arg Asp Leu Phe Phe Val Ala Ser
        435                 440                 445

Glu Ser Ser Tyr Asn Glu Asn Gly Ile Asn Ser Pro Lys Glu Ile Asp
        450                 455                 460

Asp Thr Thr Ile Thr Asn Asn Asn Tyr Lys Lys Asn Leu Asp Glu Val
465                 470                 475                 480

Ile Leu Asp Tyr Asn Ser Asp Ala Ile Pro Asn Leu Ser Ser Arg Leu
                485                 490                 495

Leu Asn Thr Thr Ala Gln Asn Asp Ser Tyr Val Pro Lys Tyr Asp Ser
        500                 505                 510

Asn Gly Thr Ser Glu Ile Lys Glu Tyr Thr Val Asp Lys Leu Asn Val
        515                 520                 525

Phe Phe Tyr Leu Tyr Ala Gln Lys Ala Pro Glu Gly Glu Ser Ala Ile
        530                 535                 540

Ser Leu Thr Ser Ser Val Asn Thr Ala Leu Leu Asp Ala Ser Lys Val
545                 550                 555                 560

Tyr Thr Phe Phe Ser Ser Asp Phe Ile Asn Thr Val Asn Lys Pro Val
                565                 570                 575

Gln Ala Ala Leu Phe Ile Ser Trp Ile Gln Gln Val Ile Asn Asp Phe
        580                 585                 590

Thr Thr Glu Ala Thr Gln Lys Ser Thr Ile Asp Lys Ile Ala Asp Ile
        595                 600                 605
```

-continued

Ser Leu Ile Val Pro Tyr Val Gly Leu Ala Leu Asn Ile Gly Asn Glu
610                 615                 620

Val Gln Lys Gly Asn Phe Lys Glu Ala Ile Glu Leu Leu Gly Ala Gly
625                 630                 635                 640

Ile Leu Leu Glu Phe Val Pro Glu Leu Leu Ile Pro Thr Ile Leu Val
                645                 650                 655

Phe Thr Ile Lys Ser Phe Ile Asn Ser Asp Ser Lys Asn Lys Ile
            660                 665                 670

Ile Lys Ala Ile Asn Asn Ala Leu Arg Glu Arg Glu Leu Lys Trp Lys
            675                 680                 685

Glu Val Tyr Ser Trp Ile Val Ser Asn Trp Leu Thr Arg Ile Asn Thr
690                 695                 700

Gln Phe Asn Lys Arg Lys Glu Gln Met Tyr Gln Ala Leu Gln Asn Gln
705                 710                 715                 720

Val Asp Gly Ile Lys Lys Ile Glu Tyr Lys Tyr Asn Asn Tyr Thr
                725                 730                 735

Leu Asp Glu Lys Asn Arg Leu Arg Ala Glu Tyr Asn Ile Tyr Ser Ile
            740                 745                 750

Lys Glu Glu Leu Asn Lys Lys Val Ser Leu Ala Met Gln Asn Ile Asp
            755                 760                 765

Arg Phe Leu Thr Glu Ser Ser Ile Ser Tyr Leu Met Lys Leu Ile Asn
770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                805                 810                 815

Ser Val Pro Glu Leu Asn Asn Leu Val Ser Asn Thr Leu Asn Asn Ser
            820                 825                 830

Ile Pro Phe Glu Leu Ser Glu Tyr Thr Asn Asp Lys Ile Leu Ile His
            835                 840                 845

Ile Leu Ile Arg Phe Tyr Lys Arg Ile Ile Asp Ser Ser Ile Leu Asn
850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                885                 890                 895

Gln Phe Gly Ile Tyr Ser Ser Arg Leu Ser Glu Val Asn Ile Thr Gln
            900                 905                 910

Asn Asn Thr Ile Ile Tyr Asn Ser Arg Tyr Gln Asn Phe Ser Val Ser
            915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Ser Gly Trp Lys
945                 950                 955                 960

Ile Ser Leu Asn Tyr Asn Asn Ile Ile Trp Thr Leu Gln Asp Thr Thr
                965                 970                 975

Gly Asn Asn Gln Lys Leu Val Phe Asn Tyr Thr Gln Met Ile Asp Ile
            980                 985                 990

Ser Asp Tyr Ile Asn Lys Trp Thr Phe Val Thr Ile Thr Asn Asn Arg
            995                 1000                1005

Leu Gly His Ser Lys Leu Tyr Ile Asn Gly Asn Leu Thr Asp Gln Lys
1010                1015                1020

Ser Ile Leu Asn Leu Gly Asn Ile His Val Asp Asp Asn Ile Leu Phe

```
                                1025                1030                1035                1040
Lys Ile Val Gly Cys Asn Asp Thr Arg Tyr Val Gly Ile Arg Tyr Phe
                    1045                1050                1055

Lys Ile Phe Asn Met Glu Leu Asp Lys Thr Glu Ile Glu Thr Leu Tyr
            1060                1065                1070

His Ser Glu Pro Asp Ser Thr Ile Leu Lys Asp Phe Trp Gly Asn Tyr
        1075                1080                1085

Leu Leu Tyr Asn Lys Lys Tyr Tyr Leu Asn Leu Leu Lys Pro Asn
        1090                1095                1100

Met Ser Val Thr Lys Asn Ser Asp Ile Leu Asn Ile Asn Arg Gln Arg
1105                1110                1115                1120

Gly Ile Tyr Ser Lys Thr Asn Ile Phe Ser Asn Ala Arg Leu Tyr Thr
                1125                1130                1135

Gly Val Glu Val Ile Ile Arg Lys Val Gly Ser Thr Asp Ser Asn
            1140                1145                1150

Thr Asp Asn Phe Val Arg Lys Asn Asp Thr Val Tyr Ile Asn Val Val
        1155                1160                1165

Asp Gly Asn Ser Glu Tyr Gln Leu Tyr Ala Asp Val Ser Thr Ser Ala
    1170                1175                1180

Val Glu Lys Thr Ile Lys Leu Arg Arg Ile Ser Asn Ser Asn Tyr Asn
1185                1190                1195                1200

Ser Asn Gln Met Ile Ile Met Asp Ser Ile Gly Asp Asn Cys Thr Met
                1205                1210                1215

Asn Phe Lys Thr Asn Asn Gly Asn Asp Ile Gly Leu Leu Gly Phe His
            1220                1225                1230

Leu Asn Asn Leu Val Ala Ser Ser Trp Tyr Tyr Lys Asn Ile Arg Asn
        1235                1240                1245

Asn Thr Arg Asn Asn Gly Cys Phe Trp Ser Phe Ile Ser Lys Glu His
    1250                1255                1260

Gly Trp Gln Glu
1265

<210> SEQ ID NO 10
<211> LENGTH: 1251
<212> TYPE: PRT
<213> ORGANISM: Clostridium butyricum

<400> SEQUENCE: 10

Met Pro Thr Ile Asn Ser Phe Asn Tyr Asn Asp Pro Val Asn Arg
 1               5                   10                  15

Thr Ile Leu Tyr Ile Lys Pro Gly Gly Cys Gln Gln Phe Tyr Lys Ser
            20                  25                  30

Phe Asn Ile Met Lys Asn Ile Trp Ile Ile Pro Glu Arg Asn Val Ile
        35                  40                  45

Gly Thr Ile Pro Gln Asp Phe Leu Pro Pro Thr Ser Leu Lys Asn Gly
    50                  55                  60

Asp Ser Ser Tyr Tyr Asp Pro Asn Tyr Leu Gln Ser Asp Gln Glu Lys
65                  70                  75                  80

Asp Lys Phe Leu Lys Ile Val Thr Lys Ile Phe Asn Arg Ile Asn Asp
                85                  90                  95

Asn Leu Ser Gly Arg Ile Leu Leu Glu Glu Leu Ser Lys Ala Asn Pro
            100                 105                 110

Tyr Leu Gly Asn Asp Asn Thr Pro Asp Gly Asp Phe Ile Ile Asn Asp
        115                 120                 125

Ala Ser Ala Val Pro Ile Gln Phe Ser Asn Gly Ser Gln Ser Ile Leu
```

```
            130                 135                 140
Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Lys Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
                530                 535                 540

Leu Leu Glu Gln Pro Lys Ile Tyr Thr Phe Phe Ser Ser Glu Phe Ile
545                 550                 555                 560
```

```
Asn Asn Val Asn Lys Pro Val Gln Ala Ala Leu Phe Val Gly Trp Ile
            565             570             575
Gln Gln Val Leu Val Asp Phe Thr Thr Glu Ala Asn Gln Lys Ser Thr
        580             585             590
Val Asp Lys Ile Ala Asp Ile Ser Ile Val Val Pro Tyr Ile Gly Leu
        595             600             605
Ala Leu Asn Ile Gly Asn Glu Ala Gln Lys Gly Asn Phe Lys Asp Ala
        610             615             620
Leu Glu Leu Leu Gly Ala Gly Ile Leu Leu Glu Phe Glu Pro Glu Leu
625             630             635             640
Leu Ile Pro Thr Ile Leu Val Phe Thr Ile Lys Ser Phe Leu Gly Ser
            645             650             655
Ser Asp Asn Lys Asn Lys Val Ile Lys Ala Ile Asn Asn Ala Leu Lys
            660             665             670
Glu Arg Asp Glu Lys Trp Lys Glu Val Tyr Ser Phe Ile Val Ser Asn
            675             680             685
Trp Met Thr Lys Ile Asn Thr Gln Phe Asn Lys Arg Lys Glu Gln Met
        690             695             700
Tyr Gln Ala Leu Gln Asn Gln Val Asn Ala Leu Lys Ala Ile Ile Glu
705             710             715             720
Ser Lys Tyr Asn Ser Tyr Thr Leu Glu Glu Lys Asn Glu Leu Thr Asn
            725             730             735
Lys Tyr Asp Ile Glu Gln Ile Glu Asn Glu Leu Asn Gln Lys Val Ser
            740             745             750
Ile Ala Met Asn Asn Ile Asp Arg Phe Leu Thr Glu Ser Ser Ile Ser
            755             760             765
Tyr Leu Met Lys Leu Ile Asn Glu Val Lys Ile Asn Lys Leu Arg Glu
770             775             780
Tyr Asp Glu Asn Val Lys Thr Tyr Leu Leu Asp Tyr Ile Ile Lys His
785             790             795             800
Gly Ser Ile Leu Gly Glu Ser Gln Gln Glu Leu Asn Ser Met Val Ile
            805             810             815
Asp Thr Leu Asn Asn Ser Ile Pro Phe Lys Leu Ser Ser Tyr Thr Asp
            820             825             830
Asp Lys Ile Leu Ile Ser Tyr Phe Asn Lys Phe Phe Lys Arg Ile Lys
            835             840             845
Ser Ser Ser Val Leu Asn Met Arg Tyr Lys Asn Asp Lys Tyr Val Asp
850             855             860
Thr Ser Gly Tyr Asp Ser Asn Ile Asn Ile Asn Gly Asp Val Tyr Lys
865             870             875             880
Tyr Pro Thr Asn Lys Asn Gln Phe Gly Ile Tyr Asn Asp Lys Leu Ser
            885             890             895
Glu Val Asn Ile Ser Gln Asn Asp Tyr Ile Ile Tyr Asp Asn Lys Tyr
            900             905             910
Lys Asn Phe Ser Ile Ser Phe Trp Val Arg Ile Pro Asn Tyr Asp Asn
            915             920             925
Lys Ile Val Asn Val Asn Asn Glu Tyr Thr Ile Ile Asn Cys Met Arg
            930             935             940
Asp Asn Asn Ser Gly Trp Lys Val Ser Leu Asn His Asn Glu Ile Ile
945             950             955             960
Trp Thr Leu Gln Asp Asn Ser Gly Ile Asn Gln Lys Leu Ala Phe Asn
            965             970             975
Tyr Gly Asn Ala Asn Gly Ile Ser Asp Tyr Ile Asn Lys Trp Ile Phe
            980             985             990
```

```
Val Thr Ile Thr Asn Asp Arg Leu Gly Asp Ser Lys Leu Tyr Ile Asn
        995                 1000                1005
Gly Asn Leu Ile Asp Lys Lys Ser Ile Leu Asn Leu Gly Asn Ile His
    1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                1045                1050                1055

Thr Glu Ile Gln Thr Leu Tyr Asn Asn Glu Pro Asn Ala Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asn Arg Arg Thr Asp Ser
    1090                1095                1100

Thr Leu Ser Ile Asn Asn Ile Arg Ser Thr Ile Leu Leu Ala Asn Arg
1105                1110                1115                1120
Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Leu Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Cys Thr Met Asn Phe
1185                1190                1195                1200
Lys Asn Asn Asn Gly Asn Asn Ile Gly Leu Leu Gly Phe Lys Ala Asp
                1205                1210                1215

Thr Val Val Ala Ser Thr Trp Tyr Tyr Thr His Met Arg Asp Asn Thr
            1220                1225                1230

Asn Ser Asn Gly Phe Phe Trp Asn Phe Ile Ser Glu Glu His Gly Trp
        1235                1240                1245

Gln Glu Lys
    1250

<210> SEQ ID NO 11
<211> LENGTH: 25
<212> TYPE: PRT
<213> ORGANISM: Artificial Sequence
<220> FEATURE:
<223> OTHER INFORMATION: BoNT/A di-chain loop region

<400> SEQUENCE: 11

Cys Val Arg Gly Ile Ile Thr Ser Lys Thr Lys Ser Leu Asp Lys Gly
 1               5                  10                  15

Tyr Asn Lys Ala Leu Asn Asp Leu Cys
            20                  25

<210> SEQ ID NO 12
<211> LENGTH: 10
<212> TYPE: PRT
<213> ORGANISM: Artificial Sequence
<220> FEATURE:
<223> OTHER INFORMATION: BoNT/B di-chain loop region

<400> SEQUENCE: 12

Cys Lys Ser Val Lys Ala Pro Gly Ile Cys
 1               5                  10
```

<210> SEQ ID NO 13
<211> LENGTH: 17
<212> TYPE: PRT
<213> ORGANISM: Artificial Sequence
<220> FEATURE:
<223> OTHER INFORMATION: BoNT/C1 di-chain loop region

<400> SEQUENCE: 13

Cys His Lys Ala Ile Asp Gly Arg Ser Leu Tyr Asn Lys Thr Leu Asp
1 5 10 15

Cys

<210> SEQ ID NO 14
<211> LENGTH: 14
<212> TYPE: PRT
<213> ORGANISM: Artificial Sequence
<220> FEATURE:
<223> OTHER INFORMATION: BoNT/D di-chain loop region

<400> SEQUENCE: 14

Cys Leu Arg Leu Thr Lys Asn Ser Arg Asp Asp Ser Thr Cys
1 5 10

<210> SEQ ID NO 15
<211> LENGTH: 15
<212> TYPE: PRT
<213> ORGANISM: Artificial Sequence
<220> FEATURE:
<223> OTHER INFORMATION: BoNT/E di-chain loop region

<400> SEQUENCE: 15

Cys Lys Asn Ile Val Ser Val Lys Gly Ile Arg Lys Ser Ile Cys
1 5 10 15

<210> SEQ ID NO 16
<211> LENGTH: 17
<212> TYPE: PRT
<213> ORGANISM: Artificial Sequence
<220> FEATURE:
<223> OTHER INFORMATION: BoNT/F di-chain loop region

<400> SEQUENCE: 16

Cys Lys Ser Val Ile Pro Arg Lys Gly Thr Lys Ala Pro Pro Arg Leu
1 5 10 15

Cys

<210> SEQ ID NO 17
<211> LENGTH: 15
<212> TYPE: PRT
<213> ORGANISM: Artificial Sequence
<220> FEATURE:
<223> OTHER INFORMATION: BoNT/G di-chain loop region

<400> SEQUENCE: 17

Cys Lys Pro Val Met Tyr Lys Asn Thr Gly Lys Ser Glu Gln Cys
1 5 10 15

<210> SEQ ID NO 18
<211> LENGTH: 29
<212> TYPE: PRT
<213> ORGANISM: Artificial Sequence
<220> FEATURE:
<223> OTHER INFORMATION: TeNT di-chain loop region

<400> SEQUENCE: 18

```
Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25
```

<210> SEQ ID NO 19
<211> LENGTH: 15
<212> TYPE: PRT
<213> ORGANISM: Artificial Sequence
<220> FEATURE:
<223> OTHER INFORMATION: BaNT di-chain loop region

<400> SEQUENCE: 19

```
Cys Lys Ser Ile Val Ser Lys Lys Gly Thr Lys Asn Ser Leu Cys
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: BuNT di-chain loop region

<400> SEQUENCE: 20

```
Cys Lys Asn Ile Val Ser Val Lys Gly Ile Arg Lys Ser Ile Cys
1               5                   10                  15
```

<210> SEQ ID NO 21
<211> LENGTH: 5
<212> TYPE: PRT
<213> ORGANISM: Artificial Sequence
<220> FEATURE:
<223> OTHER INFORMATION: Bovine enterokinase protease cleavage site

<400> SEQUENCE: 21

```
Asp Asp Asp Asp Lys
1               5
```

<210> SEQ ID NO 22
<211> LENGTH: 7
<212> TYPE: PRT
<213> ORGANISM: Artificial Sequence
<220> FEATURE:
<223> OTHER INFORMATION: Tobacco Etch Virus protease cleavage site
      consensus sequence
<220> FEATURE:
<221> NAME/KEY: VARIANT
<222> LOCATION: 2, 3, 5
<223> OTHER INFORMATION: Xaa can be amino amino acid

<400> SEQUENCE: 22

```
Glu Xaa Xaa Tyr Xaa Gln Gly
1               5
```

<210> SEQ ID NO 23
<211> LENGTH: 7
<212> TYPE: PRT
<213> ORGANISM: Artificial Sequence
<220> FEATURE:
<223> OTHER INFORMATION: Tobacco Etch Virus protease cleavage site
      consensus sequence
<220> FEATURE:
<221> NAME/KEY: VARIANT
<222> LOCATION: 2, 3, 5
<223> OTHER INFORMATION: Xaa can be any amino acid

<400> SEQUENCE: 23

```
Glu Xaa Xaa Tyr Xaa Gln Ser
1               5
```

<210> SEQ ID NO 24
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 24

Glu Asn Leu Tyr Phe Gln Gly
 1               5

<210> SEQ ID NO 25
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 25

Glu Asn Leu Tyr Phe Gln Ser
 1               5

<210> SEQ ID NO 26
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 26

Glu Asn Ile Tyr Thr Gln Gly
 1               5

<210> SEQ ID NO 27
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 27

Glu Asn Ile Tyr Thr Gln Ser
 1               5

<210> SEQ ID NO 28
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 28

Glu Asn Ile Tyr Leu Gln Gly
 1               5

<210> SEQ ID NO 29
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 29

Glu Asn Ile Tyr Leu Gln Ser
 1               5

```
<210> SEQ ID NO 30
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 30

Glu Asn Val Tyr Phe Gln Gly
 1               5

<210> SEQ ID NO 31
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 31

Glu Asn Val Tyr Ser Gln Ser
 1               5

<210> SEQ ID NO 32
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 32

Glu Asn Val Tyr Ser Gln Gly
 1               5

<210> SEQ ID NO 33
<211> LENGTH: 7
<212> TYPE: PRT
<213> ORGANISM: Artificial Sequence
<220> FEATURE:
<223> OTHER INFORMATION: Tobacco Etch Virus protease cleavage site

<400> SEQUENCE: 33

Glu Asn Val Tyr Ser Gln Ser
 1               5

<210> SEQ ID NO 34
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site consensus sequence
<220> FEATURE:
<221> NAME/KEY: VARIANT
<222> LOCATION: 1, 2
<223> OTHER INFORMATION: Xaa can be any amino acid

<400> SEQUENCE: 34

Xaa Xaa Val Arg Phe Gln Gly
 1               5

<210> SEQ ID NO 35
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site consensus sequence
<220> FEATURE:
<221> NAME/KEY: VARIANT
<222> LOCATION: 1, 2
```

```
<223> OTHER INFORMATION: Xaa can be any amino acid

<400> SEQUENCE: 35

Xaa Xaa Val Arg Phe Gln Ser
 1               5

<210> SEQ ID NO 36
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 36

Glu Thr Val Arg Phe Gln Gly
 1               5

<210> SEQ ID NO 37
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 37

Glu Thr Val Arg Phe Gln Ser
 1               5

<210> SEQ ID NO 38
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 38

Asn Asn Val Arg Phe Gln Gly
 1               5

<210> SEQ ID NO 39
<211> LENGTH: 7
<212> TYPE: PRT
<213> ORGANISM: Artificial Sequence
<220> FEATURE:
<223> OTHER INFORMATION: Tobacco Vein Mottling Virus protease cleavage
      site

<400> SEQUENCE: 39

Asn Asn Val Arg Phe Gln Ser
 1               5

<210> SEQ ID NO 40
<211> LENGTH: 7
<212> TYPE: PRT
<213> ORGANISM: Artificial Sequence
<220> FEATURE:
<223> OTHER INFORMATION: Human Rhinovirus 3C protease cleavage site
      consensus sequence
<220> FEATURE:
<221> NAME/KEY: VARIANT
<222> LOCATION: 1
<223> OTHER INFORMATION: Xaa can be amino acid, with D or E preferred
<220> FEATURE:
<221> NAME/KEY: VARIANT
<222> LOCATION: 2
<223> OTHER INFORMATION: Xaa can be G, A, V, L, I, M, S or T
```

```
<400> SEQUENCE: 40

Xaa Xaa Leu Phe Gln Gly Pro
  1               5

<210> SEQ ID NO 41
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 41

Glu Ala Leu Phe Gln Gly Pro
  1               5

<210> SEQ ID NO 42
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 42

Glu Val Leu Phe Gln Gly Pro
  1               5

<210> SEQ ID NO 43
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 43

Glu Leu Leu Phe Gln Gly Pro
  1               5

<210> SEQ ID NO 44
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 44

Asp Ala Leu Phe Gln Gly Pro
  1               5

<210> SEQ ID NO 45
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 45

Asp Val Leu Phe Gln Gly Pro
  1               5

<210> SEQ ID NO 46
<211> LENGTH: 7
<212> TYPE: PRT
<213> ORGANISM: Artificial Sequence
<220> FEATURE:
<223> OTHER INFORMATION: Human Rhinovirus 3C protease cleavage site

<400> SEQUENCE: 46
```

```
Asp Leu Leu Phe Gln Gly Pro
1               5

<210> SEQ ID NO 47
<211> LENGTH: 6
<212> TYPE: PRT
<213> ORGANISM: Artificial Sequence
<220> FEATURE:
<223> OTHER INFORMATION: Subtilisin cleavage site consensus sequence
<220> FEATURE:
<221> NAME/KEY: VARIANT
<222> LOCATION: 1, 2, 3, 4
<223> OTHER INFORMATION: Xaa can be any amino acid

<400> SEQUENCE: 47

Xaa Xaa Xaa Xaa His Tyr
1               5

<210> SEQ ID NO 48
<211> LENGTH: 6
<212> TYPE: PRT
<213> ORGANISM: Artificial Sequence
<220> FEATURE:
<223> OTHER INFORMATION: Subtilisin cleavage site consensus sequence
<220> FEATURE:
<221> NAME/KEY: VARIANT
<222> LOCATION: 1, 2, 3, 4
<223> OTHER INFORMATION: Xaa can be any amino acid

<400> SEQUENCE: 48

Xaa Xaa Xaa Xaa Tyr His
1               5

<210> SEQ ID NO 49
<211> LENGTH: 2
<212> TYPE: PRT
<213> ORGANISM: Artificial Sequence
<220> FEATURE:
<223> OTHER INFORMATION: Subtilisin cleavage site

<400> SEQUENCE: 49

His Tyr
1

<210> SEQ ID NO 50
<211> LENGTH: 2
<212> TYPE: PRT
<213> ORGANISM: Artificial Sequence
<220> FEATURE:
<223> OTHER INFORMATION: Subtilisin cleavage site

<400> SEQUENCE: 50

Tyr His
1

<210> SEQ ID NO 51
<211> LENGTH: 6
<212> TYPE: PRT
<213> ORGANISM: Artificial Sequence
<220> FEATURE:
<223> OTHER INFORMATION: Subtilisin cleavage site

<400> SEQUENCE: 51

Pro Gly Ala Ala His Tyr
1               5

<210> SEQ ID NO 52
<211> LENGTH: 6
<212> TYPE: PRT
```

```
<213> ORGANISM: Artificial Sequence
<220> FEATURE:
<223> OTHER INFORMATION: Hydroxylamine cleavage site

<400> SEQUENCE: 52

Asn Gly Asn Gly Asn Gly
 1               5

<210> SEQ ID NO 53
<211> LENGTH: 2
<212> TYPE: PRT
<213> ORGANISM: Artificial Sequence
<220> FEATURE:
<223> OTHER INFORMATION: Hydroxylamine cleavage site

<400> SEQUENCE: 53

Asn Gly
 1

<210> SEQ ID NO 54
<211> LENGTH: 5
<212> TYPE: PRT
<213> ORGANISM: Artificial Sequence
<220> FEATURE:
<223> OTHER INFORMATION: SUMO/ULP-1 protease cleavage site consensus
      sequence
<220> FEATURE:
<221> NAME/KEY: VARIANT
<222> LOCATION: 3, 4, 5
<223> OTHER INFORMATION: Xaa can be any amino acid

<400> SEQUENCE: 54

Gly Gly Xaa Xaa Xaa
 1               5

<210> SEQ ID NO 55
<211> LENGTH: 98
<212> TYPE: PRT
<213> ORGANISM: Artificial Sequence
<220> FEATURE:
<223> OTHER INFORMATION: SUMO/ULP-1 protease cleavage site

<400> SEQUENCE: 55

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Gly

<210> SEQ ID NO 56
<211> LENGTH: 5
<212> TYPE: PRT
<213> ORGANISM: Artificial Sequence
<220> FEATURE:
<223> OTHER INFORMATION: Caspase 3 protease cleavage site consensus
      sequence
<220> FEATURE:
<221> NAME/KEY: VARIANT
```

```
<222> LOCATION: 2
<223> OTHER INFORMATION: Xaa can be any amino acid with E preferred
<220> FEATURE:
<221> NAME/KEY: VARIANT
<222> LOCATION: 3
<223> OTHER INFORMATION: Xaa can be any amino acid
<220> FEATURE:
<221> NAME/KEY: VARIANT
<222> LOCATION: 5
<223> OTHER INFORMATION: Xaa can be any amino acid with G or S preferred

<400> SEQUENCE: 56

Asp Xaa Xaa Asp Xaa
1               5

<210> SEQ ID NO 57
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 57

Asp Glu Val Asp Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 58

Asp Glu Val Asp Ser
1               5

<210> SEQ ID NO 59
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 59

Asp Glu Pro Asp Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 60

Asp Glu Pro Asp Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 61

Asp Glu Leu Asp Gly
1               5
```

```
<210> SEQ ID NO 62
<211> LENGTH: 5
<212> TYPE: PRT
<213> ORGANISM: Artificial Sequence
<220> FEATURE:
<223> OTHER INFORMATION: Caspase 3 protease cleavage site

<400> SEQUENCE: 62

Asp Glu Leu Asp Ser
 1               5

<210> SEQ ID NO 63
<211> LENGTH: 4
<212> TYPE: PRT
<213> ORGANISM: Artificial Sequence
<220> FEATURE:
<223> OTHER INFORMATION: Flexible G-spacer

<400> SEQUENCE: 63

Gly Gly Gly Gly
 1

<210> SEQ ID NO 64
<211> LENGTH: 5
<212> TYPE: PRT
<213> ORGANISM: Artificial Sequence
<220> FEATURE:
<223> OTHER INFORMATION: Flexible G-spacer

<400> SEQUENCE: 64

Gly Gly Gly Gly Ser
 1               5

<210> SEQ ID NO 65
<211> LENGTH: 4
<212> TYPE: PRT
<213> ORGANISM: Artificial Sequence
<220> FEATURE:
<223> OTHER INFORMATION: Flexible A-spacer

<400> SEQUENCE: 65

Ala Ala Ala Ala
 1

<210> SEQ ID NO 66
<211> LENGTH: 5
<212> TYPE: PRT
<213> ORGANISM: Artificial Sequence
<220> FEATURE:
<223> OTHER INFORMATION: Flexible A-spacer

<400> SEQUENCE: 66

Ala Ala Ala Ala Val
 1               5

<210> SEQ ID NO 67
<211> LENGTH: 30
<212> TYPE: PRT
<213> ORGANISM: Homo sapiens

<400> SEQUENCE: 67

Gly Trp Thr Leu Asn Ser Ala Gly Tyr Leu Leu Gly Pro His Ala Val
 1               5                  10                  15

Gly Asn His Arg Ser Phe Ser Asp Lys Asn Gly Leu Thr Ser
                20                  25                  30
```

-continued

<210> SEQ ID NO 68
<211> LENGTH: 59
<212> TYPE: PRT
<213> ORGANISM: Homo sapiens

<400> SEQUENCE: 68

Glu Leu Arg Pro Glu Asp Met Lys Pro Gly Ser Phe Asp Arg Ser
1               5                   10                  15

Ile Pro Glu Asn Asn Ile Met Arg Thr Ile Glu Phe Leu Ser Phe
            20                  25                  30

Leu His Leu Lys Glu Ala Gly Ala Leu Asp Arg Leu Leu Asp Leu Pro
        35                  40                  45

Ala Ala Ala Ser Ser Glu Asp Ile Glu Arg Ser
    50                  55

<210> SEQ ID NO 69
<211> LENGTH: 64
<212> TYPE: PRT
<213> ORGANISM: Homo sapiens

<400> SEQUENCE: 69

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Glu Lys Asn Glu Ser
    50                  55                  60

<210> SEQ ID NO 70
<211> LENGTH: 59
<212> TYPE: PRT
<213> ORGANISM: Homo sapiens

<400> SEQUENCE: 70

Met Arg Ser Pro Ser Ala Ala Trp Leu Leu Gly Ala Ala Ile Leu Leu
1               5                   10                  15

Ala Ala Ser Leu Ser Cys Ser Gly Thr Ile Gln Gly Thr Asn Arg Ser
            20                  25                  30

Ser Lys Gly Arg Ser Leu Ile Gly Lys Val Asp Gly Thr Ser His Val
        35                  40                  45

Thr Gly Lys Gly Val Thr Val Glu Thr Val Phe
    50                  55

<210> SEQ ID NO 71
<211> LENGTH: 60
<212> TYPE: PRT
<213> ORGANISM: Homo sapiens

<400> SEQUENCE: 71

Met Lys Ala Leu Ile Phe Ala Ala Ala Gly Leu Leu Leu Leu Leu Pro
1               5                   10                  15

Thr Phe Cys Gln Ser Gly Met Glu Asn Asp Thr Asn Asn Leu Ala Lys
            20                  25                  30

Pro Thr Leu Pro Ile Lys Thr Phe Arg Gly Ala Pro Pro Asn Ser Phe
        35                  40                  45

Glu Glu Phe Pro Phe Ser Ala Leu Glu Gly Trp Thr
    50                  55                  60

<210> SEQ ID NO 72
<211> LENGTH: 70
<212> TYPE: PRT
<213> ORGANISM: Homo sapiens

<400> SEQUENCE: 72

Met Trp Gly Arg Leu Leu Trp Pro Leu Val Leu Gly Phe Ser Leu
1               5                   10                  15

Ser Gly Gly Thr Gln Thr Pro Ser Val Tyr Asp Glu Ser Gly Ser Thr
                20                  25                  30

Gly Gly Gly Asp Asp Ser Thr Pro Ser Ile Leu Pro Ala Pro Arg Gly
            35                  40                  45

Tyr Pro Gly Gln Val Cys Ala Asn Asp Ser Asp Thr Leu Glu Leu Pro
    50                  55                  60

Asp Ser Ser Arg Ala Leu
65                  70

<210> SEQ ID NO 73
<211> LENGTH: 116
<212> TYPE: PRT
<213> ORGANISM: Homo sapiens

<400> SEQUENCE: 73

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
                20                  25                  30

Gln Phe Leu Gln Lys Ser Leu Ala Ala Ala Ala Gly Lys Gln Glu Leu
            35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115

<210> SEQ ID NO 74
<211> LENGTH: 170
<212> TYPE: PRT
<213> ORGANISM: Homo sapiens

<400> SEQUENCE: 74

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
                20                  25                  30

Leu Glu Ala Asp Phe Leu Thr Asn Met His Thr Ser Lys Ile Ser Lys
            35                  40                  45

Ala His Val Pro Ser Trp Lys Met Thr Leu Leu Asn Val Cys Ser Leu
    50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

```
Ser Leu Glu Ala Met Leu Thr Ile Tyr Gln Leu His Lys Ile Cys His
                100                 105                 110

Ser Arg Ala Phe Gln His Trp Glu Leu Ile Gln Glu Asp Ile Leu Asp
            115                 120                 125

Thr Gly Asn Asp Lys Asn Gly Lys Glu Glu Val Ile Lys Arg Lys Ile
        130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 75
<211> LENGTH: 103
<212> TYPE: PRT
<213> ORGANISM: Homo sapiens

<400> SEQUENCE: 75

Met Ala Ser Arg Trp Ala Val Gln Leu Leu Val Ala Ala Trp Ser
 1               5                  10                  15

Met Gly Cys Gly Glu Ala Leu Lys Cys Tyr Thr Cys Lys Glu Pro Met
                20                  25                  30

Thr Ser Ala Ser Cys Arg Thr Ile Thr Arg Cys Lys Pro Glu Asp Thr
            35                  40                  45

Ala Cys Met Thr Thr Leu Val Thr Val Glu Ala Glu Tyr Pro Phe Asn
    50                  55                  60

Gln Ser Pro Val Val Thr Arg Ser Cys Ser Ser Ser Cys Val Ala Thr
65                  70                  75                  80

Asp Pro Asp Ser Ile Gly Ala Ala His Leu Ile Phe Cys Cys Phe Arg
                85                  90                  95

Asp Leu Cys Asn Ser Glu Leu
                100

<210> SEQ ID NO 76
<211> LENGTH: 97
<212> TYPE: PRT
<213> ORGANISM: Homo sapiens

<400> SEQUENCE: 76

Met Gln Leu Gly Thr Gly Leu Leu Leu Ala Ala Val Leu Ser Leu Gln
 1               5                  10                  15

Leu Ala Ala Ala Glu Ala Ile Trp Cys His Gln Cys Thr Gly Phe Gly
                20                  25                  30

Gly Cys Ser His Gly Ser Arg Cys Leu Arg Asp Ser Thr His Cys Val
            35                  40                  45

Thr Thr Ala Thr Arg Val Leu Ser Asn Thr Glu Asp Leu Pro Leu Val
    50                  55                  60

Thr Lys Met Cys His Ile Gly Cys Pro Asp Ile Pro Ser Leu Gly Leu
65                  70                  75                  80

Gly Pro Tyr Val Ser Ile Ala Cys Cys Gln Thr Ser Leu Cys Asn His
                85                  90                  95

Asp
```